(12) United States Patent
Augustin et al.

(10) Patent No.: US 12,227,780 B2
(45) Date of Patent: Feb. 18, 2025

(54) **ISOTHIOCYANATE CONTAINING *BRASSICACEAE* PRODUCTS AND METHOD OF PREPARATION THEREOF**

(71) Applicant: Commonwealth Scientific and Industrial Research Organisation, Acton (AU)

(72) Inventors: Mary Ann Augustin, Wheelers Hill (AU); Netsanet Shiferaw Terefe, Werribee South (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 104 days.

(21) Appl. No.: 16/651,974

(22) PCT Filed: Sep. 27, 2018

(86) PCT No.: PCT/AU2018/051063
§ 371 (c)(1),
(2) Date: Mar. 27, 2020

(87) PCT Pub. No.: WO2019/060963
PCT Pub. Date: Apr. 4, 2019

(65) Prior Publication Data
US 2020/0255872 A1   Aug. 13, 2020

(30) Foreign Application Priority Data
Sep. 28, 2017 (AU) .................. 2017903944

(51) Int. Cl.
*C12P 13/00* (2006.01)
*A23L 33/135* (2016.01)
*C12N 1/20* (2006.01)

(52) U.S. Cl.
CPC ............. *C12P 13/00* (2013.01); *A23L 33/135* (2016.08); *C12N 1/20* (2013.01); *A23V 2400/169* (2023.08); *A23V 2400/321* (2023.08); *C12Y 302/01147* (2013.01)

(58) Field of Classification Search
CPC ...... A23L 33/135; A23L 33/105; A23L 19/01; C12P 11/00; C12P 13/00; C12P 39/00; C12R 1/01; C12R 1/25; C12R 1/225; C12R 2001/01; C12R 2001/225; C12N 1/20; C12N 1/205; C12N 9/2402; C12Y 302/01147; A23Y 2220/67; A23Y 2260/35; A23B 7/105; A23V 2200/3204; A23V 2400/169; A23V 2400/321; A61K 35/744; A61K 35/747; A61K 36/31

See application file for complete search history.

(56) References Cited

U.S. PATENT DOCUMENTS

| | | | | |
|---|---|---|---|---|
| 2010/0040732 | A1* | 2/2010 | Van Drunen | A23C 9/1275 426/18 |
| 2011/0045139 | A1* | 2/2011 | Holley | A23L 13/428 426/59 |
| 2013/0230624 | A1* | 9/2013 | Augustin | C12P 19/02 426/53 |
| 2016/0279090 | A1 | 9/2016 | Kosi-Kupe et al. | |
| 2016/0354448 | A1* | 12/2016 | Cornblatt | A61K 31/26 |
| 2018/0200344 | A9* | 7/2018 | Cornblatt | A61K 31/7028 |

FOREIGN PATENT DOCUMENTS

| | | | |
|---|---|---|---|
| AU | 2008209543 | 7/2007 | |
| AU | 2011281653 | 1/2012 | |
| AU | 2013346709 | 5/2014 | |
| JP | 2014-506597 | 3/2014 | |
| KR | 2011 0101930 | 9/2011 | |
| KR | 1020100021310 | 7/2012 | |
| KR | 2017 0079572 | 7/2017 | |
| KR | 1020170079572 | 7/2017 | |
| WO | WO2000045829 | 8/2000 | |
| WO | WO2004073418 | 9/2004 | |
| WO | WO-2004073418 A1 * | 9/2004 | ............... A23B 7/10 |
| WO | WO2005030229 | 4/2005 | |
| WO | WO 2012/116018 | 8/2012 | |
| WO | WO20013179057 | 12/2013 | |
| WO | WO 2014/008341 | 1/2014 | |
| WO | WO2014008361 | 1/2014 | |

OTHER PUBLICATIONS

Charmley et al. Grass and Forage Sci. (1997) 52: 110-121 (Year: 1997).*
Machine translation of KR 10-1164876 (published Jul. 19, 2012) downloaded from IP.cpm on Jan. 15, 2022 (Year: 2012).*
Matusheski et al. Heating decreases epithiospecifier protein activity and increases sulforaphane formation in broccoli. Phytochemistry (2004), 65, 1273-1281. (Year: 2004).*
Liang et al. Determination of sulforaphane in broccoli and cabbage by high-performance liquid chromatography. Journal of Food Composition and Analysis (2006), 19, 473-476. (Year: 2006).*
Barth et al. Microbiological Spoilage of Fruits and Vegetables (2009). In: Sperber, W., Doyle, M. (eds) Compendium of the Microbiological Spoilage of Foods and Beverages. Food Microbiology and Food Safety, p. 135-183. Springer, New York, NY. https://doi.org/10.1007/978-1-441 (Year: 2009).*
Jongaroontaprangsee et al. Effects of Drying Temperature and Particle Size on Hydration Properties of Dietary Fiber Powder from Lime and Cabbage By-Products. International Journal of Food Properties (2007), 10:4, 887-897. (Year: 2007).*

(Continued)

*Primary Examiner* — Sean C. Barron
(74) *Attorney, Agent, or Firm* — Norton Rose Fulbright US LLP

(57) ABSTRACT

The present invention relates to methods for producing isothiocyanate containing products from Brassicaceae material and lactic acid bacteria for use in such methods. The present invention also relates to isothiocyanate containing products from Brassicaceae material produced by such methods.

Figure 1:
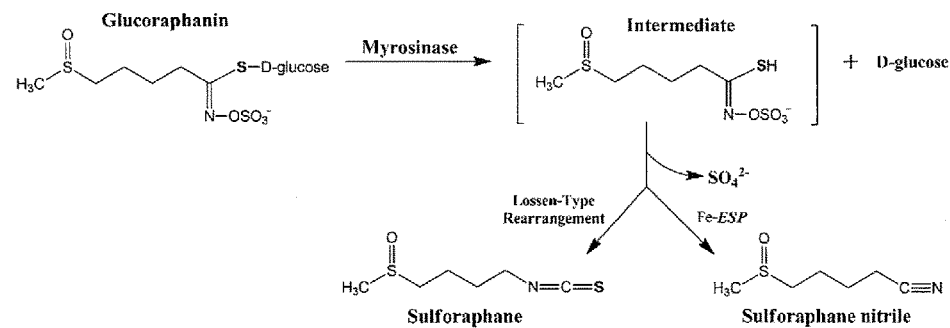
Figure 1:
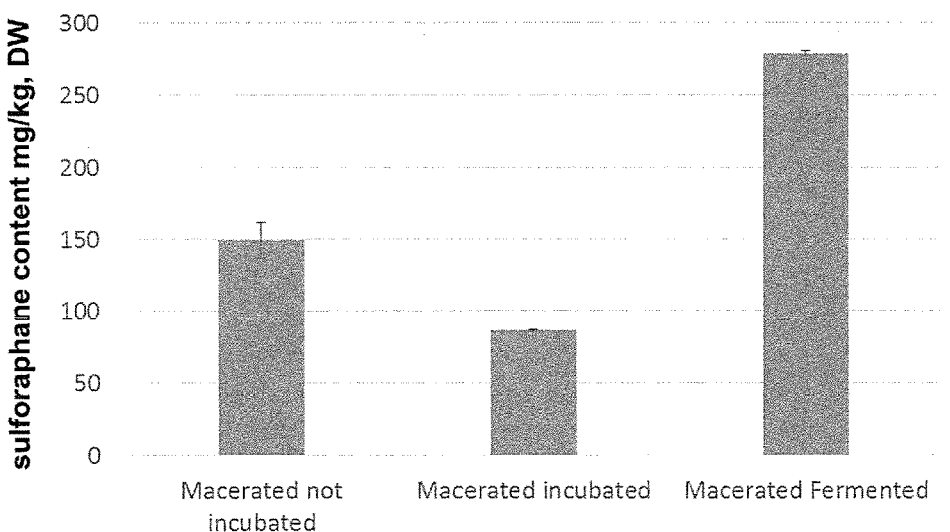
Figure 1:
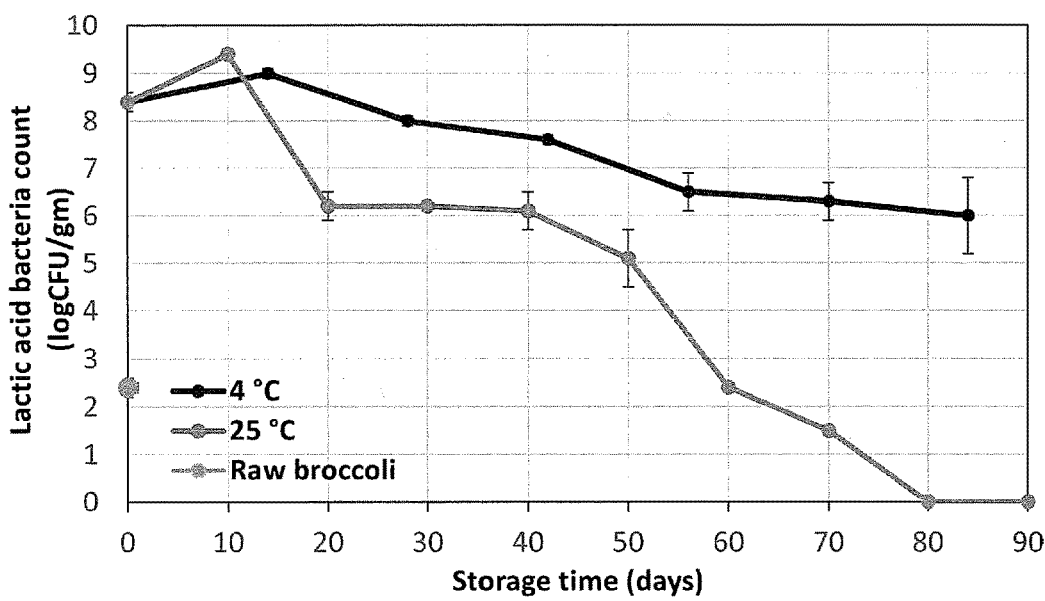

15 Claims, 13 Drawing Sheets
Specification includes a Sequence Listing.

(56) References Cited

OTHER PUBLICATIONS

International Type Search Report from Australian Patent Office issued in corresponding National Application No. 2017903944 mailed on Aug. 10, 2018.
International Type Search Report from Australian Patent Office issued in corresponding National Application No. 2017903944 mailed on Aug. 24, 2018.
Agerbirk et al., "*Glucosinolate structures in evolution*", 77: 16-45, 2012.
Alvarez-Sieiro et al., "Bacteriocins of lactic acid bacteria: extending the family", *Appl Microbiol Biotechnol*, 100: 2939-2951, 2016.
Axelsson et al., "Sulforaphane reduces hepatic glucose production and improves glucose control in patients with type 2 diabetes", *Sci. Transl. Med.*, 9, 2017.
Congxi et al., "Effects of industrial pre-freezing processing and freezing handling on glucosinolates and antioxidant attributes in broccoli florets", *Food Chemistry*, 210:451-456, 2016.
Capuano et al., "Food as Pharma? The Case of Glucosinolates", *Current Pharmaceutical Design*, 23(19): 2697-2721, 2017.
Chen et al., "Isolation and characterization of lactic acid bacteria from Yan-tsai-shin (fermented broccoli stems), a traditional fermented food in Taiwan", Journal of Applied Microbiology, 115:125-132, 2013.
Chuat et al., "Pulsed-Field Gel Electrophoresis for Leuconostoc mesenteroides and L. pseudomesenteroides" *Methods in Molecular Biology*, vol. 1301, 2015.
Dosz et al., "Commercially produced frozen broccoli lacks the ability to form sulforaphane", *Journal of Functional Foods*, 5:987-990, 2013.
Filannino et al., "Metabolism of phenolic compounds by *Lactobacillus* spp during fermentation of cherry juice and broccoli puree", *Food Microbiology*, 46:272-279, 2015.
Fiorda et al., "Microbiological, biochemical, and functional aspects of sugary kefir fermentation—A review", *Food Microbiology*, 66:86-95, 2017.
Guzmán-López et al., "Microcultures of lactic acid bacteria: characterization and selection of strains, optimization of nutrients and gallic acid concentration", *J Ind Microbiol Biotechnol*, 36:11-20, 2009.
Halkier et al., "Biology and Biochemistry of Glucosinolates", *Annu. Rev. Plant. Biol.*, 57:303-333, 2006.
Huang et al., "High-Throughput Assay of Oxygen Radical Absorbance Capacity (ORAC) Using a Multichannel Liquid Hangling System Coupled with a Microplate Fluorescence Reader in 96-Well Format". *J. Agric. Food Chem.*, 50:4437-4444.
International Preliminary Report on Patentability issued in corresponding International application No. PCT/AU2018/051063 mailed on Mar. 31, 2020.
International Search Report and Written Opinion of the International Searching Authority issued in corresponding International application No. PCT/AU2018/051063 mailed on Dec. 4, 2018.

Jaiswal et al., "Fermentation-assisted Extraction of Isothiocyanates from *Brassica* Vegetable Using Box-Behnken Experimental Design", *Foods*, 5 (75), 2016.
Jeffery et al., "Physiological effects of broccoli consumption", *Phytochem Rev.*, 8:283-298, 2009.
Kim et al., "Current potential Health Benefits of Sulforaphane", *EXCLI Journal*, 15:571-577, 2016.
Latté et al., "Health benefits and possible risks of broccoli—An overview", *Food and Chemical Toxicology*, 49:3287-3309, 2011.
Li et al., Development and verification of sulforaphane extraction method in cabbage (*Brassica oleracea* L. var. *capitata*) and broccoli (*Brassica oleracea* L. var. *italica* Planch.), *Journal of Medicinal Plants Research*, 6(33):4796-4803, 2012.
Mokhtari et al., "The role of Sulforaphane in cancer chemoprevention and health benefits: a mini-review", *J Cell Commun. Signal.*, 12:91-101, 2018.
Palani et al., "Influence of fermentation on glucosinolates and glucobrassicin degradation products in sauerkraut", *Food Chemistry*, 190:755-762, 2016.
Peñas et al., "Influence of fermentation conditions of *Brassica oleracea* L. var. *capitata* on the volatile glucosinolate hydrolysis compounds of sauerkrauts"., *LWT—Food Science and Technology*, 48(1):16023, 2012.
Singleton et al., "Colorimetry of Total Phenolics with Phosphomolybdic-Phosphotungstic Acid Reagents", *Am J Enol Vitic*, 16:144-158, 1965.
Tolonen et al., "Plant-Derived Biomolecules in Fermented Cabbage", *J. Agric. Food Chem.*, 50:6798-6803, 2002.
Van Eylen et al., "Kinetics of the Stability of Broccoli (*Brassica oleracea* Cv. *italica*) Myrosinase and Isothiocyanates in Broccoli Juice during Pressure/Temperature Treatments", *J. Agric. Food Chem.*, 55:2163-2170, 2007.
Verkerk et al., "Glucosinolates in *Brassica* vegetables: The influence of the food supply chain on intake, bioavailability and human health", *Mol. Nutr. Food Res.*, 53:S219-S265, 2009.
Xia et al., "Using MetaboAnalyst 3.0 for comprehensive metabolomics data analysis", *Curr. Protoc. Bioinform.*, 55:14.10.1-14.10.01, 2016.
Yang et al., "Fermentation Characteristics and anti-Helicobacter pylori Activity of Aqueous Broccoli Fermented by Lactobacillus planatarum MG208", *J Appl Biol Chem*, 58(1):89-95, 2015.
Extended European Search Report from the European Patent Office issued in corresponding U.S. Appl. No. 18/861,205, mailed May 21, 2017.
Matusheski et al., "Heating decreases epithiospecifier protein activity and increases sulforaphane formation in broccoli", *Phytochemistry*, 65:1273-1281, 2004.
Notice of Reasons for Rejection from the Japanese Patent Office issued in corresponding Patent Application No. 2020-517996, dated Jun. 28, 2022.
Ye et al., "Fermentation-based biotransformation of glucosinolates, phenolics and sugars in retorted broccoli puree by lactic acid bacteria", *Food Chemistry*, 286: 616-623, 2019.

\* cited by examiner

A

B

C

A

B

SEQUENCE LISTING

<160> NUMBER OF SEQ ID NOS: 56

<210> SEQ ID NO 1
<211> LENGTH: 22
<212> TYPE: DNA
<213> ORGANISM: Lactobacillus plantarum

<400> SEQUENCE: 1
tattaatggc tcgcgtcatt aa                                           22

<210> SEQ ID NO 2
<211> LENGTH: 23
<212> TYPE: DNA
<213> ORGANISM: Lactobacillus plantarum

<400> SEQUENCE: 2
cgctcaacca gattagtacc cag                                            23

<210> SEQ ID NO 3
<211> LENGTH: 10
<212> TYPE: DNA
<213> ORGANISM: Lactobacillus plantarum

<400> SEQUENCE: 3
gtttttttg                                                            10

<210> SEQ ID NO 4
<211> LENGTH: 11
<212> TYPE: DNA
<213> ORGANISM: Lactobacillus plantarum

<400> SEQUENCE: 4 gtttttttt g                                                          11

<210> SEQ ID NO 5
<211> LENGTH: 23
<212> TYPE: DNA
<213> ORGANISM: Lactobacillus plantarum

<400> SEQUENCE: 5
caccaccagg ccgattgtgg cga                                            23

<210> SEQ ID NO 6
<211> LENGTH: 34
<212> TYPE: DNA
<213> ORGANISM: Lactobacillus plantarum

<400> SEQUENCE: 6
cttgccgaaa ttcgacaaac aaccctcgga ttgt                                34

<210> SEQ ID NO 7
<211> LENGTH: 70
<212> TYPE: DNA
<213> ORGANISM: Lactobacillus plantarum

<400> SEQUENCE: 7
tataaaaaaa gcgaccccg ttcattaacg gtgccgctca cagatcatta ttagtgaaaa     60
tcacccggca                                                           70

<210> SEQ ID NO 8
<211> LENGTH: 14
<212> TYPE: DNA
<213> ORGANISM: Leuconostoc mesenteroides

<400> SEQUENCE: 8
ggtatgggat ggga                                                      14

<210> SEQ ID NO 9
<211> LENGTH: 11
<212> TYPE: DNA
<213> ORGANISM: Leuconostoc mesenteroides

<400> SEQUENCE: 9

```
gtttttttttt a                                                      11

<210> SEQ ID NO 10
<211> LENGTH: 10
<212> TYPE: DNA
<213> ORGANISM: Leuconostoc mesenteroides

<400> SEQUENCE: 10
gtttttttc                                                          10

<210> SEQ ID NO 11
<211> LENGTH: 21
<212> TYPE: DNA
<213> ORGANISM: Leuconostoc mesenteroides

<400> SEQUENCE: 11
tagctgcaag tgctgcaagt g                                            21

<210> SEQ ID NO 12
<211> LENGTH: 12
<212> TYPE: DNA
<213> ORGANISM: Leuconostoc mesenteroides

<400> SEQUENCE: 12
cagctgcaag tg                                                      12

<210> SEQ ID NO 13
<211> LENGTH: 10
<212> TYPE: DNA
<213> ORGANISM: Leuconostoc mesenteroides

<400> SEQUENCE: 13
cagattaacg                                                         10

<210> SEQ ID NO 14
<211> LENGTH: 10
<212> TYPE: DNA
<213> ORGANISM: Leuconostoc mesenteroides

<400> SEQUENCE: 14
aaaatcaaaa                                                         10

<210> SEQ ID NO 15
<211> LENGTH: 14
<212> TYPE: DNA
<213> ORGANISM: Leuconostoc mesenteroides

<400> SEQUENCE: 15
cgaaacgctc attc                                                    14

<210> SEQ ID NO 16
<211> LENGTH: 14
<212> TYPE: DNA
<213> ORGANISM: Leuconostoc mesenteroides

<400> SEQUENCE: 16
tgagacacta atta                                                    14

<210> SEQ ID NO 17
<211> LENGTH: 12
<212> TYPE: DNA
<213> ORGANISM: Leuconostoc mesenteroides
```

-continued

```
<400> SEQUENCE: 17
gtttcagaaa aa                                                   12

<210> SEQ ID NO 18
<211> LENGTH: 12
<212> TYPE: DNA
<213> ORGANISM: Leuconostoc mesenteroides

<400> SEQUENCE: 18
atgtcggaag ag                                                   12

<210> SEQ ID NO 19
<211> LENGTH: 17
<212> TYPE: DNA
<213> ORGANISM: Leuconostoc mesenteroides

<400> SEQUENCE: 19
atttaagttc agtcaca                                              17

<210> SEQ ID NO 20
<211> LENGTH: 17
<212> TYPE: DNA
<213> ORGANISM: Leuconostoc mesenteroides

<400> SEQUENCE: 20
ctacaatatc acttccc                                              17

<210> SEQ ID NO 21
<211> LENGTH: 12
<212> TYPE: DNA
<213> ORGANISM: Leuconostoc mesenteroides

<400> SEQUENCE: 21
taaagcctct tg                                                   12

<210> SEQ ID NO 22
<211> LENGTH: 12
<212> TYPE: DNA
<213> ORGANISM: Leuconostoc mesenteroides

<400> SEQUENCE: 22
cagagcagct tc                                                   12

<210> SEQ ID NO 23
<211> LENGTH: 20
<212> TYPE: DNA
<213> ORGANISM: Leuconostoc mesenteroides

<400> SEQUENCE: 23
tggctcctct atttgtcttt                                           20

<210> SEQ ID NO 24
<211> LENGTH: 20
<212> TYPE: DNA
<213> ORGANISM: Leuconostoc mesenteroides

<400> SEQUENCE: 24
aggcaccttt agtcgtttta                                           20

<210> SEQ ID NO 25
<211> LENGTH: 10
<212> TYPE: DNA
<213> ORGANISM: Leuconostoc mesenteroides
```

```
<400> SEQUENCE: 25
agctgtgacc                                                              10

<210> SEQ ID NO 26
<211> LENGTH: 10
<212> TYPE: DNA
<213> ORGANISM: Leuconostoc mesenteroides

<400> SEQUENCE: 26
ggcagtcact                                                              10

<210> SEQ ID NO 27
<211> LENGTH: 10
<212> TYPE: DNA
<213> ORGANISM: Leuconostoc mesenteroides

<400> SEQUENCE: 27
aaccaatcct                                                              10

<210> SEQ ID NO 28
<211> LENGTH: 10
<212> TYPE: DNA
<213> ORGANISM: Leuconostoc mesenteroides

<400> SEQUENCE: 28
tacaaaacca                                                              10

<210> SEQ ID NO 29
<211> LENGTH: 15
<212> TYPE: DNA
<213> ORGANISM: Leuconostoc mesenteroides

<400> SEQUENCE: 29
caaaaaaaaa aaaac                                                        15

<210> SEQ ID NO 30
<211> LENGTH: 14
<212> TYPE: DNA
<213> ORGANISM: Leuconostoc mesenteroides

<400> SEQUENCE: 30
caaaaaaaac aaac                                                         14

<210> SEQ ID NO 31
<211> LENGTH: 13
<212> TYPE: DNA
<213> ORGANISM: Leuconostoc mesenteroides

<400> SEQUENCE: 31
tgtgttcaaa gat                                                          13

<210> SEQ ID NO 32
<211> LENGTH: 13
<212> TYPE: DNA
<213> ORGANISM: Leuconostoc mesenteroides

<400> SEQUENCE: 32
catatttaga gac                                                          13

<210> SEQ ID NO 33
<211> LENGTH: 12
<212> TYPE: DNA
```

```
<213> ORGANISM: Leuconostoc mesenteroides

<400> SEQUENCE: 33
aggaatcgtt ca                                                        12

<210> SEQ ID NO 34
<211> LENGTH: 13
<212> TYPE: DNA
<213> ORGANISM: Leuconostoc mesenteroides

<400> SEQUENCE: 34
atagattggc tcg                                                       13

<210> SEQ ID NO 35
<211> LENGTH: 13
<212> TYPE: DNA
<213> ORGANISM: Leuconostoc mesenteroides

<400> SEQUENCE: 35
ttttaaaccg tca                                                       13

<210> SEQ ID NO 36
<211> LENGTH: 13
<212> TYPE: DNA
<213> ORGANISM: Leuconostoc mesenteroides

<400> SEQUENCE: 36
cttcaaatca tcg                                                       13

<210> SEQ ID NO 37
<211> LENGTH: 10
<212> TYPE: DNA
<213> ORGANISM: Leuconostoc mesenteroides

<400> SEQUENCE: 37
gaaagacgct                                                           10

<210> SEQ ID NO 38
<211> LENGTH: 10
<212> TYPE: DNA
<213> ORGANISM: Leuconostoc mesenteroides

<400> SEQUENCE: 38
aaaggatgcc                                                           10

<210> SEQ ID NO 39
<211> LENGTH: 13
<212> TYPE: DNA
<213> ORGANISM: Leuconostoc mesenteroides

<400> SEQUENCE: 39
ggccgctagc atg                                                       13

<210> SEQ ID NO 40
<211> LENGTH: 13
<212> TYPE: DNA
<213> ORGANISM: Leuconostoc mesenteroides

<400> SEQUENCE: 40
tgcagccaac ata                                                       13

<210> SEQ ID NO 41
<211> LENGTH: 17
```

```
<212> TYPE: DNA
<213> ORGANISM: Leuconostoc mesenteroides

<400> SEQUENCE: 41
acccgatggg ttgtatt                                                    17

<210> SEQ ID NO 42
<211> LENGTH: 15
<212> TYPE: DNA
<213> ORGANISM: Leuconostoc mesenteroides

<400> SEQUENCE: 42
gccactaggc tgcat                                                      15

<210> SEQ ID NO 43
<211> LENGTH: 28
<212> TYPE: DNA
<213> ORGANISM: Leuconostoc mesenteroides

<400> SEQUENCE: 43
ggctgcaaac gctgcacgca ggcgcagc                                        28

<210> SEQ ID NO 44
<211> LENGTH: 28
<212> TYPE: DNA
<213> ORGANISM: Leuconostoc mesenteroides

<400> SEQUENCE: 44
agcagcgaaa gcagcgcgta aacgaagt                                        28

<210> SEQ ID NO 45
<211> LENGTH: 22
<212> TYPE: DNA
<213> ORGANISM: Leuconostoc mesenteroides

<400> SEQUENCE: 45
ctggggtatc aaaacggtta ca                                              22

<210> SEQ ID NO 46
<211> LENGTH: 22
<212> TYPE: DNA
<213> ORGANISM: Leuconostoc mesenteroides

<400> SEQUENCE: 46
ttgtggaatt aatactgtca ct                                              22

<210> SEQ ID NO 47
<211> LENGTH: 15
<212> TYPE: DNA
<213> ORGANISM: Leuconostoc mesenteroides

<400> SEQUENCE: 47
attacctttg ataac                                                      15

<210> SEQ ID NO 48
<211> LENGTH: 15
<212> TYPE: DNA
<213> ORGANISM: Leuconostoc mesenteroides

<400> SEQUENCE: 48
gttatcaaag gtaat                                                      15

<210> SEQ ID NO 49
```

-continued

```
<211> LENGTH: 10
<212> TYPE: DNA
<213> ORGANISM: Leuconostoc mesenteroides

<400> SEQUENCE: 49
caatgaaccg                                                              10

<210> SEQ ID NO 50
<211> LENGTH: 10
<212> TYPE: DNA
<213> ORGANISM: Leuconostoc mesenteroides

<400> SEQUENCE: 50
tagagagcca                                                              10

<210> SEQ ID NO 51
<211> LENGTH: 10
<212> TYPE: DNA
<213> ORGANISM: Leuconostoc mesenteroides

<400> SEQUENCE: 51
tgtcacttga                                                              10

<210> SEQ ID NO 52
<211> LENGTH: 10
<212> TYPE: DNA
<213> ORGANISM: Leuconostoc mesenteroides

<400> SEQUENCE: 52
agttacctgg                                                              10

<210> SEQ ID NO 53
<211> LENGTH: 12
<212> TYPE: DNA
<213> ORGANISM: Leuconostoc mesenteroides

<400> SEQUENCE: 53
tgtgttaaat ac                                                           12

<210> SEQ ID NO 54
<211> LENGTH: 12
<212> TYPE: DNA
<213> ORGANISM: Leuconostoc mesenteroides

<400> SEQUENCE: 54
agtgctatat tt                                                           12

<210> SEQ ID NO 55
<211> LENGTH: 14
<212> TYPE: DNA
<213> ORGANISM: Leuconostoc mesenteroides

<400> SEQUENCE: 55
gaccccgttc aggc                                                         14

<210> SEQ ID NO 56
<211> LENGTH: 14
<212> TYPE: DNA
<213> ORGANISM: Leuconostoc mesenteroides

<400> SEQUENCE: 56
atcctcgctc cggt                                                         14
```

ISOTHIOCYANATE CONTAINING *BRASSICACEAE* PRODUCTS AND METHOD OF PREPARATION THEREOF

CROSS-REFERENCE TO RELATED APPLICATIONS

This application is a national phase application under 35 U.S.C. § 371 of International Application No. PCT/AU2018/051063, filed 27 Sep. 2018, which claims priority to Australian Patent Application No. 2017903944, filed 28 Sep. 2017. The entire contents of each of the above-referenced disclosures is specifically incorporated by reference herein without disclaimer.

FIELD OF THE INVENTION

The present invention relates to methods for producing isothiocyanate containing products from Brassicaceae material and lactic acid bacteria for use in such methods. The present invention also relates to isothiocyanate containing products from Brassicaceae material produced by such methods.

BACKGROUND OF THE INVENTION

Brassicaceae family members are rich in glucosinolates which can be converted by the enzyme myrosinase to isothiocyanates which have been noted to have beneficial effects on some types of cancer (Moktari et al., 2017; Capuano et al., 2017; Kim and Park, 2016). Sulforaphane, for example, has been found to reduce hepatic glucose production and improve glucose control in obese patients with type 2 diabetes (Axelsson et al., 2017). However, many Brassicaceae family members are highly perishable after harvest with the quality and quantity of nutrients declining rapidly if the product is not stored well.

Brassicaceae are often processed to increase the shelf life which can result in the loss of nutrients. The main methods to obtain a longer shelf life include thermal processing, freezing, modified and controlled atmosphere storage and the addition of chemical preservatives which also would bring undesirable changes in chemical composition.

These processes can result in the loss of glucosinolates or reduce the ability of the enzyme myrosinase to convert glucosinolates to isothiocyanates. For example, conventional broccoli processing/preservation involves blanching prior to freezing to inactivate quality degrading enzymes such as lipoxygenase. Peroxidase inactivation is commonly used as an indicator of the adequacy of blanching. The condition for inactivation of peroxidase leads to the inactivation of myrosinase and thus the resulting product is devoid of isothiocyanates (Dosz and Jeffery, 2013).

Accordingly, there remains a need for improved methods for producing Brassicaceae products comprising phytonutrients such as isothiocyanates.

SUMMARY OF THE INVENTION

The present inventors have developed methods for preparing isothiocyanate containing products from Brassicaceae material.

In an aspect, the present invention provides a method of preparing an isothiocyanate containing product from Brassicaceae material comprising:
  i) pre-treating the Brassicaceae material to improve the access of myrosinase to a glucosinolate;
  ii) fermenting the material obtained by step i) with lactic acid bacteria to form the isothiocyanate containing product.

In an embodiment, pre-treating comprises one or more of the following:
  i) heating;
  ii) macerating;
  iii) microwaving;
  iv) exposure to high frequency sound waves (ultrasound); or
  v) pulse electric field processing
wherein the temperature of the Brassicaceae material does not exceed about 75° C. during pre-treating.

In an embodiment, pre-treating reduces epithiospecifier protein (ESP) activity while maintaining endogenous myrosinase activity.

In an embodiment, pre-treating comprises heating and macerating the Brassicaceae material and wherein the temperature of the Brassicaceae material does not exceed about 75° C. during pre-treating. In an embodiment, heating occurs before macerating or wherein heating and macerating occur at the same time. In an embodiment, pre-treating comprises heating the Brassicaceae material to a temperature of about 50° C. to about 70° C. followed by maceration. In an embodiment, the Brassicaceae material is macerated so that at least about 80% of the Brassicaceae material is of a size of about 2 mm or less. In an embodiment, the Brassicaceae material is heated in a sealed package.

In an embodiment, the isothiocyanate containing product comprises at least about 10 times more isothiocyanate than macerated Brassicaceae material.

In an embodiment, the isothiocyanate containing product comprises at least about 12 times more isothiocyanate than macerated Brassicaceae material.

In an embodiment, the isothiocyanate containing product comprises at least about 14 times more isothiocyanate than macerated Brassicaceae material.

In an embodiment, the isothiocyanate containing product comprises at least about 16 times more isothiocyanate than macerated Brassicaceae material.

In an embodiment, the isothiocyanate containing product comprises at least about 2 times the expected maximum yield of isothiocyanate based on the extractable glucosinolate content.

In an embodiment, lactic acid bacteria was isolated from a broccoli and/or the lactic acid bacteria lacks myrosinase activity.

In an aspect, the present invention provides a method of preparing a isothiocyanate containing product from Brassicaceae material comprising:
  i) pre-treating the Brassicaceae material to improve the access of myrosinase to a glucosinolate; and
  ii) acidifying the material obtained by step i) forming the isothiocyanate containing product.

In an aspect, the present invention provides a method of preparing an isothiocyanate containing product from broccoli material comprising fermenting the material with lactic acid bacteria *Leuconostoc mesenteroides* and/or *Lactobacillus plantarum* to form the isothiocyanate containing product, wherein the method optionally comprises pre-treating the broccoli material to improve the access of myrosinase to a glucosinolate.

In an aspect, the present invention provides a method of preparing an isothiocyanate containing product from a Brassicaceae material comprising fermenting the material with lactic acid bacteria *Leuconostoc mesenteroides* and/or *Lactobacillus plantarum* isolated from broccoli to form the isothiocyanate containing product, wherein the method optionally comprises pre-treating the Brassicaceae material to improve the access of myrosinase to a glucosinolate.

In an aspect, the present invention provides an isolated strain of lactic acid bacteria selected from:
i) BF1 deposited under V17/021729 on 25 Sep. 2017 at the National Measurement Institute Australia; and
ii) BF2 deposited under V17/021730 on 25 Sep. 2017 at the National Measurement Institute Australia.

In an aspect, the present invention provides an isolated strain of lactic acid bacteria selected from:
i) BF1 deposited under V17/021729 on 25 Sep. 2017 at the National Measurement Institute Australia;
ii) BF2 deposited under V17/021730 on 25 Sep. 2017 at the National Measurement Institute Australia;
iii) B1 deposited under V17/021731 on 25 Sep. 2017 at the National Measurement Institute Australia;
iv) B2 deposited under V17/021732 on 25 Sep. 2017 at the National Measurement Institute Australia;
v) B3 deposited under V17/021733 on 25 Sep. 2017 at the National Measurement Institute Australia;
vi) B4 deposited under V17/021734 on 25 Sep. 2017 at the National Measurement Institute Australia; and
vii) B5 deposited under V17/021735 on 25 Sep. 2017 at the National Measurement Institute Australia.

In an aspect, the present invention provides a starter culture for producing an isothiocyanate containing product or a probiotic comprising lactic acid bacteria selected from one or more or all of:
i) BF1 deposited under V17/021729 on 25 Sep. 2017 at the National Measurement Institute Australia;
ii) BF2 deposited under V17/021730 on 25 Sep. 2017 at the National Measurement Institute Australia;
iii) B1 deposited under V17/021731 on 25 Sep. 2017 at the National Measurement Institute Australia;
iv) B2 deposited under V17/021732 on 25 Sep. 2017 at the National Measurement Institute Australia;
v) B3 deposited under V17/021733 on 25 Sep. 2017 at the National Measurement Institute Australia;
vi) B4 deposited under V17/021734 on 25 Sep. 2017 at the National Measurement Institute Australia; and
vii) B5 deposited under V17/021735 on 25 Sep. 2017 at the National Measurement Institute Australia.

In an embodiment, the starter culture comprises lactic acid bacteria at a concentration of at least about $10^8$ cfu/mL.

In an aspect, the present invention provides a probiotic composition comprising lactic acid bacteria selected from one or more or all of:
i) BF1 deposited under V17/021729 on 25 Sep. 2017 at the National Measurement Institute Australia;
ii) BF2 deposited under V17/021730 on 25 Sep. 2017 at the National Measurement Institute Australia;
iii) B1 deposited under V17/021731 on 25 Sep. 2017 at the National Measurement Institute Australia;
iv) B2 deposited under V17/021732 on 25 Sep. 2017 at the National Measurement Institute Australia;
v) B3 deposited under V17/021733 on 25 Sep. 2017 at the National Measurement Institute Australia;
vi) B4 deposited under V17/021734 on 25 Sep. 2017 at the National Measurement Institute Australia; and
vii) B5 deposited under V17/021735 on 25 Sep. 2017 at the National Measurement Institute Australia.

In an aspect, the present invention provides an isothiocyanate containing product obtained by the method as described herein.

In an aspect, the present invention provides an isothiocyanate containing product obtainable by the method as described herein.

In an aspect, the present invention provides an isothiocyanate containing Brassicaceae product comprising at least about 10 times more isothiocyanate than the macerated Brassicaceae material.

In an aspect, the present invention provides an isothiocyanate containing Brassicaceae product comprising about 10 times to about 16 times more isothiocyanate than the macerated Brassicaceae material.

In an aspect, the present invention provides an isothiocyanate containing Brassicaceae product comprising at least about 2 times the expected maximum yield of isothiocyanate based on the extractable glucosinolate content.

In an aspect, the present invention provides an isothiocyanate containing Brassicaceae product comprising about 2 times to about 4 times the expected maximum yield of isothiocyanate based on the extractable glucosinolate content.

In an aspect, the present invention provides an isothiocyanate containing Brassicaceae product comprising at least 150 mg/kg dw of isothiocyanate.

In an embodiment, the present invention provides an isothiocyanate containing product comprises at least 150 mg/kg dw, at least 200 mg/kg dw, at least 300 mg/kg dw, at least 400 mg/kg dw, or at least 450 mg/kg dw, or at least 500 mg/kg dw, or at least 550 mg/kg dw, or at least 600 mg/kg dw, or at least 650 mg/kg dw, or at least 700 mg/kg dw, or at least 1000 mg/kg dw, or at least 2000 mg/kg dw, or at least 3000 mg/kg dw, or at least 4000 mg/kg dw, or at least 5000 mg/kg dw, or at least 6000 mg/kg dw, or at least 7000 mg/kg dw sulforaphane.

In an embodiment, the isothiocyanate containing product comprises *Leuconostoc mesenteroides* and/or *Lactobacillus plantarum*.

In an embodiment, the isothiocyanate containing product has one or more or all of the following features:
i) is stable for at least 4 weeks, or for at least 8 weeks, or for at least 12 weeks when stored at about 4° C. to about 25° C.;
ii) is resistant to yeast, mould and/or coliform growth for at least 4 weeks, or for at least 8 weeks, or for at least 12 weeks when stored at about 4° C. to about 25° C.; and
iii) comprises at least $10^7$ CFU/g *Leuconostoc mesenteroides* and/or *Lactobacillus plantarum*.

Any embodiment herein shall be taken to apply mutatis mutandis to any other embodiment unless specifically stated otherwise. For instance, as the skilled person would understand examples of lactic acid bacteria outlined above for the methods of the invention equally apply to products of the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANING DRAWINGS

FIG. 1. A) Shows the pathways of hydrolysis of glucoraphanin to sulforaphane and sulforaphane nitrile. B) Shows the effects of maceration and fermentation on sulforaphane content (mg/kg, DW) in broccoli puree. C) Shows the effect of fermentation on lactic acid bacteria count (log CFU/gm) of broccoli puree during storage.

Figure 2:
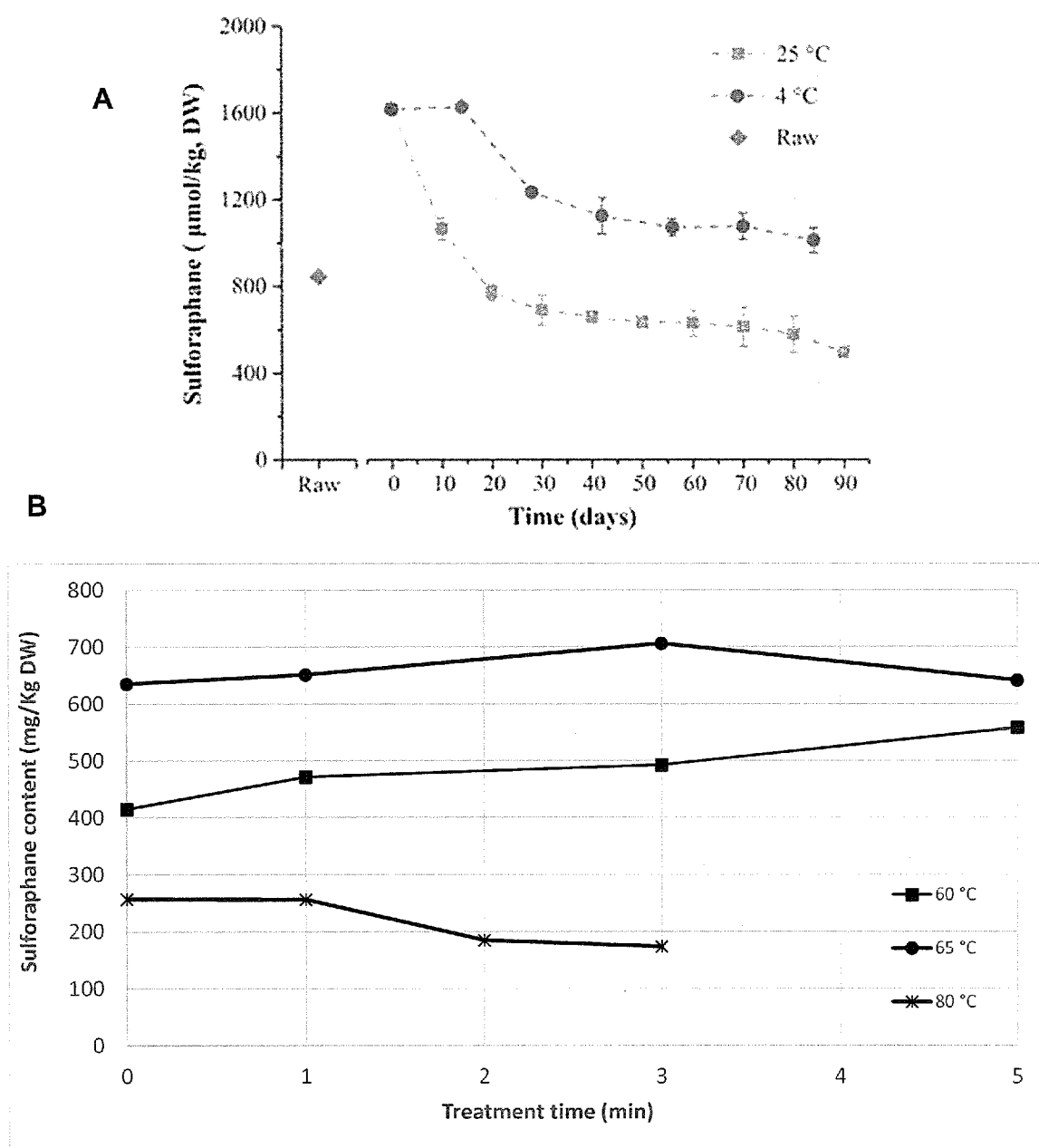

FIG. 2. A) Shows the effects of fermentation on the stability of sulforaphane in broccoli puree stored at 4° C. and 25° C. (RT). B) Effects of heat treatment condition on the conversion of glucoraphanin into sulforaphane in broccoli matrix.

Figure 3:
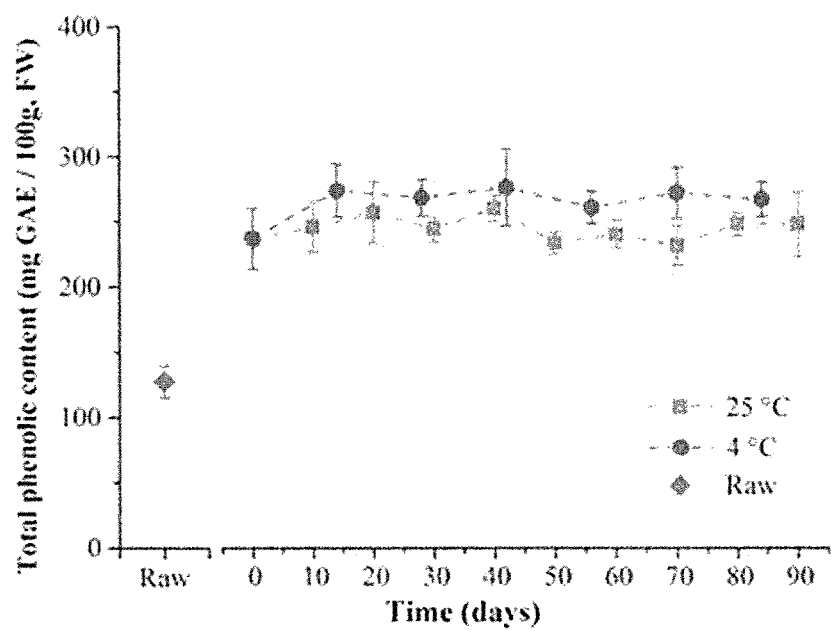
Figure 3:
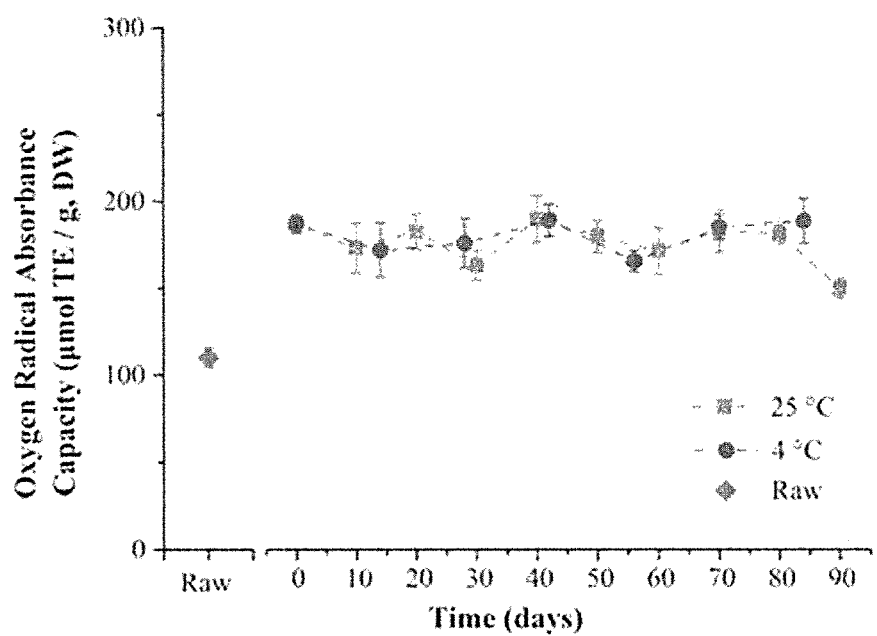

FIG. 3. A) Shows the total phenolic content (mg GAE/100 g DW) of raw broccoli and its changes during fermentation and storage at 25° C. and 4° C., respectively. B) Shows the ORAC (oxygen radical absorbance capacity) antioxidant capacity ($\mu$mol TE/g DW) of raw broccoli and its changes during fermentation and storage at 25° C. and 4° C., respectively.

Figure 4:
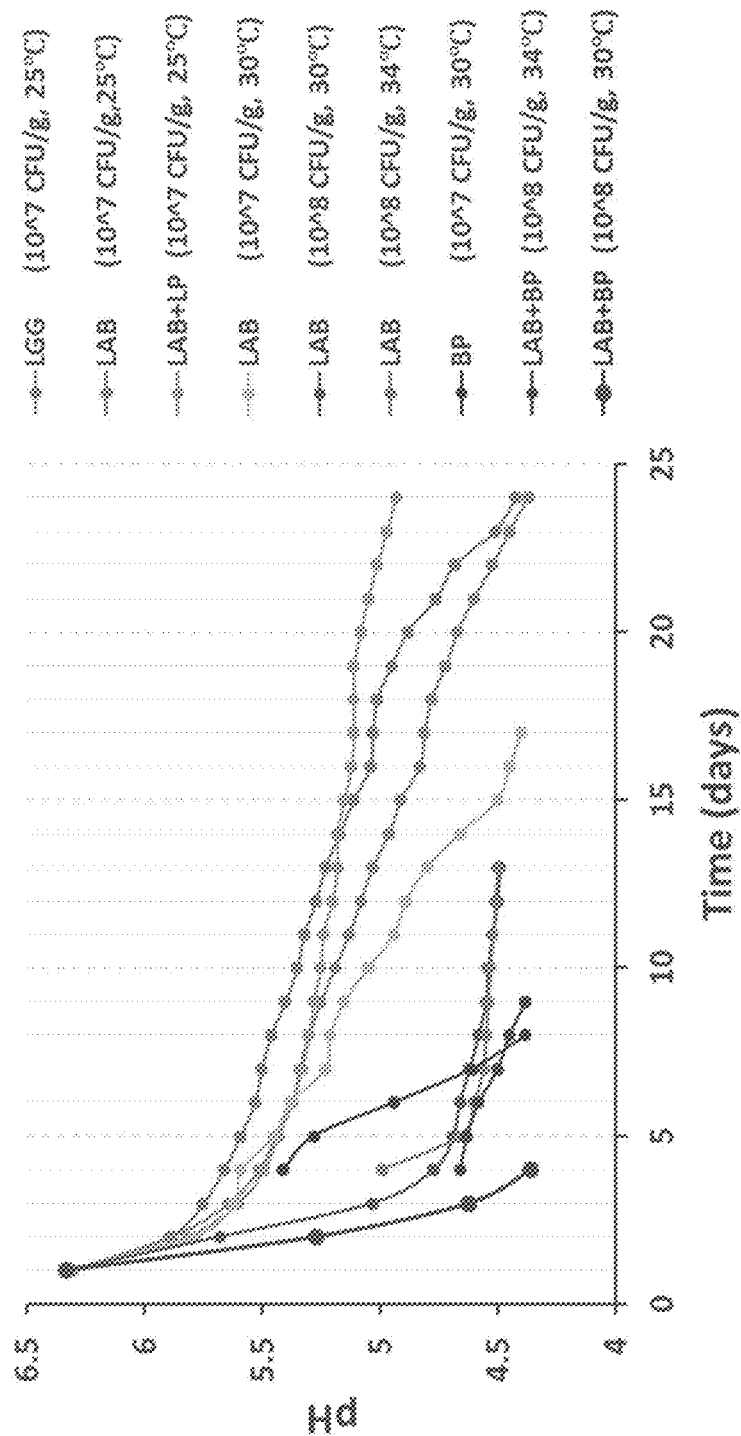

FIG. 4. Shows the fermentation time taken to reach a pH of 4.4 or lower for different combinations of lactic acid bacteria strains.

Figure 5:
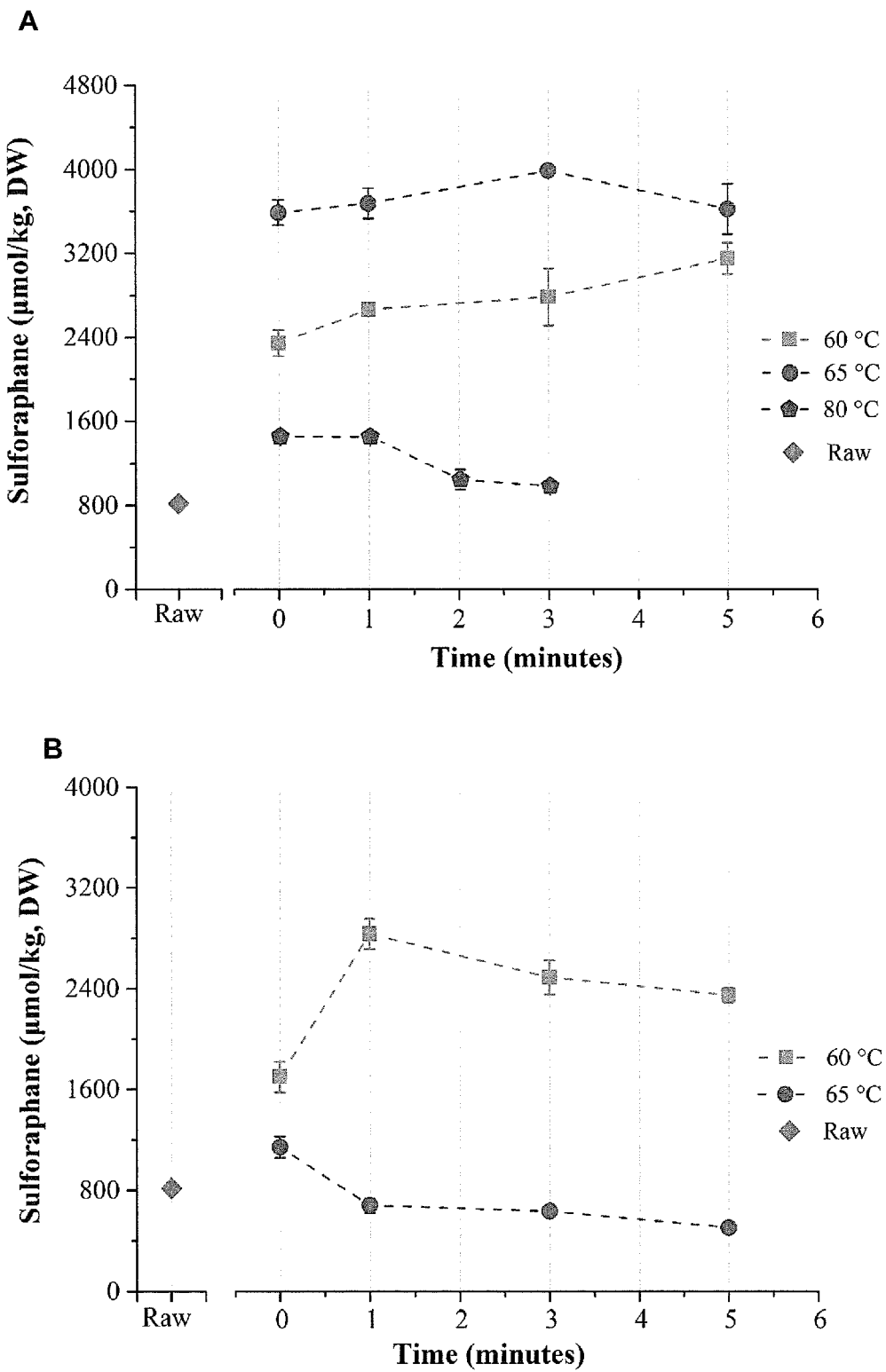

FIG. 5. A) Shows sulforaphane yield ($\mu$mol/kg DW) under different heat treatment conditions of broccoli with a sealed bag. B) Shows sulforaphane yield ($\mu$mol/kg DW) under different heat treatment conditions of broccoli immersed directly in water.

Figure 6:
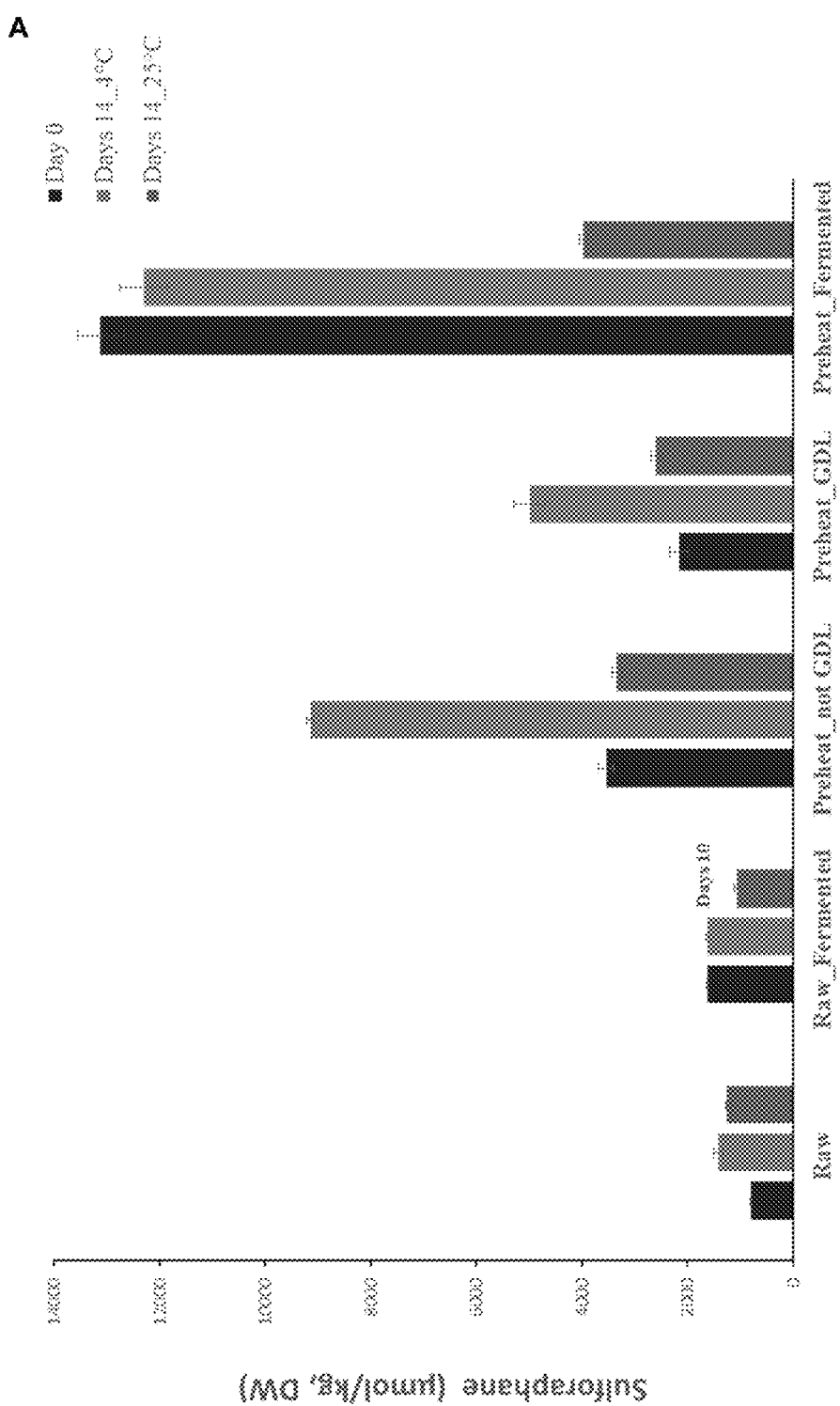

FIG. 6. Shows the comparative effects of the combined effects of maceration, pre-heating and fermentation with just maceration and preheating and maceration, preheating and chemical acidification on sulforaphane yield ($\mu$mol/kg DW) just after processing and during storage at 4° C. and 25° C. Samples were pre-treated at 65° C. for 3 min in sealed packs.

Figure 7:
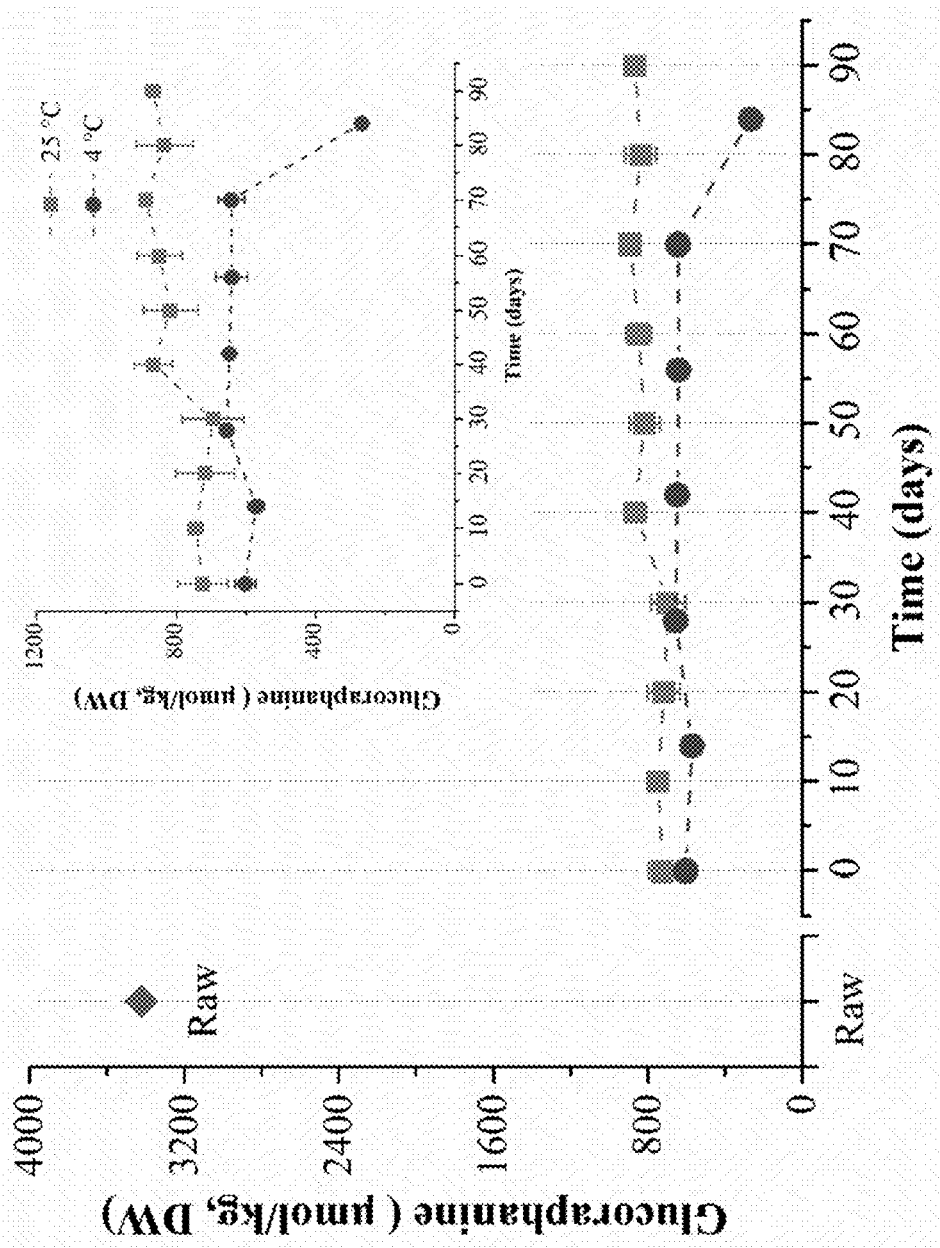

FIG. 7. Shows the effect of fermentation and storage on glucoraphanin content. Glucoraphanin content is reduced in fermented samples stored at 25° C. and 4° C. compared to raw samples.

Figure 8:
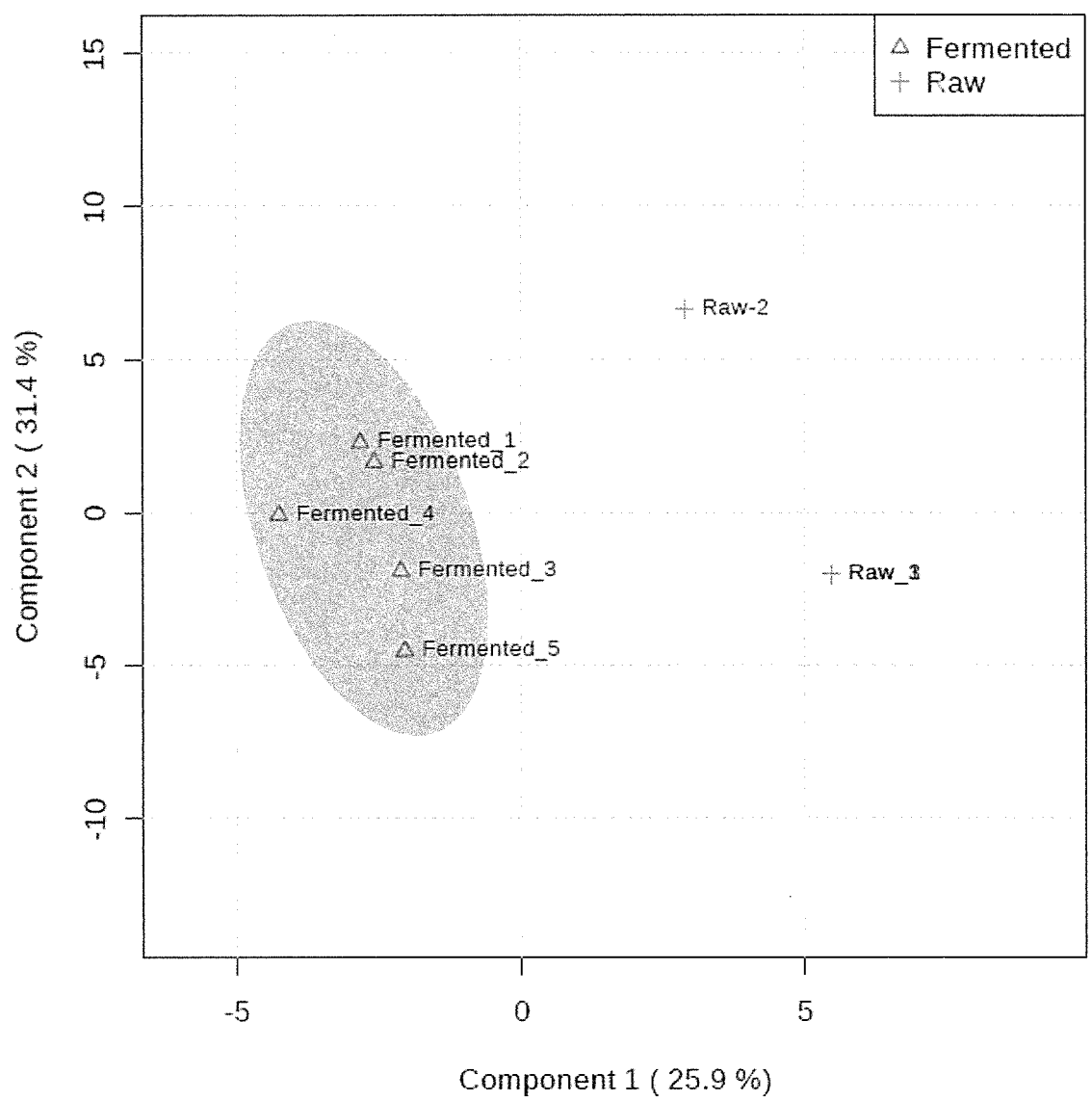

FIG. 8. PLS-DA score plot showing the difference in polyphenolic metabolite profile of raw and fermented broccoli puree.

Figure 9:
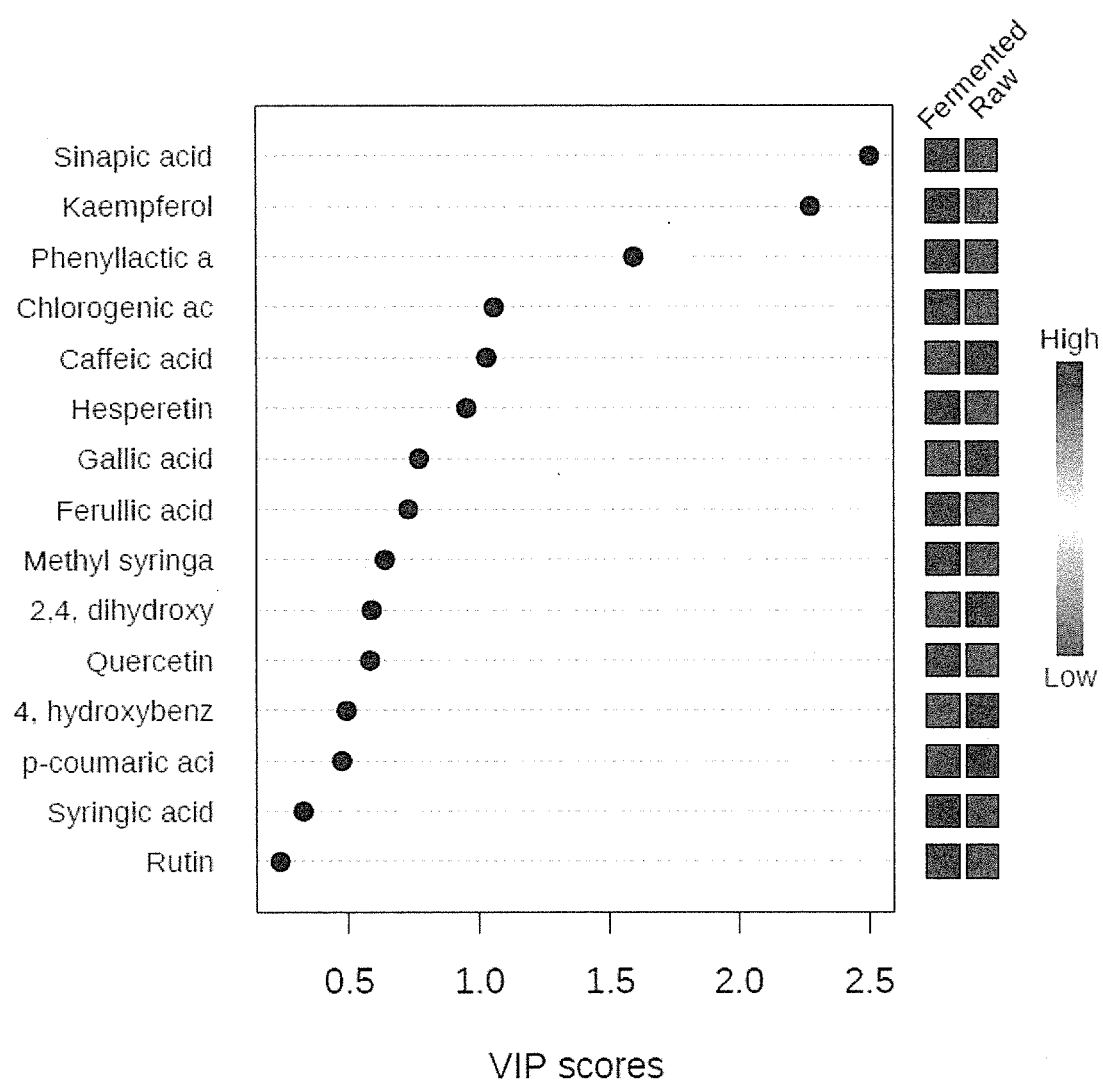

FIG. 9. Important features differentiating fermented and non-fermented samples identified by PLS-DA. The boxes on the right indicate the relative concentration of the respective metabolites in each group.

Figure 10:
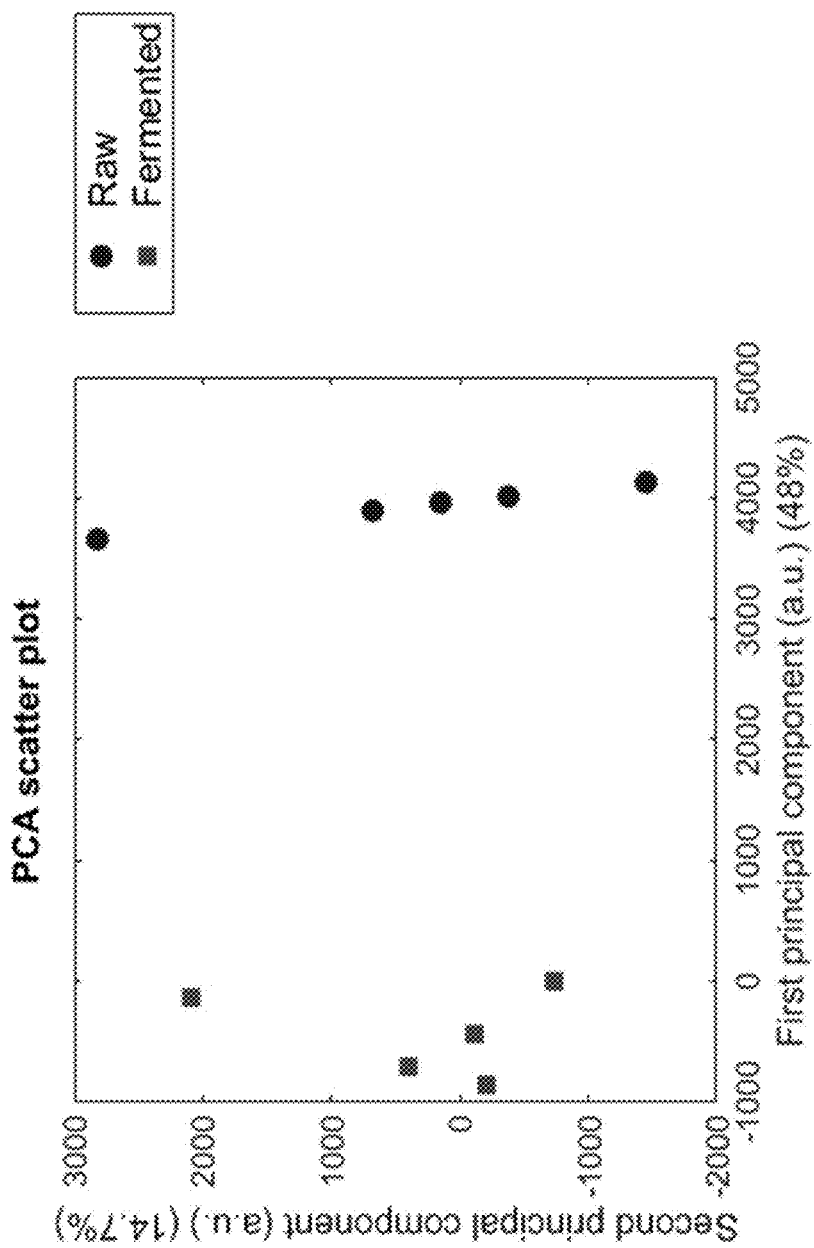

FIG. 10. Shows the effect of lactic acid fermentation on metabolite profile of broccoli puree-based on untargeted LC-MS analysis. It demonstrates that fermentation releases bound phytochemicals such as polyphenolic glycosides and glucosinolates and enhances their bioaccessibility.

Figure 11:
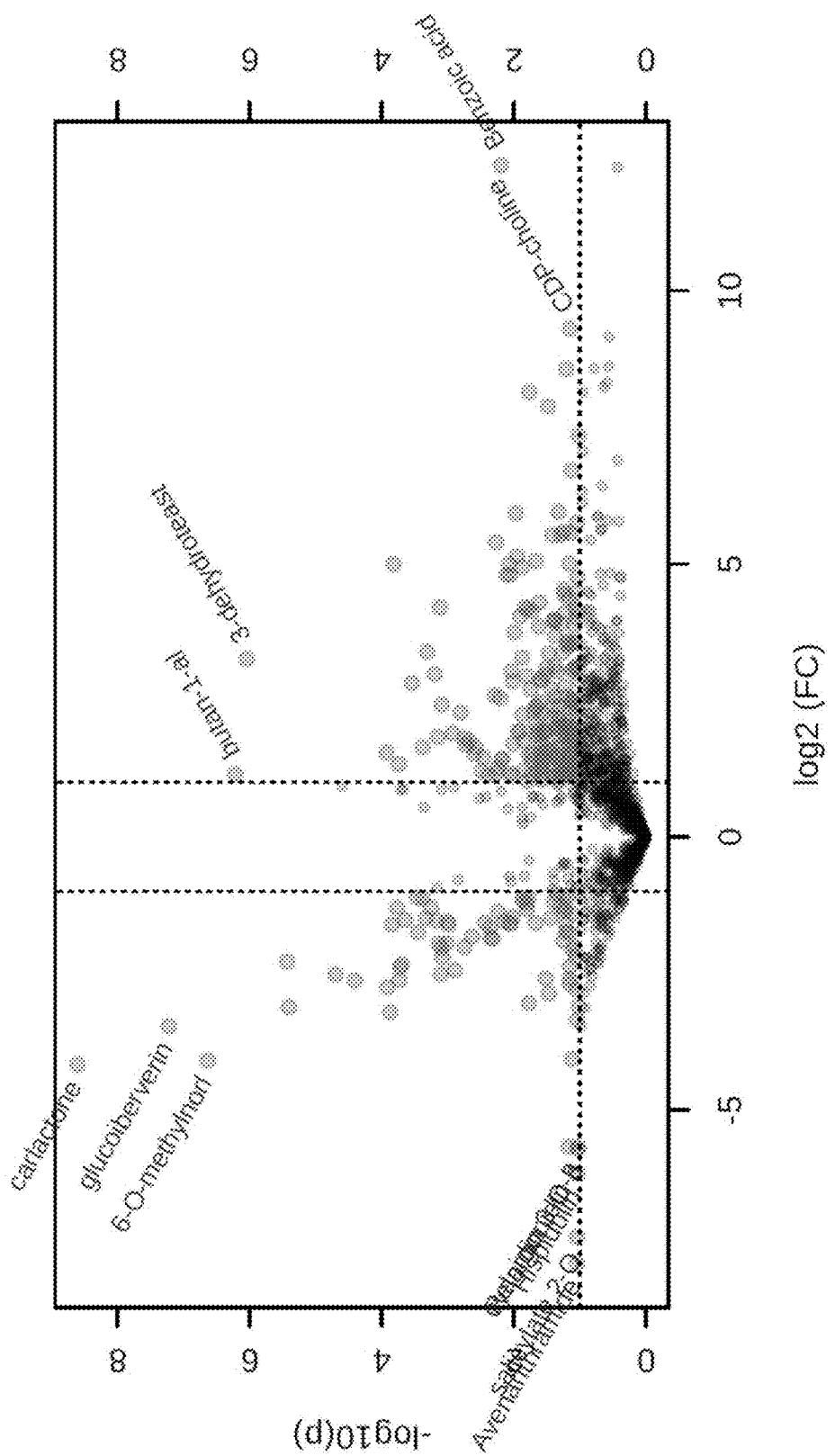

FIG. 11. Shows a volcano plot indicating metabolites with significant ($p<0.05$) fold changes after fermentation based on untargeted LC-MS analysis. The top 50 metabolites with significant fold changes and their individual fold changes are recited in Table 8.

Figure 12:
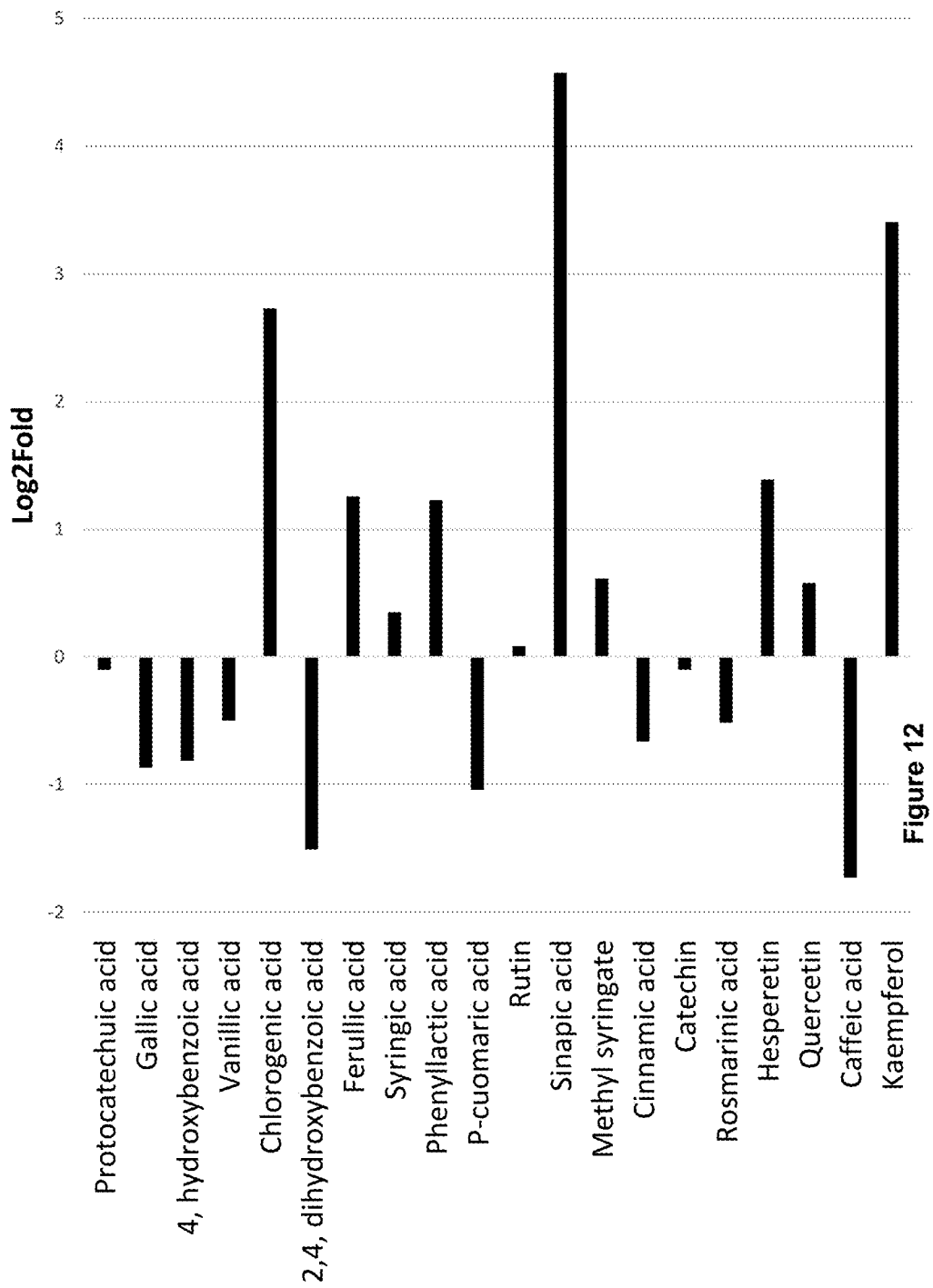

FIG. 12. Shows the effect of lactic acid fermentation on broccoli polyphenols based on targeted LC-MS analysis. A 6.6 fold change is observed in chlorogenic acid (2.4 to 15.8 $\mu$g/mg), a 23.8 fold increase is observed in sinapic acid (3.6 to 86.6 $\mu$g/mg), a 10.5 increase in kaempferol (12.7 to 134.6 $\mu$g/mg) and a 0.48 fold decrease is observed in p-coumaric acid.

Figure 13:
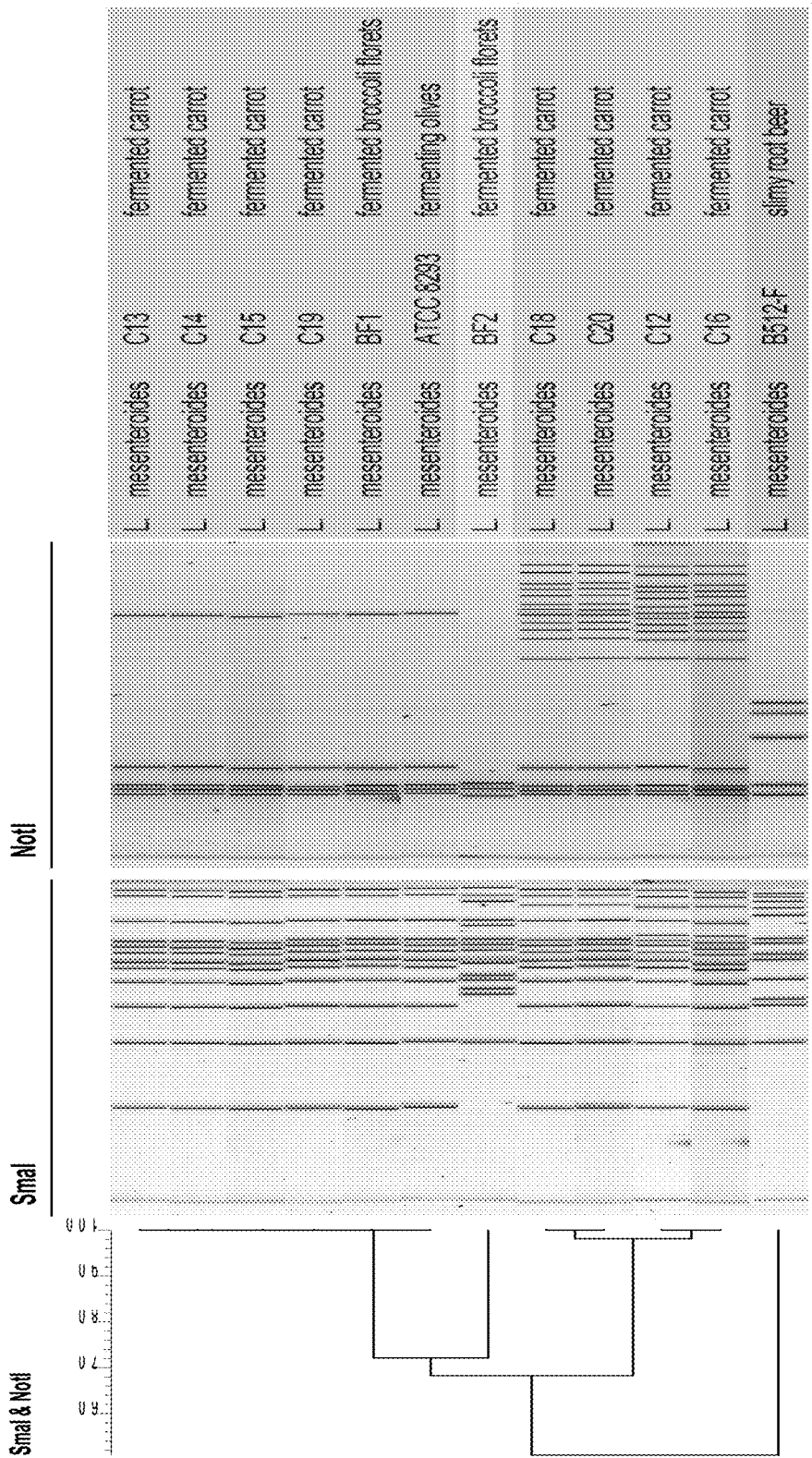

FIG. 13. Shows the SmaI and NotI restriction enzyme digestion from the genomic DNA of BF1 and BF2 obtained with pulse filed gel electrophoreses.

DETAILED DESCRIPTION

General Techniques and Definitions

Unless specifically defined otherwise, all technical and scientific terms used herein shall be taken to have the same meaning as commonly understood by one of ordinary skill in the art (e.g., enzyme, fermentation, inoculation).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "about", unless stated to the contrary, refers to +/−10%, more preferably +/−5%, even more preferably +/−1%, of the designated value.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

Brassicaceae

A person skilled in the art will appreciate that the methods as described herein are suitable for producing an isothiocyanate containing product from any Brassicaceae material comprising glucosinolate/s. As used herein, "Brassicaceae" refers to members of the Family Brassicaceae commonly referred to as mustards, crucifers or the cabbage family A person skilled in the art would appreciate that material can be from more than one Brassicaceae.

In an embodiment, the Brassicaceae is selected from the genus *Brassica* or *Cardamine*. In an embodiment, the *Brassica* is selected from *Brassica balearica*, *Brassica carinata*, *Brassica elongate*, *Brassica fruticulosa*, *Brassica hilarionis*, *Brassica juncea*, *Brassica napus*, *Brassica narinosa*, *Brassica nigra*, *Brassica oleracea*, *Brassica perviridis*, *Brassica rapa*, *Brassica rupestris*, *Brassica septiceps*, and *Brassica tournefortii*.

In an embodiment, the *Brassica* is *Brassica oleracea*.

In an embodiment, the *Brassica* is selected from *Brassica oleracea* variety oleracea (wild cabbage), *Brassica oleracea* variety *capitate* (cabbage), *Brassica rapa* subsp. *chinensis* (bok Choy), *Brassica rapa* subsp. *pekinensis* (napa cabbage), *Brassica napobrassica* (rutabaga), *Brassica rapa* var. *rapa* (turnip), *Brassica oleracea* variety *alboglabra* (kailan), *Brassica oleracea* variety *viridis* (collard greens), *Brassica oleracea* variety *longata* (jersey cabbage), *Brassica oleracea* variety *acephala* (ornamental kale), *Brassica oleracea* variety *sabellica* (kale), *Brassica oleracea* variety *palmifolia* (lacinato kale), *Brassica oleracea* variety *ramose* (perpetual kale), *Brassica oleracea* variety *medullosa* (marrow cabbage), *Brassica oleracea* variety *costata* (tronchuda kale), *Brassica oleracea* variety *gemmifera* (brussels sprout), *Brassica oleracea* variety *gongylodes* (kohlrabi), *Brassica oleracea* variety *italica* (broccoli), *Brassica olera-* cea variety *botrytis* (cauliflower, Romanesco broccoli, broccoli di torbole), *Brassica oleracea* variety *botrytis×italica* (broccoflower), and *Brassica oleracea* variety *italica×alboglabra* (Broccolini).

In an embodiment, the *Brassica* is *Brassica oleracea*, variety *italica* (broccoli).

In an embodiment, the Brassicaceae is selected from *Cardamine hirsuta* (bittercress), *Iberis sempervirens* (candytuft), *Sinapis arvensis* (charlock), *Armoracia rusticana* (horseradish), *Pringlea antiscorbutica* (Kerguelen cabbage), *Thlaspi arvense* (pennycress), *Raphanus raphanistrum* subsp. *sativus* (radish), *Eruca sativa* (rocket), *Anastatica hierochuntica* (rose of Jericho), *Crambe maritima* (sea kale), *Cakile maritima* (sea rocket), *Capsella bursa pastoris* (shepherd's purse), sweet alyssum, *Arabidopsis thaliana* (thale cress), *Nasturtium officinale* (watercress), *Sinapis alba* (white mustard), *Erophila verna* (whitlow grass), *Raphanus raphanistrum* (wild radish), *Isatis tinctoria* (woad), and *Nasturtium microphyllum* (yellow cress).

In an embodiment, the Brassicaceae has a high level of one or more glucosinolate/s. In an embodiment, the Brassicaceae has been selectively bred to have a high level of one or more glucosinolate/s. In an embodiment, "high level" of a glucosinolate can comprise a higher level of a glucosinolate than shown in Table 2 of Verkerk et al. (2009) in the corresponding Brassicaceae. In an embodiment, a high level of glucosinolate is a level of glucosinolate higher than 3400 µmol/kg dry weight. In an embodiment, a high level of glucosinolate is a level of glucosinolate higher than 4000 µmol/kg dry weight. In an embodiment, a high level of glucosinolate is a level of glucosinolate higher than 5000 µmol/kg dry weight. In an embodiment, a high level of glucosinolate is a level of glucosinolate higher than 8000 µmol/kg dry weight. In an embodiment, a high level of glucosinolate is a level of glucosinolate higher than 10,000 µmol/kg dry weight. In an embodiment, a high level of glucosinolate is a level of glucosinolate higher than 12,000 µmol/kg dry weight. In an embodiment, a high level of glucosinolate is a level of glucosinolate higher than 15,000 µmol/kg dry weight. In an embodiment, a high level of glucosinolate is a level of glucosinolate higher than 18,000 µmol/kg dry weight. In an embodiment, a high level of glucosinolate is a level of glucosinolate higher than 20,000 µmol/kg dry weight. In an embodiment, a high level of glucosinolate is a level of glucosinolate higher than 25,000 µmol/kg dry weight. In an embodiment, a high level of glucosinolate is a level of glucosinolate higher than 30,000 µmol/kg dry weight. In an embodiment, the Brassicaceae has been genetically modified or subjected to biotic or abiotic stress to have a high level of one or more glucosinolate/s. A person skilled in the art will appreciate that the Brassicaceae can be modified by any method known to a person skilled in the art.

In an embodiment, the glucosinolate is glucoraphanin (4-Methylsulphinylbutyl). In an embodiment, the glucosinolate is glucobrassicin (3-Indolylmethyl).

As used herein "Brassicaceae material" refers to any part of the Brassicaceae which comprises a glucosinolate, including, but not limited to, the leaves, stems, flowers, florets, seeds, and roots or mixtures thereof.

A person skilled in the art will appreciate that the methods as described herein are suitable for use with different volumes of Brassicaceae material, for example, but not limited to, at least 30 kg, or at least 50 kg, or at least 80 kg, or at least 100 kg, or at least 1,000 kg, or at least 2,000 kg, or at least 5,000 kg, or at least 8,000 kg, or at least 10,000 kg, or at least 15,000 kg, or at least 20,000 kg.

In an embodiment, the Brassicaceae material has been washed. As used herein "washing" removes visible soil and contamination. In an embodiment, the Brassicaceae material has been sanitized. As used herein "sanitized" refers to a reduction of pathogens on the Brassicaceae material.

In an embodiment, the Brassicaceae is mixed with other plant material. In an embodiment, the other plant material is vegetable or fruit material. In an embodiment, the vegetable is a carrot or beetroot.

Glucosinolates

As used herein "glucosinolate" refers to a secondary metabolite found at least in the Brassicaceae family that share a chemical structure consisting of a β-D-glucopyranose residue linked via a sulfur atom to a (Z)—N-hydroximinosulfate ester, plus a variable R group derived from an amino acid as described in Halkier et al. (2006). Examples of glucosinolates are provided in Halkier et al. (2006) and Agerbirk et al. (2012). The hydrolysis of glucosinolate can produce isothiocyanates, nitriles, epithionitrile, thiocyanate and oxazolidine-2-thione (FIG. 1A). Many glucosinolates play a role in plant defence mechanisms against pests and disease.

Glucosinolates are stored in Brassicaceae in storage sites. As used herein, a "storage site" is a site within the Brassicaceae where glucosinolates are present and myrosinase is not present.

As used herein "myrosinase" also referred to as "thioglucosidase", "sinigrase", or "sinigrinase" refers to a family of enzymes (EC 3.2.1.147) involved in plant defence mechanisms that can cleave thio-linked glucose. Myrosinases catalyze the hydrolysis of glucosinolates resulting in the production of isothiocyanates. Myrosinase is stored sometimes as myrosin grains in the vacuoles of particular idioblasts called myrosin cells, but have also been reported in protein bodies or vacuoles, and as cytosolic enzymes that tend to bind to membranes. Thus, in an embodiment, myrosinase is stored in a myrosin cell in Brassicaceae.

In an embodiment, pre-treating as described herein improves the access of myrosinase to a glucosinolate. As used herein "improves the access" or "access is improved" refers to increasing the availability of glucosinolate to the myrosinase enzyme allowing for the production of an isothiocyanate. In an embodiment, access is improved by the release of a glucosinolate from a glucosinolate storage site. In an embodiment, the glucosinolate storage site is mechanically ruptured (i.e. by maceration) or enzymatically degraded. In an embodiment, glucosinolate is released from a glucosinolate storage site by the activity of one or more polysaccharide degrading enzymes e.g. a cellulase, hemicellulase, pectinase and/or glycosidase. In an embodiment, access is improved by allowing the entry of myrosinase into a glucosinolate storage site. In an embodiment, access is improved by the release of myrosinase from myrosin cells. In an embodiment, about 10% to about 90% of a glucosinolate is released from a glucosinolate storage site. In an embodiment, about 20% to about 80% of a glucosinolate is released from a glucosinolate storage site. In an embodiment, about 30% to about 70% of a glucosinolate is released from a glucosinolate storage site. In an embodiment, about 40% to about 60% of a glucosinolate is released from a glucosinolate storage site. In an embodiment, about 45% to about 55% of a glucosinolate is released from a glucosinolate storage site. In an embodiment, about 10% of a glucosinolate is released from a glucosinolate storage site. In an embodiment, about 20% of a glucosinolate is released from a glucosinolate storage site. In an embodiment, about 30% of a glucosinolate is released from a glucosinolate storage site. In an embodiment, about 40% of a glucosinolate is released from a glucosinolate storage site. In an embodiment, about 50% of a glucosinolate is released from a glucosinolate storage site. In an embodiment, about 60% of a glucosinolate is released from a glucosinolate storage site. In an embodiment, about 70% of a glucosinolate is released from a glucosinolate storage site. In an embodiment, about 80% of a glucosinolate is released from a glucosinolate storage site. In an embodiment, about 90% of a glucosinolate is released from a glucosinolate storage site.

In an embodiment, the Brassicaceae material comprises one or more glucosinolate/s selected from an aliphatic, indole or aromatic glucosinolate.

In an embodiment, the aliphatic glucosinolate is selected from one or more of glucoraphanin (4-Methylsulphinylbutyl or glucorafanin), sinigrin (2-Propenyl), gluconapin (3-Butenyl), glucobrassicanapin (4-Pentenyl), progoitrin (2(R)-2-Hydroxy-3-butenyl, epiprogoitrin (2(S)-2-Hydroxy-3-butenyl), gluconapoleiferin (2-Hydroxy-4-pentenyl), glucoibervirin (3-Methylthiopropyl, glucoerucin (4-Methylthiobutyl), dehydroerucin (4-Methylthio-3-butenyl, glucoiberin (3-Methyl sulphinylpropyl), glucoraphenin (4-Methylsulphinyl-3-butenyl), glucoalyssin (5-Methylsulphinylpentenyl), and glucoerysolin (3-Methylsulphonylbutyl, 4-Mercaptobutyl).

In an embodiment, the indole glucosinolate is selected from one or more of glucobrassicin (3-Indolylmethyl), 4-hydroxyglucobrassicin (4-Hydroxy-3-indolylmethyl), 4-methoxyglucobrassicin (4-Methoxy-3-indolylmethyl), and neoglucobrassicin (1-Methoxy-3-indolylmethyl).

In an embodiment, the indole glucosinolate is selected from one or more of Glucotropaeolin (Benzyl) and Gluconasturtiin (2-Phenylethyl).

In an embodiment, the Brassicaceae material comprises one or more glucosinolate/s selected from benzylglucosinolate, allylglucosinolate and 4-methylsulfinylbutyl. In an embodiment, the glucosinolate is glucoraphanin (4-Methylsulphinylbutyl). In an embodiment, the glucosinolate is glucobrassicin (3-Indolylmethyl).

In an embodiment, pre-treating as described herein increases the extractable glucosinolate content compared to the extractable glucosinolate content of the Brassicaceae material before pre-treatment.

As used herein "extractable glucosinolate content" refers to the level of glucosinolate accessible in the Brassicaceae material for conversion to isothiocyanate. Excluding conversion into nitriles and other compounds the expected maximum yield of isothiocyanate from 1 mole of glucosinolate is 1 mole of isothiocyanate (1 mole of glucosinolate can maximally be converted to 1 mole of isothiocyanate, 1 mole of glucose and 1 mole of sulphate ion). Thus, in one example, the extractable glucoraphanin content of a commercial broccoli cultivar is 3400 µmol glucoraphanin/kg dw and the expected maximum yield of sulforaphane from the commercial broccoli cultivar is 3400 µmol sulforaphane/kg dw.

Isothiocyanates

As used herein "isothiocyanate" refers to sulphur containing phytochemicals with the general structure R—N=C=S which are a product of myrosinase activity upon a glucosinolate and bioactive derivatives thereof. In an embodiment, the isothiocyanate is sulforaphane (1-isothiocyanato-4-methylsulfinylbutane). In an embodiment, the isothiocyanate is allyl isothiocyanate (3-isothiocyanato-1-propene). In an embodiment, the isothiocyanate is benzyl isothiocyanate. In an embodiment, the isothiocyanate is phenethyl isothiocyanate. In an embodiment, the isothiocyanate is 3-Butenyl isothiocyanate. In an embodiment, the isothiocyanate is 5-vinyl-1,3-oxazolidine-2-thione. In an embodiment, the isothiocyanate is 3-(methylthio)propyl isothiocyanate. In an embodiment, the isothiocyanate is 3-(methylsulfinyl)-propyl isothiocyanate. In an embodiment, the isothiocyanate is 4-(methylthio)-butyl isothiocyanate. In an embodiment, the isothiocyanate is 1-methoxyindol-3-carbinol isothiocyanate. In an embodiment, the isothiocyanate is 2-phenylethyl isothiocyanate. In an embodiment, the isothiocyanate is iberin.

In an embodiment, the isothiocyanate containing product, further comprises one or more isothiocyanate bioactive derivative/s or oligomers thereof. In an embodiment, the isothiocyanate bioactive derivative is a derivative of any of the isothiocyanates as described herein. In an embodiment, the isothiocyanate bioactive derivative is a derivative of sulforaphane. In an embodiment, the isothiocyanate bioactive derivative is iberin. In an embodiment, the isothiocyanate bioactive derivative is allyl isothiocyanate. In an embodiment, the isothiocyanate bioactive derivative is indole-3-caribinol. In an embodiment, the isothiocyanate bioactive derivative is methoxy-indole-3-carbinol. In an embodiment, the isothiocyanate bioactive derivative is ascorbigen. In an embodiment, the isothiocyanate bioactive derivative is neoascorbigen.

Pre-Treatment

As use herein "pre-treatment" or "pre-treating" releases or aids in the release of a glucosinolate from glucosinolate storage site and/or allows myrosinase to enter a glucosinolate storage site in the Brassicaceae material. In an embodiment, pre-treating increases the exposure of a glucosinolate to myrosinase allowing myrosinase to convert a glucosinolate to an isothiocyanate.

In an embodiment, pre-treating reduces epithiospecifier protein (ESP) while maintaining endogenous myrosinase activity. As used herein "epithiospecifier protein" or "ESP" refers to a protein that directs myrosinase activity towards the production of nitriles and away from isothiocyanate production. Reducing or inhibiting ESP production (mRNA or protein) or activity can increase production of isothiocyanates.

As used herein, "reduces epithiospecifier protein" refers to decreasing the protein production or activity of ESP. In an embodiment, reducing ESP comprises inactivating (e.g. denaturing) ESP at high temperature. In an embodiment, ESP is denatured at temperatures of about 50° C. to about 80° C.

As used herein, "maintaining endogenous myrosinase activity" means not significantly reducing myrosinase activity compared to an untreated control. In an embodiment, endogenous myrosinase activity is not reduced by about 5% or more. In an embodiment, endogenous myrosinase activity is not reduced by about 10% or more. In an embodiment, endogenous myrosinase activity is not reduced by about 15% or more. In an embodiment, endogenous myrosinase activity is not reduced by about 20% or more. In an embodiment, endogenous myrosinase activity is not reduced by about 30% or more. In an embodiment, endogenous myrosinase activity is not reduced by about 40% or more. In an embodiment, endogenous myrosinase activity is not reduced by about 50% or more.

In an embodiment, pre-treating comprises one or more of the following: i) heating; ii) macerating; iii) microwaving; iv) exposure to high frequency sound waves (ultrasound), or v) pulse electric field processing, wherein the temperature of the Brassicaceae material does not exceed about 75° C. during pre-treating.

In an embodiment, the Brassicaceae material is heated in a fuel based heating system, an electricity based heating system (i.e. an oven or ohmic heating), radio frequency heating, high pressure thermal processing or a steam based heating system (indirect or direct application of steam). In an embodiment, the Brassicaceae material is heated in a sealed package (e.g. in a retort pouch). In an embodiment, the Brassicaceae material is heated in an oven, water bath, bioreactor, stove, water blancher, or steam blancher. In an embodiment, the Brassicaceae material is heated via high pressure thermal heating. In an embodiment, the Brassicaceae material is via ohmic heating. In an embodiment, the Brassicaceae material is via radio frequency heating. In an embodiment, the Brassicaceae material is blanched in water. In an embodiment, the Brassicaceae material is heated via high pressure thermal processing. In an embodiment, the Brassicaceae material is placed in a sealed package for high pressure thermal processing.

In an embodiment, pre-treating comprises heating the Brassicaceae material to about 50° C. to about 70° C. In an embodiment, pre-treating comprises heating the Brassicaceae material to about 50° C. to about 65° C. In an embodiment, pre-treating comprises heating the Brassicaceae material to about 50° C. to about 60° C. In an embodiment, heating comprises heating the Brassicaceae material to about 55° C. to about 70° C. In an embodiment, heating comprises heating the Brassicaceae material to about 60° C. to about 70° C. In an embodiment, heating comprises heating the Brassicaceae material to about 65° C. to about 70° C. In an embodiment, the Brassicaceae material is heated for about 30 seconds. In an embodiment, the Brassicaceae material is heated for about 1 minute. In an embodiment, the Brassicaceae material is heated for about 2 minutes. In an embodiment, the Brassicaceae material is heated for about 3 minutes. In an embodiment, the Brassicaceae material is heated for about 4 minutes. In an embodiment, the Brassicaceae material is heated for about 5 minutes.

In an embodiment, the Brassicaceae material is heated in a sealed package for about 1 min at about 60° C. In an embodiment, the Brassicaceae material is heated in a sealed package for about 2 mins at about 60° C. In an embodiment, the Brassicaceae material is heated in a sealed package for about 3 mins at about 60° C. In an embodiment, the Brassicaceae material is heated in a sealed package for about 4 mins at about 65° C. In an embodiment, the Brassicaceae material is heated in a sealed package for about 1 min at about 65° C. In an embodiment, the Brassicaceae material is heated in a sealed package for about 2 mins at about 65° C. In an embodiment, the Brassicaceae material is heated in a sealed package for about 3 mins at about 65° C. In an embodiment, the Brassicaceae material is heated in a sealed package for about 4 mins at about 65° C.

In an embodiment, the Brassicaceae material is heated in water for about 1 min at about 60° C. In an embodiment, the Brassicaceae material is heated in water for about 2 mins at about 60° C.

In an embodiment, heating comprises steaming the Brassicaceae material. In an embodiment, pre-treating comprises steaming the Brassicaceae material. In an embodiment, the Brassicaceae material is steamed to a temperature of about 50° C. to about 70° C. In an embodiment, the Brassicaceae material is steamed to a temperature of about 60° C. to about 70° C. In an embodiment, the Brassicaceae material is steamed for at least about 30 seconds. In an embodiment, the Brassicaceae material is steamed for at least about 1 minute. In an embodiment, the Brassicaceae material is steamed for at least about 2 minutes. In an embodiment, the Brassicaceae material is steamed for at least about 3 minutes. In an embodiment, the Brassicaceae material is steamed for at least about 4 minutes. In an embodiment, the Brassicaceae material is steamed for at least about 5 minutes.

In an embodiment, pre-treating comprises macerating the Brassicaceae material. As used herein "macerating", "macerated" or "macerate" refers to breaking the Brassicaceae material into smaller pieces. In an embodiment, macerating comprising decompartmentalizing at least about 30% to about 90% of the cells of the Brassicaceae material to allow myrosinase access to its substrate glucosinolates. In an embodiment, macerating comprising decompartmentalizing at least about 40% to about 90% of the cells of the Brassicaceae material. In an embodiment, macerating comprising decompartmentalizing at least about 50% to about 90% of the cells of the Brassicaceae material. In an embodiment, macerating comprising decompartmentalizing at least about 60% to about 90% of the cells of the Brassicaceae material. In an embodiment, macerating comprising decompartmentalizing at least about 70% to about 90% of the cells of the Brassicaceae material. A person skilled in the art will appreciate that decompartimentalizing a cell comprising breaking open the cell wall and disrupting the compartmentalization of organelles within a cell.

In an embodiment, the Brassicaceae material is macerated with a blender, grinder or pulveriser. In an embodiment, the Brassicaceae material is macerated so that at least about 80% of the Brassicaceae material is of a size of about 2 mm or less. In an embodiment, the Brassicaceae material is macerated so that at least about 80% of the Brassicaceae material is of a size of about 1 mm or less. In an embodiment, the Brassicaceae material is macerated so that at least about 80% of the Brassicaceae material is of a size of about 0.5 mm or less. In an embodiment, the Brassicaceae material is macerated so that at least about 80% of the Brassicaceae material is of a size of about 0.25 mm or less. In an embodiment, the Brassicaceae material is macerated so that at least about 80% of the Brassicaceae material is of a size of about 0.1 mm or less. In an embodiment, the Brassicaceae material is macerated so that at least about 80% of the Brassicaceae material is of a size of about 0.05 mm or less. In an embodiment, the Brassicaceae material is macerated so that at least about 80% of the Brassicaceae material is of a size of about 0.025 mm or less. In an embodiment, the Brassicaceae material is macerated so that at least about 80% of the Brassicaceae material is of a size of about 0.01 mm or less. In an embodiment, the Brassicaceae material is macerated so that about 50% to about 90% of the Brassicaceae material is of a size of about 2 mm or less. In an embodiment, the Brassicaceae material is macerated so that about 60% to about 80% of the Brassicaceae material is of a size of about 2 mm or less. In an embodiment, the Brassicaceae material is macerated so that about 50% to about 90% of the Brassicaceae material is of a size of about 1 mm or less. In an embodiment, the Brassicaceae material is macerated so that about 60% to about 80% of the Brassicaceae material is of a size of about 1 mm or less. In an embodiment, the Brassicaceae material is heated to a temperature of about 50° C. to about 70° C. during maceration. In an embodiment, the Brassicaceae material is heated to a temperature of about 55° C. to about 70° C. during maceration. In an embodiment, the Brassicaceae material is heated to a temperature of about 60° C. to about 70° C. during maceration. In an embodiment, the Brassicaceae material is heated to a temperature of about 65° C. to about 70° C. during maceration.

In an embodiment, pre-treating comprises heating and macerating the Brassicaceae material. In an embodiment, pre-treating produces a puree. As used herein a "puree" refers to Brassicaceae material blended to the consistency of a creamy paste or liquid.

A person skilled in the art will appreciate that "microwaves" or "microwaving" heats a substance such as Brassicaceae material by passing microwave radiation through the substance. In an embodiment, pre-treating comprises microwaving the Brassicaceae material. In an embodiment, Brassicaceae material is pre-treated in a consumer microwave or industrial microwave. In an embodiment, the industrial microwave is a continuous microwave system, for example, but not limited to the MIP 11 Industrial Microwave Continuous Cooking Over (Ferrite Microwave Technologies). In an embodiment, pre-treating comprises microwaving the Brassicaceae material. In an embodiment, the Brassicaceae material is microwaved at about 0.9 to about 2.45 GHz. In an embodiment, the Brassicaceae material is microwaved for at least about 30 seconds, or at least about 1 minute, or at least about 2 minutes, or at least 3 minutes.

In an embodiment, pre-treating comprises exposing the Brassicaceae material at low to medium frequency ultrasound waves. In an embodiment, pre-treating comprises exposing the Brassicaceae material with thermosonication (low to medium frequency ultrasound waves with heat of about 30° C. to about 60° C.). In an embodiment, the ultrasound waves are generated with an industrial scale ultrasonic processor. In an embodiment, the ultrasonic processor is a continuous or batch ultrasonic processor. In an embodiment, the ultrasonic processor is for example, but not limited to, UIP500hd or UIP4000 (Hielscher, Ultrasound Technology). In an embodiment, the ultrasounds waves are at a frequency of about 20 kHz to about 600 kHz. In an embodiment, the Brassicaceae material is exposed to sound waves for at least about 30 seconds, or at least about 1 minute, or at least about 2 minutes, or at least about 3 minutes, or about 5 minutes.

In an embodiment, pre-treating comprises exposing the Brassicaceae material to pulse electric field processing. Pulse electric field processing is a non-thermal processing technique comprising the application of short, high voltage pulses. The pulses induce electroporation of the cells of the Brassicaceae material enhancing the access of myrosinase to glucosinolates. In an embodiment, pulse electric field processing heats the Brassicaceae material to a temperature of about 40 to about 70° C. In an embodiment, pulse electric field processing heats the Brassicaceae material to a temperature of about 50° C. to about 70° C. In an embodiment, pulse electric field processing heats the Brassicaceae material to a temperature of about 60° C. to about 70° C. In an embodiment, pulse electric field processing comprises treating the Brassicaceae material with voltage pulses of about 20 to about 80 kV. In an embodiment, pre-treating converts about 10% to about 90% of a glucosinolate to an isothiocyanate. In an embodiment, pre-treating converts about 20% to about 80% of a glucosinolate to an isothiocyanate. In an embodiment, pre-treating converts about 30% to about 70% of a glucosinolate to an isothiocyanate. In an embodiment, pre-treating converts about 40% to about 60% of a glucosinolate to an isothiocyanate. In an embodiment, pre-treating converts about 10% of a glucosinolate to an isothiocyanate. In an embodiment, pre-treating converts about 20% of a glucosinolate to an isothiocyanate. In an embodiment, pre-treating converts about 30% of a glucosinolate to an isothiocyanate. In an embodiment, pre-treating converts about 40% of a glucosinolate to an isothiocyanate. In an embodiment, pre-treating converts about 50% of a glucosinolate to an isothiocyanate. In an embodiment, pre-treating converts about 60% of a glucosinolate to an isothiocyanate. In an embodiment, pre-treating converts about 70% of a glucosinolate to an isothiocyanate. In an embodiment, pre-treating converts about 80% of a glucosinolate to an isothiocyanate. In an embodiment, pre-treating converts about 90% of a glucosinolate to an isothiocyanate.

Fermentation

A person skilled in the art will appreciate that the fermentation method as described herein can comprise the use of any lactic acid bacteria. As used herein, "fermentation" refers to the biochemical breakdown of the Brassicaceae material by lactic acid bacteria. In an embodiment, fermentation with lactic acid bacteria is performed using the addition of exogenous lactic acid bacteria. As used herein, "lactic bacteria" or "lactic acid bacteria" are bacteria that produce lactic acid as an end product of carbohydrate fermentation, and can include, but are not limited to including bacteria from the genera *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus* and *Weissella*. In an embodiment, the lactic acid bacteria comprises myrosinase activity. In an embodiment, the lactic acid bacteria is from the genera *Leuconostoc*. In an embodiment, the lactic acid bacteria is from the genera *Lactobacillus*.

In an embodiment, the lactic acid bacteria is selected from one or more of *Lactobacillus plantarum, Leuconostoc mesenteroides, Lactobacillus rhamnosus, Lactobacillus pentosus, Lactobacillus brevis, Lactococus lactis, Pediococcus pentosaceus* and *Pedicoccus acidilacti*.

In an embodiment, the lactic acid bacteria was isolated from a Brassicaceae. In an embodiment, the lactic acid bacteria was isolated from a *Brassica oleracea*. In an embodiment, the lactic acid bacteria was isolated from broccoli. In an embodiment, the lactic acid bacteria was isolated from broccoli leaves. In an embodiment, the lactic acid bacteria was isolated from broccoli stem. In an embodiment, the lactic acid bacteria was isolated from broccoli puree. In an embodiment, the lactic acid bacteria was isolated from Australian broccoli.

In an embodiment, the lactic acid bacteria lacks myrosinase activity.

In an embodiment, the lactic acid bacteria is a *Lactobacillus*.

In an embodiment, the lactic acid bacteria is selected from: i) a *Leuconostoc mesenteroides*; ii) a *Lactobacillus plantarum*; iii) a *Lactobacillus pentosus*; iv) a *Lactobacillus rhamnosus*; v) a combination of i) and ii); vi) a combination of i), ii) and iii); and vii) a combination of i), ii) and iv).

In one embodiment, the lactic acid bacteria is *Leuconostoc mesenteroides*. In an embodiment, the *Leuconostoc mesenteroides* is ATCC8293. In an embodiment, the *Leuconostoc mesenteroides* is BF1 and/or BF2. In an embodiment, the *Leuconostoc mesenteroides* lacks myrosinase activity.

In one embodiment, the lactic acid bacteria is *Lactobacillus plantarum*. In an embodiment, the *Lactobacillus plantarum* lacks myrosinase activity.

In one embodiment, about 50% of the lactic acid bacteria is *Leuconostoc mesenteroides* and about 50% of the lactic acid bacteria is *Lactobacillus* sp.

In one embodiment, about 50% of the lactic acid bacteria is *Leuconostoc mesenteroides* and about 50% of the lactic acid bacteria is *Lactobacillus plantarum*.

In an embodiment, the *Lactobacillus plantarum* is selected from one or more or all of B1, B2, B3, B4 and B5. In an embodiment, the *Lactobacillus plantarum* is B1. In an embodiment, the *Lactobacillus plantarum* is B2. In an embodiment, the *Lactobacillus plantarum* is B3. In an embodiment, the *Lactobacillus plantarum* is B4. In an embodiment, the *Lactobacillus plantarum* is B5.

In an embodiment, fermentation occurs in the presence of at least 2, or at least 3, or at least 4, or at least 5, or at least 6 strains of lactic acid bacteria selected from BF1, BF2, B1, B2, B3, B4 and B5.

In one embodiment, the lactic acid bacteria is a recombinant bacteria modified to produce a high level of myrosinase activity compared to a control bacteria lacking the modification. A person skilled in the art will appreciate that the recombinant lactic acid bacteria is produced by any technique known to a person skilled in the art.

In an embodiment, the lactic acid bacteria is stressed, for example but not limited to, heat stress, cold stress, sub-lethal ultrasonic waves e.g. about 20 to about 2000 MHz, high pressure, dynamic high pressure or pulsed-electric field, to increase myrosinase activity and the activity of polysaccharide degrading enzymes compared to a control lactic acid bacteria that has not been stressed. In an embodiment, heat stress comprises heating the bacteria to greater than about 40° C. to about 75° C. In an embodiment, heat stress comprises heating the bacteria to greater than about 45° C. to about 65° C. In an embodiment, heat stress comprises heating the bacteria to greater than about 45° C. to about 55° C. In an embodiment, cold stress comprises lower the bacteria to temperature of about 0° C. to about 8° C. In an embodiment, cold stress comprises lower the bacteria to temperature of about 2° C. to about 6° C. In an embodiment, cold stress comprises lower the bacteria to temperature of about 4° C.

In an embodiment, the Brassicaceae material is inoculated with at least about $10^5$ CFU/g of a lactic acid bacteria as described herein. In an embodiment, the Brassicaceae material is inoculated with at least $10^6$ about CFU/g of a lactic acid bacteria as described herein. In an embodiment, the Brassicaceae material is inoculated with at least about $10^7$ CFU/g of a lactic acid bacteria as described herein. In an embodiment, the Brassicaceae material is inoculated with at least about $10^8$ CFU/g of a lactic acid bacteria as described herein. In an embodiment, the Brassicaceae material has been pre-treated.

In an embodiment, fermentation is at about 20° C. to about 34° C. In an embodiment, fermentation is at about 22° C. to about 34° C. In an embodiment, fermentation is at about 24° C. to about 34° C. In an embodiment, fermentation is at about 24° C. to about 30° C. In an embodiment, fermentation is at about 34° C. to about 34° C. In an embodiment, fermentation is at about 25° C. In an embodiment, fermentation is at about 30° C. In an embodiment, fermentation is at about 34° C.

In an embodiment, fermentation is for about 8 hours to about 17 days. In an embodiment, fermentation is for about 8 hours to about 14 days. In an embodiment, fermentation is for about 8 hours to about 7 days. In an embodiment, fermentation is for about 8 hours to about 5 days. In an embodiment, fermentation is for about 8 hours to about 4 days. In an embodiment, fermentation is for about 8 hours to about 3 days. In an embodiment, fermentation is for about 8 hours to about 30 hours. In an embodiment, fermentation is for about 8 to about 24 hours. In an embodiment, fermentation is for about 10 hours to about 24 hours. In an embodiment, fermentation is for about 10 days. In an embodiment, fermentation is for about 9 days. In an embodiment, fermentation is for about 8 days. In an embodiment, fermentation is for about 7 days. In an embodiment, fermentation is for about 4 days. In an embodiment, fermentation is for about 6 days. In an embodiment, fermentation is for about 5 days. In an embodiment, fermentation is for about 72 hours. In an embodiment, fermentation is for about 60 hours. In an embodiment, fermentation is for about 45 hours. In an embodiment, fermentation is for about 30 hours. In an embodiment, fermentation is for about 24 hours. In an embodiment, fermentation is for about 20 hours. In an embodiment, fermentation is for about 18 hours. In an embodiment, fermentation is for about 15 hours. In an embodiment, fermentation is for about 16 hours. In an embodiment, fermentation is for about 14 hours. In an embodiment, fermentation is for about 12 hours. In an embodiment, fermentation is for about 10 hours. In an embodiment, fermentation is for about 8 hours. In an embodiment, the fermentation culture is stirred. In an embodiment, stirring is intermittent. In an embodiment, stirring is continuous. In a particularly preferred embodiment, fermentation is for 15 hours with intermittent stirring. In a particularly preferred embodiment, fermentation is for 24 hours with intermittent stirring.

In an embodiment, the fermentation reaction is complete when the composition reaches a pH of about 4.5 to about 3.8. In an embodiment, the fermentation reaction is complete when the composition reaches a pH of about 4.5 to about 3.6. In an embodiment, the fermentation reaction is complete when the composition reaches a pH of about 4.5 to about 4.04. In an embodiment, the fermentation reaction is complete when the composition reaches a pH of about 4.3 to about 4.04. In an embodiment, the fermentation reaction is complete when the composition reaches a pH of 4.5 or less, or 4.4 or less, or 4.3 or less, or 4.04 or less, or 3.8 or less. In an embodiment, the fermentation reaction is complete when the composition reaches a pH of 4.5 or less. In an embodiment, the fermentation reaction is complete when the composition reaches a pH of 4.4 or less.

In an embodiment, if present fermentation reduces the number of one or more or all of: *E. coli*, *Salmonella* and *Listeria*. In an embodiment, if present fermentation reduces the CFU/g of one or more or all of: *E. coli*, *Salmonella* and *Listeria*.

In an embodiment, no salt is added to the fermentation culture.

In an embodiment, fermentation increases the extractable glucosinolate content compared to the extractable glucosinolate content in the pre-treated Brassicaceae material. In an embodiment, fermentation increases the extractable glucosinolate content compared to the extractable glucosinolate content in the Brassicaceae material. In an embodiment, fermentation increases the extractable glucosinolate content is increased by about 100% to about 500% compared to the extractable glucosinolate content in the Brassicaceae material. In an embodiment, fermentation increases the extractable glucosinolate content by about 200% to about 450% compared to the extractable glucosinolate content in the Brassicaceae material. In an embodiment, fermentation increases the extractable glucosinolate content by about 250% to about 450% compared to the extractable glucosinolate content in the Brassicaceae material. In an embodiment, fermentation increases the extractable glucosinolate content by about 300% to about 400% compared to the extractable glucosinolate content in the Brassicaceae material. In an embodiment, fermentation increases the extractable glucosinolate content by about 300% compared to the extractable glucosinolate content in the Brassicaceae material. In an embodiment, fermentation increases the extractable glucosinolate content by about 400% compared to the extractable glucosinolate content in the Brassicaceae material. In an embodiment, the glucosinolate is glucoraphanin.

Acidification

The pre-treated material can by acidified to improve the microbial safety and stability (susceptibility to microbial degradation) of the product and increase the stability of isothiocyanate in the product. Acidification can be achieved by the addition of organic acids, such as, but not limited to lactic, acetic, ascorbic, and citric acid. In embodiment, acidification can be achieved with the addition of glucono-delta-lactone. In an embodiment, acidification comprises lowering the pH to a pH of about 4.4 to about 3.4. In an embodiment, acidification comprises lowering the pH to a pH of 4.5, or 4.4, or 4.2, or 4, or 3.8, or 3.6, or 3.4 or less. In an embodiment, acidification comprises lowering the pH to a pH of 4.4 of less.

Isothiocyanate Containing Product from Brassicaceae

An isothiocyanate containing product from Brassicaceae as described herein can be produced by the methods as described herein. It will be appreciated be a person skilled in the art that an isothiocyanate containing product produced using the methods as described herein contains higher levels of isothiocyanates, for example sulforaphane, than the Brassicaceae material or Brassicaceae material subjected to fermentation alone (without pre-treatment as described herein). For example, macerated broccoli from a commercial broccoli cultivar has a sulforaphane concentration of ~800 μmol/Kg dw (~149.8 mg/Kg dw), fermented macerated broccoli has a sulforaphane concentration of ~1600 μmol/Kg dw (~278.8 mg/Kg dw) and pre-treated and fermented broccoli produced using the methods as described herein has a sulforaphane concentration of ~13100 μmol/Kg dw (~2318.7 mg/Kg dw).

In an embodiment, the isothiocyanate containing product comprises at least about 4 times more isothiocyanate than macerated Brassicaceae material. In an embodiment, the isothiocyanate containing product comprises at least about 6 times more isothiocyanate than the macerated Brassicaceae material. In an embodiment, the isothiocyanate containing product comprises at least about 8 times more isothiocyanate than the macerated Brassicaceae material. In an embodiment, the isothiocyanate containing product comprises at least about 10 times more isothiocyanate than the macerated Brassicaceae material. In an embodiment, the isothiocyanate containing product comprises at least about 12 times more isothiocyanate than the macerated Brassicaceae material. In an embodiment, the isothiocyanate containing product comprises at least about 14 times more isothiocyanate than the macerated Brassicaceae material. In an embodiment, the isothiocyanate containing product comprises at least about 16 times more isothiocyanate than the macerated Brassicaceae material. In an embodiment, the isothiocyanate containing product comprises at least about 17 times more isothiocyanate than the macerated Brassicaceae material. In an embodiment, the isothiocyanate containing product comprises about 4 times to about 17 times more isothiocyanate than the macerated Brassicaceae material. In an embodiment, the isothiocyanate containing product comprises about 4 times to about 16 times more isothiocyanate than the macerated Brassicaceae material. In an embodiment, the isothiocyanate containing product comprises about 8 times to about 16 times more isothiocyanate than the macerated Brassicaceae material. In an embodiment, the isothiocyanate containing product comprises about 10 times to about 16 times more isothiocyanate than the macerated Brassicaceae material. In an embodiment, the isothiocyanate containing product comprises about 12 times to about 16 times more isothiocyanate than the macerated Brassicaceae material. In an embodiment, the isothiocyanate containing product comprises about 14 times to about 16 times more isothiocyanate than the macerated Brassicaceae material. In an embodiment, the isothiocyanate is sulforaphane.

In an embodiment, the level of isothiocyanate present in the isothiocyanate containing product is higher than what would be expected from the extractable glucosinolate content of the Brassicaceae material. In an embodiment, the isothiocyanate containing product comprises at least about 1 times the expected maximum yield of isothiocyanate based on the extractable glucosinolate content. In an embodiment, the isothiocyanate containing product comprises at least about 2 times the expected maximum yield of isothiocyanate based on the extractable glucosinolate content. In an embodiment, the isothiocyanate containing product comprises at least about 3 times the expected maximum yield of isothiocyanate based on the extractable glucosinolate content. In an embodiment, the isothiocyanate containing product comprises at least about 3.8 times the expected maximum yield of isothiocyanate based on the extractable glucosinolate content. In an embodiment, the isothiocyanate containing product comprises at least about 4 times the expected maximum yield of isothiocyanate based on the extractable glucosinolate content. In an embodiment, the isothiocyanate containing product comprises about 1 times to about 4 times the expected maximum yield of isothiocyanate based on the extractable glucosinolate content. In an embodiment, the isothiocyanate containing product comprises about 1 times to about 3.8 times the expected maximum yield of isothiocyanate based on the extractable glucosinolate content. In an embodiment, the isothiocyanate containing product comprises about 2 times to about 3.8 times the expected maximum yield of isothiocyanate based on the extractable glucosinolate content. In an embodiment, the isothiocyanate containing product comprises about 2 times to about 3 times the expected maximum yield of isothiocyanate based on the extractable glucosinolate content.

In an embodiment, the level of sulforaphane present in the isothiocyanate containing product is higher than what would be expected from the extractable glucoraphanin content of the Brassicaceae material. In an embodiment, the isothiocyanate containing product comprises at least about 1 times the expected maximum yield of sulforaphane based on the extractable glucoraphanin content. In an embodiment, the isothiocyanate containing product comprises at least about 2 times the expected maximum yield of sulforaphane based on the extractable glucoraphanin content. In an embodiment, the isothiocyanate containing product comprises at least about 3 times the expected maximum yield of sulforaphane based on the extractable glucoraphanin content. In an embodiment, the isothiocyanate containing product comprises at least about 3.8 times the expected maximum yield of sulforaphane based on the extractable glucoraphanin content. In an embodiment, the isothiocyanate containing product comprises at least about 4 times the expected maximum yield of sulforaphane based on the extractable glucoraphanin content. In an embodiment, the isothiocyanate containing product comprises about 1 times to about 4 times the expected maximum yield of sulforaphane based on the extractable glucoraphanin content. In an embodiment, the isothiocyanate containing product comprises about 1 times to about 3.8 times the expected maximum yield of sulforaphane based on the extractable glucoraphanin content. In an embodiment, the isothiocyanate containing product comprises about 1 times to about 3 times the expected maximum yield of sulforaphane based on the extractable glucoraphanin content. In an embodiment, the isothiocyanate containing product comprises about 2 times to about 3 times the expected maximum yield of sulforaphane based on the extractable glucoraphanin content.

In an embodiment, the isothiocyanate containing product comprises about 100 mg/kg dw to about 7000 mg/kg dw of isothiocyanate. In an embodiment, the isothiocyanate containing product comprises about 500 mg/kg dw to about 7000 mg/kg dw of isothiocyanate. In an embodiment, the isothiocyanate containing product comprises about 1000 mg/kg dw to about 7000 mg/kg dw of isothiocyanate. In an embodiment, the isothiocyanate containing product comprises about 1600 mg/kg dw to about 4000 mg/kg dw of isothiocyanate. In an embodiment, the isothiocyanate containing product comprises about 1600 mg/kg dw to about 3000 mg/kg dw of isothiocyanate. In an embodiment, the isothiocyanate containing product comprises about 2000 mg/kg dw to about 4000 mg/kg dw of isothiocyanate. In an embodiment, the isothiocyanate containing product comprises about 2000 mg/kg dw of to about 7000 mg/kg dw of isothiocyanate. In an embodiment, the isothiocyanate containing product comprises about 3000 mg/kg dw isothiocyanate to about 7000 mg/kg of isothiocyanate. In an embodiment, the isothiocyanate containing product comprises about 2300 mg/kg dw of the isothiocyanate.

In an embodiment, the isothiocyanate containing product comprises at least about 100 mg/kg dw of the isothiocyanate. In an embodiment, the isothiocyanate containing product comprises at least about 200 mg/kg dw of the isothiocyanate. In an embodiment, the isothiocyanate containing product comprises at least about 250 mg/kg dw of the isothiocyanate. In an embodiment, the isothiocyanate containing product comprises at least about 300 mg/kg dw of the isothiocyanate. In an embodiment, the isothiocyanate containing product comprises at least about 350 mg/kg dw of the isothiocyanate. In an embodiment, the isothiocyanate containing product comprises at least about 400 mg/kg dw of the isothiocyanate. In an embodiment, the isothiocyanate containing product comprises at least about 450 mg/kg dw of the isothiocyanate. In an embodiment, the isothiocyanate containing product comprises at least about 500 mg/kg dw of the isothiocyanate. In an embodiment, the isothiocyanate containing product comprises at least about 550 mg/kg dw of the isothiocyanate. In an embodiment, the isothiocyanate containing product comprises at least about 600 mg/kg dw of the isothiocyanate. In an embodiment, the isothiocyanate containing product comprises at least about 650 mg/kg dw of the isothiocyanate. In an embodiment, the isothiocyanate containing product comprises at least about 700 mg/kg dw of the isothiocyanate. In an embodiment, the isothiocyanate containing product comprises at least about 1000 mg/kg dw of the isothiocyanate. In an embodiment, the isothiocyanate containing product comprises at least about 2000 mg/kg dw of the isothiocyanate. In an embodiment, the isothiocyanate containing product comprises at least about 3000 mg/kg dw of the isothiocyanate. In an embodiment, the isothiocyanate containing product comprises at least about 4000 mg/kg dw of the isothiocyanate. In an embodiment, the isothiocyanate containing product comprises at least about 5000 mg/kg dw of the isothiocyanate. In an embodiment, the isothiocyanate containing product comprises at least about 6000 mg/kg dw of the isothiocyanate. In an embodiment, the isothiocyanate containing product comprises at least about 7000 mg/kg dw of the isothiocyanate.

In an embodiment, the isothiocyanate containing product comprises at least about 100 mg/kg dw of sulforaphane. In an embodiment, the isothiocyanate containing product comprises at least about 150 mg/kg of sulforaphane. In an embodiment, the isothiocyanate containing product comprises at least about 200 mg/kg dw of sulforaphane. In an embodiment, the isothiocyanate containing product comprises at least about 250 mg/kg of sulforaphane. In an embodiment, the isothiocyanate containing product comprises at least about 300 mg/kg dw of sulforaphane. In an embodiment, the isothiocyanate containing product comprises at least about 350 mg/kg dw of sulforaphane. In an embodiment, the isothiocyanate containing product comprises at least about 400 mg/kg dw of sulforaphane. In an embodiment, the isothiocyanate containing product comprises at least about 450 mg/kg dw of sulforaphane. In an embodiment, the isothiocyanate containing product comprises at least about 500 mg/kg dw of sulforaphane. In an embodiment, the isothiocyanate containing product comprises at least about 550 mg/kg dw of sulforaphane. In an embodiment, the isothiocyanate containing product comprises at least about 600 mg/kg dw of sulforaphane. In an embodiment, the isothiocyanate containing product comprises at least about 650 mg/kg dw of sulforaphane. In an embodiment, the isothiocyanate containing product comprises at least about 700 mg/kg dw of sulforaphane. In an embodiment, the isothiocyanate containing product comprises at least about 1000 mg/kg of sulforaphane dw. In an embodiment, the isothiocyanate containing product comprises at least about 2000 mg/kg dw of sulforaphane. In an embodiment, the isothiocyanate containing product comprises at least about 3000 mg/kg dw of sulforaphane. In an embodiment, the isothiocyanate containing product comprises at least about 4000 mg/kg dw of sulforaphane. In an embodiment, the isothiocyanate containing product comprises at least about 5000 mg/kg dw of sulforaphane. In an embodiment, the isothiocyanate containing product comprises at least about 6000 mg/kg dw of sulforaphane. In an embodiment, the isothiocyanate containing product comprises at least about 7000 mg/kg dw of sulforaphane.

In an embodiment, the isothiocyanate containing product comprises at least about 5% more total fibre than the Brassicaceae material. In an embodiment, the isothiocyanate containing product comprises at least about 10% more total fibre than the Brassicaceae material. In an embodiment, the isothiocyanate containing product comprises at least about 15% more total fibre than the Brassicaceae material. In an embodiment, the isothiocyanate containing product comprises at least about 20% more total fibre than the Brassicaceae material. In an embodiment, the isothiocyanate containing product comprises at least about 4% more protein than the Brassicaceae material. In an embodiment, the isothiocyanate containing product comprises at least about 6% more protein than the Brassicaceae material. In an embodiment, the isothiocyanate containing product comprises at least about 8% more protein than the Brassicaceae material. In an embodiment, the isothiocyanate containing product comprises at least about 10% more protein than the Brassicaceae material.

In an embodiment, the isothiocyanate containing product comprises at least about 10% less carbohydrate than the Brassicaceae material. In an embodiment, the isothiocyanate containing product comprises at least about 20% less carbohydrate than the Brassicaceae material. In an embodiment, the isothiocyanate containing product comprises at least about 30% less carbohydrate than the Brassicaceae material. In an embodiment, the isothiocyanate containing product comprises at least about 40% less carbohydrate than the Brassicaceae material. In an embodiment, the isothiocyanate containing product comprises at least about 45% less carbohydrate than the Brassicaceae material. In an embodiment, the isothiocyanate containing product comprises at least about 48% less carbohydrate than the Brassicaceae material. In an embodiment, the isothiocyanate containing product comprises about 10% to about 48% less carbohydrate than the Brassicaceae material.

In an embodiment, the isothiocyanate containing product comprises an increased level of polyphenolic glycosides compared to the Brassicaceae material. In an embodiment, the polyphenolic glycosides are anthocyanin glycosides. In an embodiment, the polyphenolic glycosides are phenolic acid glycosides. In an embodiment, the polyphenolic glycosides are phenolic acids.

In an embodiment, the isothiocyanate containing product comprises an increased level of glucosinolates compared to the Brassicaceae material. In an embodiment, the glucosinolate is glucoraphanin. In an embodiment, glucoraphanin is increased at least about 25 fold. In an embodiment, the glucosinolate is glucobrassicin. In an embodiment, the glucobrassicin is increased by 26 times. In an embodiment, the isothiocyanate containing product comprises indole-3-carbinol. In an embodiment, indol-3carbinol is increased at least about 2 fold in the isothiocyanate containing product compared to the macerated Brassicaceae material. In an embodiment, indol-3-carbinol is increased at least about 3 fold in the isothiocyanate containing product compared to the macerated Brassicaceae material. In an embodiment, the isothiocyanate containing product comprises ascorbigen. In an embodiment, ascorbigen is increased at least about 2 fold in the isothiocyanate containing product compared to the macerated Brassicaceae material. In an embodiment, ascorbigen is increased at least about 3 fold in the isothiocyanate containing product compared to the macerated Brassicaceae material.

In an embodiment, the isothiocyanate containing product comprises an increased level of one or more of ferullic acid, syringic acid, phenyllactic acid, chlorogenic acid rutin, sinapic acid, methyl syringate, hesperetin, quercetin and kaempferol compared to the Brassicaceae material. In an embodiment, the isothiocyanate containing product comprises an increased level of chlorogenic acid compared to the Brassicaceae material. In an embodiment, chlorogenic acid is increased about 6.6 fold. In an embodiment, the isothiocyanate containing product comprises an increased level of sinapic acid compared to the Brassicaceae material. In an embodiment, sinapic acid is increased about 23.8 fold. In an embodiment, the isothiocyanate containing product comprises an increased level of kaempferol compared to the Brassicaceae material. In an embodiment, kaempferol is increased about 10.5 fold.

In an embodiment, the isothiocyanate containing product comprises an decreased level of one or more of protocatechuic acid, gallic acid, 4,hydroxybenzoic acid, vanillic acid, 2,3dihydroxybenzoic acid, p-cuomaric acid, cinnamic acid, catechin, rosmarinic acid, caffeic acid compared to the Brassicaceae material.

In an embodiment, about 40% of a glucosinolate present in the Brassicaceae material is converted to an isothiocyanate in the isothiocyanate containing product. In an embodiment, about 50% of a glucosinolate present in the Brassicaceae material is converted to an isothiocyanate in the isothiocyanate containing product. In an embodiment, about 60% of a glucosinolate present in the Brassicaceae material is converted to an isothiocyanate in the isothiocyanate containing product. In an embodiment, about 70% of a glucosinolate present in the Brassicaceae material is converted to an isothiocyanate in the isothiocyanate containing product. In an embodiment, about 80% of a glucosinolate present in the Brassicaceae material is converted to an isothiocyanate in the isothiocyanate containing product. In an embodiment, about 90% of a glucosinolate present in the Brassicaceae material is converted to an isothiocyanate in the isothiocyanate containing product. In an embodiment, about 95% of a glucosinolate present in the Brassicaceae material is converted to an isothiocyanate in the isothiocyanate containing product. In an embodiment, about 97% of a glucosinolate present in the Brassicaceae material is converted to an isothiocyanate in the isothiocyanate containing product. In an embodiment, about 98% of a glucosinolate present in the Brassicaceae material is converted to an isothiocyanate in the isothiocyanate containing product. In an embodiment, about 99% of a glucosinolate present in the Brassicaceae material is converted to an isothiocyanate in the isothiocyanate containing product. In an embodiment, about 100% of a glucosinolate present in the Brassicaceae material is converted to an isothiocyanate in the isothiocyanate containing product. In an embodiment, about 40% to about 100% of a glucosinolate present in the Brassicaceae material is converted to an isothiocyanate in the isothiocyanate containing product. In an embodiment, about 40% to about 80% of a glucosinolate present in the Brassicaceae material is converted to an isothiocyanate in the isothiocyanate containing Brassicaceae product.

In an embodiment, the isothiocyanate in the isothiocyanate containing product is stable for at least a week, or for at least two weeks, or for at least 3 weeks, or for at least 4 weeks, or for at least 6 weeks, or for at least 8 weeks, or for at least 10 weeks, or for at least 12 weeks, or for at least 14 weeks when stored at about 4° C. to about 25° C. In an embodiment, the isothiocyanate in the isothiocyanate containing product is stable for at least 4 weeks when stored at about 4° C. to about 25° C. In an embodiment, the isothiocyanate in the isothiocyanate containing product is stable for at least 8 weeks when stored at about 4° C. to about 25° C. In an embodiment, the isothiocyanate in the isothiocyanate containing product is stable for at least 12 weeks when stored at about 4° C. to about 25° C.

As used herein "stable" refers to no decrease or only a minor decrease in isothiocyanate concentration when stored at 4° C. for six weeks. In an embodiment, a minor decrease refers to a decrease in isothiocyanate concentration of about 1% to about 30%. In an embodiment, a minor decrease refers to a decrease in isothiocyanate concentration of about 5% or less. In an embodiment, a minor decrease refers to a decrease in isothiocyanate concentration of about 10% or less. In an embodiment, a minor decrease refers to a decrease in isothiocyanate concentration of about 15% or less. In an embodiment, a minor decrease refers to a decrease in isothiocyanate concentration of about 20% or less. In an embodiment, a minor decrease refers to a decrease in isothiocyanate concentration of about 30% or less. Isothiocyanate analysis can be performed by any method know to a person skilled in the art and for example as shown in Example 1 for sulforaphane.

In an embodiment, the isothiocyanate is sulforaphane.

In an embodiment, the isothiocyanate containing product is resistant to yeast, mould and/or coliform growth for at least a week, or for at least two weeks, or for at least 3 weeks, or for at least 4 weeks, or for at least 6 weeks, or for at least 8 weeks, or for at least 10 weeks, or for at least 12 weeks, or for at least 14 weeks when stored at about 4° C. to about 25° C.

In an embodiment, the isothiocyanate containing product is resistant to yeast, mould and/or coliform growth for at least 4 weeks when stored at about 4° C. to about 25° C. In an embodiment, the isothiocyanate containing product is resistant to yeast, mould and/or coliform growth for at least 8 weeks when stored at about 4° C. to about 25° C. In an embodiment, the isothiocyanate containing product is resistant to yeast, mould and/or coliform growth for at least 12 weeks when stored at about 4° C. to about 25° C.

As used herein "resistant" to yeast, mould and/or coliform growth means that <1 Log CFU/g of yeast, mould and/or coliform is detectable in the sample after the above listed time periods using the methods described in Example 1. In an embodiment, the isothiocyanate containing product comprises about 20 g/100 gdw to about 32 g/100 gdw total fibre. In an embodiment, the isothiocyanate containing product comprises about 20 g/100 gdw total fibre. In an embodiment, the isothiocyanate containing product comprises about 25 g/100 gdw total fibre. In an embodiment, the isothiocyanate containing product comprises about 28 g/100 gdw total fibre. In an embodiment, the isothiocyanate containing product comprises about 29 g/100 gdw total fibre. In an embodiment, the isothiocyanate containing product comprises about 30 g/100 gdw total fibre. In an embodiment, the isothiocyanate containing product comprises about 32 g/100 gdw total fibre.

In an embodiment, the isothiocyanate containing product comprises an ORAC antioxidant capacity of about 14000 µmol TE/100 gdw to about 19000 µmol TE/100 gdw. In an embodiment, the isothiocyanate containing product comprises an ORAC antioxidant capacity of about 14000 µmol TE/100 gdw. In an embodiment, the isothiocyanate containing product comprises an ORAC antioxidant capacity of about 15000 µmol TE/100 gdw. In an embodiment, the isothiocyanate containing product comprises an ORAC antioxidant capacity of about 16000 µmol TE/100 gdw. In an embodiment, the isothiocyanate containing product comprises an ORAC antioxidant capacity of about 17000 µmol TE/100 gdw. In an embodiment, the isothiocyanate containing product comprises an ORAC antioxidant capacity of about 18000 µmol TE/100 gdw. In an embodiment, the isothiocyanate containing product comprises an ORAC antioxidant capacity of about 18695 µmol TE/100 gdw. In an embodiment, the isothiocyanate containing product comprises an ORAC antioxidant capacity of about 19000 µmol TE/100 gdw.

In an embodiment, the isothiocyanate containing product comprises a total polyphenol content of about 1750 mg GAE/100 gdw to about 2600 mg GAE/100 gdw. In an embodiment, the isothiocyanate containing product comprises a total polyphenol content of about 1750 mg GAE/100 gdw. In an embodiment, the isothiocyanate containing product comprises a total polyphenol content of about 2000 mg GAE/100 gdw. In an embodiment, the isothiocyanate containing product comprises a total polyphenol content of about 2100 mg GAE/100 gdw. In an embodiment, the isothiocyanate containing product comprises a total polyphenol content of about 2200 mg GAE/100 gdw. In an embodiment, the isothiocyanate containing product comprises a total polyphenol content of about 2300 mg GAE/100 gdw. In an embodiment, the isothiocyanate containing product comprises a total polyphenol content of about 2360 mg GAE/100 gdw.

In an embodiment, the isothiocyanate containing product comprises a total titratable acidity of about 0.9% to about 1.1% lactic acid equivalent. In an embodiment, the isothiocyanate containing product comprises a total titratable acidity of about 1.1% lactic acid equivalent.

In an embodiment, the isothiocyanate containing product comprises a total protein content of about 23 g/100 gdw to about 39 g/100 gdw. In an embodiment, the isothiocyanate containing product comprises a total protein content of about 23 g/100 gdw to about 30 g/100 gdw. In an embodiment, the isothiocyanate containing product comprises a total protein content of about 25 g/100 gdw. In an embodiment, the isothiocyanate containing product comprises a total protein content of about 27 g/100 gdw. In an embodiment, the isothiocyanate containing product comprises a total protein content of about 28 g/100 gdw. In an embodiment, the isothiocyanate containing product comprises a total protein content of about 29 g/100 gdw. In an embodiment, the isothiocyanate containing product comprises a total protein content of about 30 g/100 gdw. In an embodiment, the isothiocyanate containing product comprises a total protein content of about 32 g/100 gdw.

In an embodiment, the isothiocyanate containing product comprises at least about 100 mg/kg dw of an isothiocyanate and one or more or all of the following:
 i) total fibre at about 29 to about 36 g/100 gdw;
 ii) an ORAC antioxidant capacity of about 15000 to about 18695 µmol TE/100 gdw;
 iii) a total polyphenol content of about 2310 to about 2600 mg GAE/100 gdw;
 iv) a total titratable acidity of about 0.9 to about 1.1% lactic acid equivalent;
 v) a total protein content of about 27 to about 39 g/100 gdw; and
 vi) *Leuconostoc mesenteroides* and/or *Lactobacillus plantarum*.

In an embodiment, the isothiocyanate containing product is produced from broccoli.

The Brassicaceae products as described herein can comprise live lactic acid bacteria which can aid the conversion of glucosinolate present in the isothiocyanate containing product to an isothiocyanates during digestion of a glucosinolate containing product in a subject (i.e. they act as a probiotic). In an embodiment, the lactic acid bacteria is a *Leuconostoc mesenteroide*. In an embodiment, the lactic acid bacteria is *Lactobacillus* sp. In an embodiment, the lactic acid bacteria is *Lactobacillus plantarum*.

In an embodiment, the isothiocyanate containing product comprises lactic acid bacteria at a concentration of at least about $10^2$ CFU/g. In an embodiment, the isothiocyanate containing product comprises lactic acid bacteria at a concentration of at least about $10^2$ CFU/g. In an embodiment, the isothiocyanate containing product comprises lactic acid bacteria at a concentration of at least about $10^5$ CFU/g. In an embodiment, the isothiocyanate containing product comprises lactic acid bacteria at a concentration of at least about $10^6$ CFU/g. In an embodiment, the isothiocyanate containing product comprises lactic acid bacteria at a concentration of at least about $10^7$ CFU/g. In an embodiment, the isothiocyanate containing product comprises lactic acid bacteria at a concentration of at least about $10^8$ CFU/g. In an embodiment, the isothiocyanate containing product comprises lactic acid bacteria at a concentration of at least about $10^9$ CFU/g.

In an embodiment, live lactic acid bacteria are present in the isothiocyanate containing product for at least 10 days when stored at about 4° C. to about 25° C. In an embodiment, live lactic acid bacteria are present in the isothiocyanate containing product at least 20 days when stored at about 4° C. to about 25° C. In an embodiment, live lactic acid bacteria are present in the isothiocyanate containing product at least 30 days when stored at about 4° C. to about 25° C. In an embodiment, live lactic acid bacteria are present in the isothiocyanate containing product at least 40 days when stored at about 4° C. to about 25° C. In an embodiment, live lactic acid bacteria are present in the isothiocyanate containing product at least 50 days when stored at about 4° C. to about 25° C. In an embodiment, live lactic acid bacteria are present in the isothiocyanate containing product at least 60 days when stored at about 4° C. to about 25° C. In an embodiment, live lactic acid bacteria are present in the isothiocyanate containing product at least 70 days when stored at about 4° C. to about 25° C. In an embodiment, live lactic acid bacteria are present in the isothiocyanate containing product at least 80 days when stored at about 4° C. to about 25° C. In an embodiment, live lactic acid bacteria are present in the isothiocyanate containing product at least 85 days when stored at about 4° C. to about 25° C. In an embodiment, live lactic acid bacteria are present in the isothiocyanate containing product at least 90 days when stored at about 4° C. to about 25° C.

In an embodiment, the lactic acid bacteria is a *Lactobacillus* sp. In an embodiment, the lactic acid bacteria is *Lactobacillus plantarum*. In an embodiment, the lactic acid bacteria is *Leuconostoc mesenteroides*. In an embodiment, the bacteria are present at a concentration of at least about $10^7$ CFU/g.

In an embodiment, the isothiocyanate containing product comprises one or more bacteriocins produced by lactic acid bacteria. In an embodiment, the bacteriocin is a Class I bacteriocin. In an embodiment, the bacteriocin is a Class II bacteriocin. In an embodiment, the bacteriocin is a Class III bacteriocin. Examples of bacteriocins produced by lactic acid bacteria can be found in Alvarez-Sieiro et al. (2016).

In an embodiment, the isothiocyanate containing product is a food product. In an embodiment, the isothiocyanate containing product is a nutraceutical. In an embodiment, the isothiocyanate containing product is a supplement. In an embodiment, the isothiocyanate containing product is a food ingredient. In an embodiment, the isothiocyanate containing product is a probiotic. In an embodiment, the isothiocyanate containing product is an animal feed. The animal can be an aquatic animal such as fish or livestock. In an embodiment, the isothiocyanate containing product is a pesticide. In an embodiment, the isothiocyanate containing product is a cosmeceutical. In an embodiment, the isothiocyanate containing product is topically formulated.

In an embodiment, the isothiocyanate containing product is a solid, liquid, puree or a powder. In an embodiment, the isothiocyanate containing product is dried to a powder after fermentation. In an embodiment, the isothiocyanate containing product is freeze dried after fermentation. In an embodiment, the isothiocyanate containing product is microencapsulated as described in WO2005030229 after fermentation. In an embodiment, the isothiocyanate containing product is formulated as a pill.

Post-Treatment

In an embodiment, after fermentation or acidification the isothiocyanate containing product can be post-treated to inactivate microbes that for example contribute to degradation of the product or a pathogenic if consumed.

As used herein "post-treatment" or "post-treating" refers to treatment of the isothiocyanate containing product as described herein after fermentation to inactivate microbes. As used herein "microbes" refers to bacterial, viral, fungal or eukaryotic activity that can result in degradation or spoilage of the isothiocyanate containing product. As used herein "inactivate" or "inactivation" of microbes refers to reducing the viable microbes by about 1 to about 7 logs. In an embodiment, the viable microbes are reduced by about 1 to 6 logs. In an embodiment, the viable microbes are reduced by about 2 to 6 logs. In an embodiment, the viable microbes are reduced by about 3 to 6 logs.

A person skilled in the art will appreciate that the post treatment can be any method that inactivates microbes, including for example, heat treatment, UV treatment, ultrasonic processing, pulsed electric field processing or high pressure processing. In an embodiment, the isothiocyanate containing product is post-treated with heat processing. In an embodiment, the isothiocyanate containing product is post-treated with high pressure processing. In an embodiment, the isothiocyanate containing product is in a sealed package during post-treatment. In an embodiment, the isothiocyanate containing product is in a sealed package during high pressure processing. In an embodiment, the isothiocyanate containing product is in a sealed package during heat treatment. In an embodiment, high pressure processing comprises treating the isothiocyanate containing product with isostatic pressure at about 300 to about 600 MPa. In an embodiment, high pressure processing comprises treating the isothiocyanate containing product with isostatic pressure at about 350 to about 550 MPa. In an embodiment, high pressure processing comprises treating the isothiocyanate containing product with isostatic pressure at about 300 to about 400 MPa. In an embodiment, heat treatment comprises heating the sample to a temperature of about 60° C. to about 121° C. In an embodiment, heat treatment comprises heating the sample to a temperature of about 65° C. to about 100° C. In an embodiment, heat treatment comprises heating the sample to a temperature of about 65° C. to about 80° C. In an embodiment, heat treatment comprises heating the sample to a temperature of about 65° C. to about 75° C.

Isolated Strains and Starter Cultures

In an embodiment, the present invention provides isolated strains of lactic acid bacteria suitable for use in the methods and products as described herein.

In an embodiment, the present invention provides an isolated strain of lactic acid bacteria selected from:
  i) BF1 deposited under V17/021729 on 25 Sep. 2017 at the National Measurement Institute Australia;
  ii) BF2 deposited under V17/021730 on 25 Sep. 2017 at the National Measurement Institute Australia;
  iii) B1 deposited under V17/021731 on 25 Sep. 2017 at the National Measurement Institute Australia;
  iv) B2 deposited under V17/021732 on 25 Sep. 2017 at the National Measurement Institute Australia;
  v) B3 deposited under V17/021733 on 25 Sep. 2017 at the National Measurement Institute Australia;
  vi) B4 deposited under V17/021734 on 25 Sep. 2017 at the National Measurement Institute Australia; and
  vii) B5 deposited under V17/021735 on 25 Sep. 2017 at the National Measurement Institute Australia.

In an embodiment, the present invention provides an isolated strain of *Leuconostoc mesenteroides* comprising genomic DNA which when cleaved with SmaI and/or NotI produces a SmaI and/or NotI fingerprint identical to BF1 or BF2. The SmaI and NotI fingerprints for BF1 and BF2 are shown in FIG. 13.

In an embodiment, the present invention provides an isolated strain of *Lactobacillus plantarum* comprising genomic DNA which when cleaved with SmaI and/or NotI produces a SmaI and/or NotI fingerprint identical to B1, B2, B3, B4 or B5.

In an embodiment, the present invention provides an isolated strain of *Leuconostoc mesenteroides* comprising one or more or all of the polymorphisms listed in Table 18 or 19 that differs from ATCC8293. In an embodiment, the isolated strain of *Leuconostoc mesenteroides* comprises 5 or more of the polymorphisms listed in Table 18 or 19 that differs from ATCC8293. In an embodiment, the isolated strain of *Leuconostoc mesenteroides* comprises 10 or more of the polymorphisms listed in Table 18 or 19 that differs from ATCC8293. In an embodiment, the isolated strain of *Leuconostoc mesenteroides* comprises 15 or more of the polymorphisms listed in Table 18 or 19 that differs from ATCC8293. In an embodiment, the isolated strain of *Leuconostoc mesenteroides* comprises 19 or more of the polymorphisms listed in Table 18 or 19 that differs from ATCC8293. In an embodiment, the isolated strain of *Leuconostoc mesenteroides* comprises 20 or more of the polymorphisms listed in Table 19 that differs from ATCC8293. In an embodiment, the isolated strain of *Leuconostoc mesenteroides* comprises 30 or more of the polymorphisms listed in Table 19 that differs from ATCC8293. In an embodiment, the isolated strain of *Leuconostoc mesenteroides* comprises 50 or more of the polymorphisms listed in Table 19 that differs from ATCC8293. In an embodiment, the isolated strain of *Leuconostoc mesenteroides* comprises 80 or more of the polymorphisms listed in Table 19 that differs from ATCC8293. In an embodiment, the isolated strain of *Leuconostoc mesenteroides* comprises 100 or more of the polymorphisms listed in Table 19 that differs from ATCC8293. In an embodiment, the isolated strain of *Leuconostoc mesenteroides* comprises 150 or more of the polymorphisms listed in Table 19 that differs from ATCC8293. In an embodiment, the isolated strain of *Leuconostoc mesenteroides* comprises 200 or more of the polymorphisms listed in Table 19 that differs from ATCC8293. In an embodiment, the isolated strain of *Leuconostoc mesenteroides* comprises 300 or more of the polymorphisms listed in Table 19 that differs from ATCC8293. In an embodiment, the isolated strain of *Leuconostoc mesenteroides* comprises 400 or more of the polymorphisms listed in Table 19 that differs from ATCC8293.

In an embodiment, the present invention provides an isolated strain of *Lactobacillus plantarum* comprising one or more or all the polymorphisms listed in Table 13, Table 14, Table 15, Table 16 or Table 17 that differs from ATCC8014. In an embodiment, the present invention provides an isolated strain of *Lactobacillus plantarum* comprising 5 or more of the polymorphisms listed in Table 13, Table 14, Table 15, Table 16 or Table 17 that differs from ATCC8014. In an embodiment, the present invention provides an isolated strain of *Lactobacillus plantarum* comprising 10 or more of the polymorphisms listed in Table 13, Table 14, Table 15, Table 16 or Table 17 that differs from ATCC8014. In an embodiment, the present invention provides an isolated strain of *Lactobacillus plantarum* comprising 15 or more of the polymorphisms listed in Table 13, Table 14, Table 15, Table 16 or Table 17 that differs from ATCC8014. In an embodiment, the present invention provides an isolated strain of *Lactobacillus plantarum* comprising 20 or more of the polymorphisms listed in Table 13, Table 14, Table 15, Table 16 or Table 17 that differs from ATCC8014. In an embodiment, the present invention provides an isolated strain of *Lactobacillus plantarum* comprising 25 or more of the polymorphisms listed in Table 13, Table 14, Table 15, Table 16 or Table 17 that differs from ATCC8014. In an embodiment, the present invention provides an isolated strain of *Lactobacillus plantarum* comprising 30 or more of the polymorphisms listed in Table 13, Table 14, Table 15, Table 16 or Table 17 that differs from ATCC8014. In an embodiment, the present invention provides an isolated strain of *Lactobacillus plantarum* comprising 35 or more of the polymorphisms listed in Table 13, Table 14, Table 15, Table 16 or Table 17 that differs from ATCC8014. In an embodiment, the present invention provides an isolated strain of *Lactobacillus plantarum* comprising 40 or more of the polymorphisms listed in Table 13, Table 14, Table 15, Table 16 or Table 17 that differs from ATCC8014.

In an embodiment, the present invention provides a starter culture for producing an isothiocyanate containing product or a probiotic comprising lactic acid bacteria comprising one or more of the isolated strains as described herein. As used herein a "starter culture" is a culture of live microorganisms for fermentation. In an embodiment, the present invention provides a starter culture for producing an isothiocyanate containing product or a probiotic comprising lactic acid bacteria selected from one or more or all of:
  i) BF1 deposited under V17/021729 on 25 Sep. 2017 at the National Measurement Institute Australia;
  ii) BF2 deposited under V17/021730 on 25 Sep. 2017 at the National Measurement Institute Australia;
  iii) B1 deposited under V17/021731 on 25 Sep. 2017 at the National Measurement Institute Australia;
  iv) B2 deposited under V17/021732 on 25 Sep. 2017 at the National Measurement Institute Australia;
  v) B3 deposited under V17/021733 on 25 Sep. 2017 at the National Measurement Institute Australia;
  vi) B4 deposited under V17/021734 on 25 Sep. 2017 at the National Measurement Institute Australia; and
  vii) B5 deposited under V17/021735 on 25 Sep. 2017 at the National Measurement Institute Australia.

In an embodiment, the Brassicaceae material is inoculated with at least about $10^5$ CFU/g of a starter culture as described herein. In an embodiment, the Brassicaceae material is inoculated with at least $10^6$ about CFU/g of a starter culture as described herein. In an embodiment, the Brassicaceae material is inoculated with at least about $10^7$ CFU/g of a starter culture as described herein. In an embodiment, the Brassicaceae material is inoculated with at least about $10^8$ CFU/g of a starter culture as described herein. In an embodiment, the Brassicaceae material is inoculated with at least about $10^{10}$ CFU/g of a starter culture as described herein. In an embodiment, the Brassicaceae material is inoculated with about $10^5$ CFU/g to about $10^{10}$ CFU/g of a starter culture as described herein.

Probiotics

In an embodiment, the present invention provides for a probiotic comprising one or more of the lactic acid bacteria isolated from a Brassicaceae. As used herein a "probiotic" refers to a live microorganism which when administered in an adequate amount confers a health benefit to the host. In an embodiment, the lactic acid bacteria was isolated from a *Brassica oleracea*. In an embodiment, the lactic acid bacteria was isolated from broccoli. In an embodiment, the lactic acid bacteria was isolated from Australian broccoli. In an embodiment, the lactic acid bacteria is selected from: i) a *Leuconostoc mesenteroides*; ii) a *Lactobacillus plantarum*; iii) a *Lactobacillus pentosus*; iv) a *Lactobacillus rhamnosus*; v) a combination of i) and ii); vi) a combination of i), ii) and iii); and vii) a combination of i), ii) and iv). In one embodiment, the lactic acid bacteria is selected from one or more or all of BF1, BF2, B1, B2, B3, B4 and B5. In an embodiment, the lactic acid bacteria is B1. In an embodiment, the lactic acid bacteria is B2. In an embodiment, the lactic acid bacteria is B3. In an embodiment, the lactic acid bacteria is B4. In an embodiment, the lactic acid bacteria is B5. In an embodiment, the probiotic is a capsule, tablet, powder or liquid. In an embodiment, the probiotic is microencapsulated as described in WO 2005030229.

EXAMPLES

Example 1—Methods

Chemicals and Reagents

HPLC grade methanol, sodium dihydrogen phosphate, sodium hydroxide (NaOH) and hydrochloric acid (HCl) were purchased from Merck (Damstadt, Germany). Folin-Ciocalteu's reagent, sodium carbonate ($Na_2CO_3$), gallic acid, fluorescein sodium salt and dibasic-potassium phosphate were purchased from Sigma Aldrich (St. Louis, MO, USA). Sodium dihydrogen phosphate, 6-hydroxy-2,5,7,8-tetramethylchroman-2-carboxylic acid (trolox), 2,20-azobis (2-methylpropionamidine) dihydrochloride (AAPH) were purchased from Sapphire Bioscience (Redfern, NSW, Australia).

Lactic Acid Bacteria

Lactic acid bacteria used during fermentation were selected from one or more of:
LP: *Lactobacillus plantarum* ATCC8014;
LGG: *Lactobacillus rhamnosus* ATCC53103;
B1: *Lactobacillus plantarum* isolated from broccoli deposited under V17/021731 on 25 Sep. 2017 at the National Measurement Institute Australia;
B2: *Lactobacillus plantarum* isolated from broccoli deposited under V17/021732 on 25 Sep. 2017 at the National Measurement Institute Australia;
B3: *Lactobacillus plantarum* isolated from broccoli deposited under V17/021733 on 25 Sep. 2017 at the National Measurement Institute Australia;
B4: *Lactobacillus plantarum* isolated from broccoli deposited under V17/021734 on 25 Sep. 2017 at the National Measurement Institute Australia;
B5: *Lactobacillus plantarum* isolated from broccoli deposited under V17/021735 on 25 Sep. 2017 at the National Measurement Institute Australia;
BF1: *Leuconostoc mesenteroides* isolated from broccoli puree deposited under V17/021729 on 25 Sep. 2017 at the National Measurement Institute Australia;
BF2: *Leuconostoc mesenteroides* isolated from broccoli puree BF2 deposited under V17/021730 on 25 Sep. 2017 at the National Measurement Institute Australia;
BP: pooled BF1, BF2; and
LAB: pooled B1, B2, B3, B4 and B5.

BF1 and BF2 were identified as *Leuconostoc mesenteroides* via a 16s-RNA sequence (Australian Genome Research Facility; data not shown). B1 to B5 were identified as *Lactobacillus plantarum* based on 16S-RNA sequence. The identity of all the isolates were confirmed by whole genome sequence analysis.

Isolation of Lactic Acid Bacteria from Broccoli and Broccoli Puree

The above *Lactobacillus plantarum* B1, B2, B3, B4 and B5 were isolated from broccoli leaves and stem. The leaves and stem were washed with water and homogenised with added peptone saline using a stomacher. The soaking solution was serially diluted and spread plated on De Man, Rogosa and Sharpe (MRS) agar. The plates were incubated under anaerobic condition for 48 to 72 hrs at 37° C. for isolating presumptive mesophilic lactic acid bacteria. Based on different colonial morphology on MRS plates, colonies were isolated, cultivated in MRS broth, screened using staining and biochemical characterisation techniques, and kept frozen with glycerol at −80° C. The isolates were identified at species level using 16s RNA sequencing at AGRF.

For the isolation of *Leuconostoc mesenteroides* BF1 and BF2, broccoli floret puree was used after serial dilution instead of the suspension described above for the isolation from broccoli leaves.

Preparation of Starter Cultures

The lactic acid bacteria strains, *Leuconostoc mesenteroides* and *Lactobacillus plantarum*, were isolated from broccoli and identified by Australian Genome Research Facility Ltd. To obtain the primary culture, lactic acid bacteria cultures which were stored at −80° C. were inoculated into 10 mL of MRS broth (Oxoid, Victoria, Australia) and incubated at 30° C. for 24 h to obtain an initial biomass of 8 log colony-forming units per milliliter (CFU/mL). Two mL of each primary inoculum was inoculated into 200 mL of MRS broth and incubated for 24 hrs at 30° C. The cultures were collected by centrifugation at 2000 g for 15 min at 4° C., washed twice with sterile phosphate buffer saline (PBS), and all the *Lactobacillus plantarum* cultures were mixed together and all the *Leuconostoc mesenteroides* cultures were mixed together. The two culture suspensions were diluted to 10 log CFU/ml and were mixed at the same volumetric proportion and stored with glycerol at −80° C. until use as a mixed starter culture for broccoli fermentation.

Fermentation Method

Broccoli (*Brassica oleracea* L. ssp. *Italic;* 30 kg) florets were cut approximately 2 cm from the crown, shredded to smaller pieces and, were macerated with Milli-Q water in ratio of 3:2 for 1 min using magic bullet blender. The broccoli slurry, was mixed well and placed into sterile plastic bottles (200 mL) with screw lids. Each bottle of broccoli puree (200 mL) was inoculated with the prepared starter culture at an initial concentration of 8 log CFU/g. The fermentation experiment was carried out in 48 bottles in parallel at 30° C., until a pH value of about 4.0 was reached (Day 4). After the fermentation phase was completed, 3 samples were taken out as the Day 0 storage samples, the other samples were separated to two lots for the storage experiments: one lot was stored in a refrigerator (4° C.) and another stored in room thermostated at 25° C. Samples were periodically taken over 12 weeks for microbiological, physicochemical and phytochemical analyses. The fermented broccoli puree was compared with raw broccoli puree which was stored at −20° C. after homogenization and puree samples incubated for the same period of time as the fermented samples without inoculation by LAB.

Sampling

For time course experiments, sampling was performed at days 10, 20, 30, 40, 50, 60, 70, 80, and 90, and on days 14, 28, 42, 56, 70 and 84 for samples stored at 25° C. and 4° C., respectively. Sampling was performed in triplicate with color measured on the surface and pH measured immediately after opening the fermentation bottles. Thereafter, samples were taken for microbiological analysis and titratable acidity analysis. The remaining material was separated into two parts, the first portion was frozen and freeze dried, ground to fine powder and stored in a desiccator for further analyses, and the second part was frozen and kept at −20° C. until glucoraphanin and sulforaphane analyses.

Microbiological Analysis

For microbial analysis, three different media were used to measure CFU per g broccoli puree of the different microorganisms; the plate counts for total lactic acid bacteria on DeMan-Rogosa-Sharp (MRS) agar, for total enterobacteria on violet red bile glucose agar (VRBGA), and the yeasts and mould on potato dextrose agar (PDA). For each sample, serial dilution of the broccoli suspension in sterilized peptone saline diluent were made and 0.1 mL of the dilutions were plated onto agar plates in duplicates. After aerobic incubation at 25° C. for 72 h (PDA), 37° C. for 24 h (VRBGA), and anaerobic incubation at 30° C. for 72 h (MRS), respectively, the CFU were counted.

Determination of pH and Titratable Acidity

The pH value was determined directly in fermentation bottles containing broccoli puree by a pH meter (PHM240, MeterLab). Titratable acidity (TA) of broccoli samples was measured with an Automatic titrator (Titralab 854 titration manager, Radiometric Analytical, France). In brief, diluted broccoli puree (10 mL) was titrated using 0.1 M NaOH to the end point pH=8.1 and the result obtained was expressed as gram equivalent of lactic acid per liter of sample in accordance with the following equation:

$$TA(g/L) = \frac{[v \times acid\ factor \times 1000]}{sample\ volume}$$

where, v is titer volume of NaOH. The acid factor for lactic acid is 0.009.

Total Protein and Color Analyses

The total protein content of broccoli samples was determined as total nitrogen content multiplied by 6.25. Total nitrogen content of broccoli was analyzed using a Dumas combustion method with LECO TruMac apparatus (LECO Corporation, Michigan, USA). The color indexes (L, a, b) of fermented broccoli sample were determined using a Chroma meter CR-200 tristimulus colorimeter (Minolta, Osaka, Japan). The color values obtained were expressed as lightness/darkness (as L*), redness/greenness (a*) and yellow/blueness (b*). The total color difference ($\Delta E$) was calculated according to the following equation:

$$\Delta E=[(L^*-L_0)^2+(a^*-a_0)^2+(b^*-b_0)^2]^{1/2}$$

where, $L_0$, $a_0$, $b_0$ are color values of fresh unfermented broccoli.

Determination of Total Polyphenol Content

The total phenolic content (TPC) was measured spectrophotometrically using the Folin-Ciocalteu colorimetric method (Singleton and Rossi, 1965) with modifications. Briefly, 50 mg of broccoli powder was suspended in 10 mL of acidified (1% HCl) methanol/water (70:30, v/v) solution and extracted in ultrasonic bath (IDK technology Pty Ltd, VIC, Australia) for 8 min. The extracts were kept for 16 h at 4° C. and filtered with 0.2 µM filter and stored at 4° C. until analysis. 1 mL of 0.2 N Folin-Ciocalteu reagent, 800 µL of sodium carbonate solution (7.5% v/v) and 180 µL Milli-Q grade water were added to the extract (20 µL). After 1 h of incubation in the dark at 37° C., the absorbance was measured at 765 nm in triplicates using a spectrophotometer (UV-1700 Pharma Spec, SHIMADZU). Gallic acid was used as a standard and TPC was expressed as the gallic acid equivalent (GAE) in mg per 100 g of fresh weight (mg GAE/100 g FW) based on a standard curve developed using known concentrations of gallic acid.

Oxygen Radical Absorbance Capacity Assay

Freeze-dried broccoli powder (10 mg) was suspended in 10 mL of methanol/water (80:20, v/v), the extraction solvent. The slurry was extracted at 650 rpm on a Heidolph Multi-Reax (John Morris Scientific, NSW, Australia) at room temperature for an hour. Then it was centrifuged at 25,000 g for 15 min in 4° C., the supernatant was collected, and was ready for analysis after 100× dilution with 75 mM potassium phosphate buffer (pH 7.4). ORAC analysis was conducted according to the procedure reported by Huang et al. (2002) with minor modifications. The assay was carried out in opaque 96-well plates (dark optical bottom, Waltham, MA, USA). The assay reactants included 81.6 nM of fluorescein, 153 mM of AAPH, Trolox standard of different concentration (100, 50, 25, 12.5, and 6.25 µM), and 75 mM phosphate buffer as the blank. The reactants were added in the following order: 25 µL of diluted sample; either 25 µL of 75 mM phosphate buffer, 25 µL Trolox standard and 150 µL fluorescein. After adding the fluorescein, the plate was incubated at 37° C. for 10 min and then the AAPH (25 µL) was added. Immediately after addition of AAPH, the plate was placed in the fluorescence plate reader (BMG Labtech ClarioStar, Germany) and the fluorescence was measured every 3 min until it decreased to less than 5% of original fluorescence. The ORAC values were calculated as the area under the curve (AUC) and expressed as micromoles of trolox equivalent (TE) per gram dry weight of broccoli (µmol TE/g DW). Each sample was assayed triplicate.

Sulforaphane Analysis

The extraction of sulforaphane from broccoli matrix was conducted following the methods of Li et al. (2012) with some modification. In brief, frozen broccoli (2 g) was mixed with 2 mL of Milli-Q water and vortexed for 1 min. Then 20 mL ethyl acetate was added to the slurry followed by sonication for 5 min and shaking for 20 min at 4° C. The slurry was then centrifuged at 15,000 g for 10 min, and the supernatant was collected. Then another 15 mL ethyl acetate was added to the precipitate to carry out the second extraction. Pooled extracts from each sample were evaporated to dryness with a vacuum spin dryer (SC250EXP, Thermo Fisher Scientific, CA, USA) at room temperature, and stored at −20° C. until analysis. The concentration of sulforaphane was determined using an Acquity™ Ultra Performance LC system (Waters Corporation, Milford, MA, USA), which is equipped with a binary solvent delivery manager and a sample manger. Chromatographic separations were performed on a 2.1×50 mm, Acquity BEH C18 chromatography column. The mobile phase A and B were 0.1% formic acid in millique water and 0.1% formic acid in acetonitrile, respectively. The gradient elution system consisted of mobile phase A (0.1% formic acid in millique water) and B (0.1% formic acid in acetonitrile) and separation was achieved using the following gradient: 0-2 min, 10% B; 2-5 min, 20% B; 5-10 min, 10% B. The column temperature was kept constant at 30° C. The flow-rate was 0.350 mL/min and the injection volume was 5 µL.

Prior to analysis, all samples were dissolved in 1 mL 30% acetonitrile, and filtered through a 0.22 µm membrane filter (Merk Millipore, Billerica, MA, USA). The identification of each peak was based on the retention time and the chromatography of authentic standards. The concentrations of each compound were calculated according to a standard curve, and the results were expressed as micromoles per kilogram DW (µmol/kg DW) of broccoli.

Glucoraphanin Analysis

The extraction of glucoraphanin from raw or fermented broccoli was carried out according to the method of Cai and Wang (2016) with some modification. Accordingly, to 2 g of frozen broccoli puree, 10 mL of boiling Milli-Q water was added, and the mixture was incubated for 5 min in a boiling water bath. It was then cooled and centrifuged at 15000×g for 15 min, and the supernatant was collected. The precipitate was extracted once more with 8 mL of boiling water. Pooled extracts from each sample were evaporated to dryness with a vacuum spin dryer (Speedvac SC250EXP, Thermo Fisher Scientific, CA, USA) at 3° C., and stored at −20° C. until analysis. The concentration of glucoraphanin was quantified using an Alliance HPLC instrument (Waters Corporation, Milford, MA, USA) equipped with Photo Diode Array Detector 2998. A HPLC column—Luna® 3 μM Hydrophilic Interaction Liquid Chromatography (HILIC) 200° A (100×4.6 mm; Phenomenex, Torrance, CA, USA) was used for the analysis at a column temperature of 25° C. The mobile phase consisted of an acetonitrile/water (85:15, v/v) with 30 mM Ammonium formate (solution A) and acetonitrile (solution B) with the following isocratic flow program: solution A 70%; solution B 30%. Other chromatographic conditions included a constant flow rate of 2.0 mL/min, an injection volume of 100 μL, a run time of 8 min, and detection wavelength of 235 nm. Prior to analysis, all samples were dissolved in 1 mL solvent A, and filtered through a 0.22 μm membrane filter (Merk Millipore, Billerica, MA, USA). The identification of each peak was based on the retention time and the chromatography of an authentic glucoraphanin standard. The concentrations of glucoraphanin were calculated using a standard curve, and the results were expressed as micromoles glucoraphanin per kilogram DW (μmol/kg DW) of broccoli.

Statistical Analysis

All experiments were conducted in triplicate and the results were expressed as mean values. A one-way analyses of variance (ANOVA) was applied to evaluate the significance of the differences among the mean values at 0.05 significance level (p<0.05). The statistical analysis was conducted using the statistical software, SPSS 16.0 for Windows (SPSS Inc., Chicago, IL, USA).

Example 2—Microbial Analysis of Lactic Acid Bacteria Fermented Broccoli Florets

The fermentation of broccoli puree was carried out as described in the fermentation section of Example 1. The counts of total lactic acid bacteria were lower for raw broccoli compared to inoculated broccoli as showed in Table 1. After 4 days of fermentation, the pH of the sample reached 4.04 and fermentation was stopped, and the fermented sample before storage experiments was taken as the Day 0 sample. It is clear from Table 1 and FIG. 1C that the counts of total lactic acid bacteria of the Day 0 sample were significantly increased (8 log CFU/g) compared to the raw broccoli. During the first two weeks of storage, the viable number of total lactic acid bacteria increased to the highest values of 9 log CFU/g for samples stored at both 25° C. and 4° C. (Table 1 and Table 2). During storage at 25° C., the total lactic acid bacteria counts increased to 9 log CFU/g at Day 10 and slowly declined during storage to 5 log CFU/g by Day 50, and declined further to almost undetectable level after Day 70. In contrast,

TABLE 1

Microbiological and physicochemical changes of fermented broccoli during the storage at room temperature (25° C.).

| | Microbial loads (Log CFU/g) | | | pH | TA (g/L) | TP (mg/g, FW) | Color | | | |
| --- | --- | --- | --- | --- | --- | --- | --- | --- | --- | --- |
| | MRS | PDA | VRBGA | | | | L | a | b | ΔE |
| Raw broccoli | 2.4 ± 0.2 | 2.5 ± 0.1 | 3.4 ± 0.1 | 6.33 ± 0.00 | 4.8 ± 0.2 | 26.9 ± 0.0 | 48.4 ± 0.4 | −13.2 ± 0.1 | 17.2 ± 0.2 | — |
| Day 0 | 8.4 ± 0.2 | <1 | <1 | 4.04 ± 0.00 | 10.7 ± 0.7 | 29.6 ± 0.8 | 48.5 ± 0.7 | −2.1 ± 0.1 | 13.6 ± 0.6 | 11.7 |
| Days 10 | 9.4 ± 0.1 | <1 | <1 | 3.87 ± 0.02 | 14.4 ± 0.2 | 27.8 ± 0.8 | 47.7 ± 0.8 | −1.1 ± 0.2 | 12.2 ± 0.5 | 13.1 |
| Days 20 | 6.2 ± 0.3 | <1 | <1 | 3.76 ± 0.02 | 14.7 ± 0.2 | 30.5 ± 0.8 | 47.1 ± 0.5 | −1.1 ± 0.0 | 12.5 ± 0.2 | 13 |
| Days 30 | 6.2 ± 0.1 | <1 | <1 | 3.78 ± 0.00 | 15.1 ± 0.3 | 29.7 ± 1.2 | 47.2 ± 0.2 | −1.0 ± 0.1 | 10.9 ± 0.5 | 13.8 |
| Days 40 | 6.1 ± 0.4 | <1 | <1 | 3.79 ± 0.02 | 15.1 ± 0.4 | 28.8 ± 1.1 | 46.3 ± 0.5 | −0.8 ± 0.1 | 11.0 ± 0.9 | 14 |
| Days 50 | 5.1 ± 0.6 | <1 | <1 | 3.75 ± 0.02 | 15.2 ± 0.5 | 28.5 ± 0.1 | 45.8 ± 0.5 | −0.9 ± 0.1 | 11.0 ± 0.2 | 14 |
| Days 60 | 2.4 ± 0.1 | <1 | <1 | 3.76 ± 0.01 | 15.4 ± 0.3 | 27.3 ± 0.6 | 45.4 ± 0.1 | −0.9 ± 0.1 | 10.5 ± 0.1 | 14.3 |
| Days 70 | 1.5 ± 0.1 | <1 | <1 | 3.76 ± 0.01 | 15.7 ± 0.1 | 27.7 ± 0.2 | 45.3 ± 0.5 | −0.9 ± 0.1 | 9.9 ± 0.4 | 14.7 |
| Days 80 | <1 | <1 | <1 | 3.76 ± 0.01 | 15.7 ± 0.7 | 28.3 ± 0.2 | 45.9 ± 0.1 | −0.9 ± 0.1 | 9.7 ± 0.1 | 14.6 |
| Days 90 | <1 | <1 | <1 | 3.71 ± 0.01 | 15.7 ± 0.3 | 28.7 ± 0.4 | 45.0 ± 0.0 | −0.8 ± 0.2 | 9.3 ± 0.2 | 15.1 |

Each value was expressed as mean ± standard deviation (n = 3).
"—"not available.
MRS, de Man-Rogosa-Sharpe agar for LAB; PDA, potato dextrose agar for total yeasts and moulds; VRBGA, violet red bile glucose agar for Enterobacteriaceae; TA, titratable acidity; TP: total protein; ΔE: total color difference.

TABLE 2

Microbiological and physicochemical changes of fermented broccoli during the storage at 4° C.

| | Microbial loads (Log CFU/g) | | | pH | TA (g/L) | TP (mg/g, FW) | Color | | | |
| --- | --- | --- | --- | --- | --- | --- | --- | --- | --- | --- |
| | MRS | PDA | VRBGA | | | | L | a | b | ΔE |
| Raw broccoli | 2.4 ± 0.2 | 2.5 ± 0.1 | 3.4 ± 0.1 | 6.33 ± 0.00 | 4.8 ± 0.2 | 26.9 ± 0.0 | 48.4 ± 0.4 | −13.2 ± 0.1 | 17.2 ± 0.2 | — |
| Day 0 | 8.4 ± 0.2 | <1 | <1 | 4.04 ± 0.00 | 10.7 ± 0.7 | 29.6 ± 0.8 | 48.5 ± 0.7 | −2.1 ± 0.1 | 13.6 ± 0.6 | 11.7 |
| Days 14 | 9.0 ± 0.1 | <1 | <1 | 4.04 ± 0.03 | 12.6 ± 0.8 | 32.5 ± 1.2 | 47.2 ± 1.1 | −1.9 ± 0.5 | 12.4 ± 1.5 | 12.3 |
| Days 28 | 8.0 ± 0.1 | <1 | <1 | 3.95 ± 0.02 | 13.5 ± 0.8 | 32.0 ± 0.7 | 45.9 ± 0.7 | −2.2 ± 0.3 | 13.8 ± 2.5 | 11.8 |
| Days 42 | 7.6 ± 0.1 | <1 | <1 | 3.89 ± 0.03 | 13.8 ± 0.2 | 32.0 ± 0.8 | 46.7 ± 0.2 | −1.5 ± 0.1 | 12.6 ± 0.5 | 12.7 |
| Days 56 | 6.5 ± 0.4 | <1 | <1 | 3.89 ± 0.02 | 13.8 ± 0.5 | 29.9 ± 0.3 | 46.6 ± 0.4 | −1.7 ± 0.1 | 13.1 ± 0.5 | 12.4 |

TABLE 2-continued

Microbiological and physicochemical changes of fermented broccoli during the storage at 4° C.

| | Microbial loads (Log CFU/g) | | | | | | Color | | | |
|---|---|---|---|---|---|---|---|---|---|---|
| | MRS | PDA | VRBGA | pH | TA (g/L) | TP (mg/g, FW) | L | a | b | ΔE |
| Days 70 | 6.3 ± 0.4 | <1 | <1 | 3.86 ± 0.01 | 13.7 ± 0.1 | 31.6 ± 0.2 | 46.7 ± 0.8 | −1.6 ± 0.2 | 12.2 ± 0.4 | 12.7 |
| Days 84 | 6.0 ± 0.8 | <1 | <1 | 3.85 ± 0.01 | 13.8 ± 0.1 | 32.0 ± 0.5 | 47.6 ± 0.9 | −1.9 ± 0.2 | 14.0 ± 0.6 | 11.8 |

Each value was expressed as mean ± standard deviation (n = 3).
"—"not available.
MRS, de Man-Rogosa-Sharpe agar for LAB; PDA, potato dextrose agar for total yeasts and moulds; VRBGA, violet red bile glucose agar for Enterobacteriaceae; TA, titratable acidity; TP: total protein; ΔE: total color difference.

the LAB count in the samples stored at 4° C. remained high (6 log CFU/g) even after storage for 84 days.

The total counts of yeast and moulds in the raw broccoli sample was 2 log CFU/g. The Enterobacteriaceae count in the raw broccoli with 3 log CFU/g. No fungi, moulds and enterobacteria were detected after fermentation or on the fermented samples after storage at both temperature conditions. No pathogenic and spoilage organisms were detected following fermentation and during storage. The results indicate that the fermentation process resulted in a safe and stable product with undetectable level of potentially pathogenic eneterobacteriaceae and spoilage yeast and mould, which maintained high levels of total lactic acid bacteria when stored at 4° C. There are ~$10^6$ CFU/g lactic acid bacteria after ~3 months at 4° C.

Example 3—Assessment of pH and Titratable Acidity After Storage of Lactic Acid Bacteria Fermented Broccoli Florets The pH and titratable acidity (TA) of raw broccoli, fermented broccoli and fermented broccoli after storage at 25° C. and 4° C. was analyzed as described in Example 1. The determination of TA was used to estimate the amount of lactic acid and acetic acid, the main acids produced by lactic acid bacteria, during fermentation. During fermentation, the acids produced by the lactic acid bacteria decrease the pH of the sample. As shown in Table 1, the TA was increased to 10.7 g/L in Day 0 samples. When stored in 25° C., the pH was decreased to 3.87 during storage after 10 days, along with the significantly increased values of TA which reached 14.4 g/L (p<0.05; see Table 1). The results indicate that there were still substrates present for lactic acid bacteria to consume and further produce acid during the early days of storage. Neither the pH nor TA value were significantly changed during the remaining storage period (Table 1).

Decreasing the temperature to 4° C. reduced the rate of decrease of pH and TA in the stored samples due to the decreased activity of the lactic acid bacteria at the lower temperature (see Table 2). After nearly 3 months storage at 4° C., the pH was 3.85 and the TA value was 13.7 g/L.

Example 4—Assessment of Broccoli Maceration and Fermentation on the Conversion of Glucoraphanin into Sulforaphane Broccoli florets were cut into small pieces, mixed with water at 3:2 broccoli:water ratio and the mixture was macerated into a puree using a blender. Puree samples (200 gm) were aliquoted into sterile plastic bottles. The samples were inoculated at $10^8$ CFU/gm with pooled culture of lactic acid bacteria (*Leuconostoc mesenteroides* and *Lactobacillus plantarum*) isolated from Australian broccoli. Samples were incubated in a water bath maintained at 30° C. until the pH dropped to ~4.0, which was attained after four days of fermentation. Control non-inoculated samples were immediately frozen after maceration. A second set of non-inoculated control samples, to which sodium benzoate was added to inhibit microbial growth, were incubated with the inoculated samples at 30° C. for four days until the fermentation of the inoculated samples was completed. Experiments were conducted in triplicate. All samples were kept frozen until sulforaphane and glucoraphanin analysis. As shown in FIG. 1B and Table 3 maceration followed by fermentation increased the sulforaphane yield compared to just maceration and incubation alone.

TABLE 3

Effects of maceration and fermentation on sulforaphane content in broccoli puree.

| 25° C. | SF(mg/kg, DW) | 4° C. | SF (mg/Kg, DW) |
|---|---|---|---|
| Raw material | 149.8 ± 12.4 | Raw material | 149.8 ± 12.4 |
| Control incubated | 86.8 ± 0.6 | Control incubated | 86.8 ± 0.6 |
| 0 days | 278.4 ± 1.8 | 0 days | 278.4 ± 1.8 |
| 10 days | 189 ± 8.8 | 14 days | 288.6 ± 3.1 |
| 20 days | 136.6 ± 6.2 | 28 days | 218.8 ± 4.3 |
| 30 days | 122.2 ± 12.2 | 42 days | 199.4 ± 14.7 |
| 40 days | 116.3 ± 5.0 | 56 days | 190 ± 7.1 |
| 50 days | 112.3 ± 4.0 | 70 days | 190.8 ± 10.7 |
| 60 days | 111.9 ± 11.0 | 84 days | 179.6 ± 10.2 |
| 70 days | 108.8 ± 15.8 | | |
| 80 days | 102.6 ± 14.7 | | |
| 90 days | 87.6 ± 3.7 | | |

Example 5—Assessment of Total Protein Content and Color After Storage of Lactic Acid Bacteria Fermented Broccoli Florets The total protein content and color of lactic acid fermented broccoli florets after fermentation was assessed as described above in the methods section. Compared to raw broccoli (26.9±0.03), the total protein content of fermented broccoli was significantly increased (29.6±0.8 mg/g; p<0.05). This could be due to the high number of lactic acid bacteria inoculated into the sample and the growth during fermentation and protein synthesis by the lactic acid bacteria. The total protein content stayed stable during storage both at 25° C. and 4° C. (Table 1 and Table 2), with no significant difference between samples.

The color values (L, a, b) and the total color difference (ΔE) of broccoli samples are summarized in Table 1 and Table 2. As presented in Table 1 and Table 2, significant differences in the color parameters and the total color difference value (ΔE) were recorded between raw and fermented samples. The L* value (lightness) did not change significantly, whereas a* (greenness) and b* (yellowness) values decreased after the fermentation of broccoli puree. The decrease in a* and b* values may be attributed to the degradation in the color pigmented compounds, such as chlorophyll which would convert to pheophytins under the low pH. The high ΔE value (12.5) of Day 0 sample indicate that the color of broccoli puree was significantly changed after fermentation, which was visually noticeable. During storage (Table 1 and Table 2) there was no significant change in the ΔE value in neither 25° C. nor 4° C. samples.

Broccoli after fermentation with LAB+BP (*Lactobacillus plantarums* B1, B2, B3, B4, B5 and *Leuconostoc mesenteroides* BF1, BF2 isolated from broccoli) had a brighter, more intense green color more similar in color to raw macerated broccoli compared to broccoli fermented with LAB only (the *Lactobacillus plantarums* isolated from broccoli (B1, B2, B3, B4, B5)).

Example 6—Changes of Total Phenolic Content and Antioxidant Activity of Lactic Acid Bacteria in Fermented Broccoli Florets The total phenolic content (TPC) and antioxidant activity of lactic acid fermented broccoli florets after fermentation was assessed as described above in the methods section. The TPC of raw broccoli was 127.6±12.4 mg GAE/100 g (FIG. 3A) of fresh weight. The values of TPC on Day 0 significantly increased to 236.9±23.4 mg GAE/100 g ($p<0.05$) compared to raw broccoli. There was no significant difference between samples stored at 25° C. and 4° C. in the TPC after storage (FIG. 3A). When stored at 25° C., the value of TPC in fermented broccoli was 246.2±19.3 mg GAE/100 g on Days 10, and 248.1±25.0 mg GAE/100 g on Days 90. When stored at 4° C., the values of TPC was 274.1±20.2 and 267.2±3.3 mg GAE/100 g for Days 14 and Days 84, respectively.

The antioxidant activities of sample expressed as ORAC values are shown in FIG. 3B. The ORAC value of the raw sample was 110.1±0.05 μmol TE/g. Fermentation significantly increased the ORAC value by ~70% to 186.9±3.3 μmol TE/g when compared to raw broccoli. This result suggested that antioxidant compounds may have increased during fermentation and was consistent with the change in TPC after fermentation.

During storage, the antioxidant activity of fermented broccoli did not change significantly. As shown in FIG. 3B, when stored at 25° C., the values of ORAC at Days 10 and Days 90 were 173.0±14.4 and 150±5.5 μmol TE/g, respectively. Similar results were obtained for samples stored at 4° C. The ORAC value was 172.0±15.5 μmol TE/g at the beginning of storage, which increased to a maximum value of (188.7±12.9 μmol TE/g) after storage.

Example 7—Assessment of Fermentation Time for Different Combinations of Lactic Acid Bacteria Macerated broccoli was prepared as described above in the methods section with a broccoli to water ratio of 3:2 and a maceration time of 1 min. The broccoli material was inoculated with either $10^7$ CFU/g or $10^8$ CFU/g with one of: LGG, LAB (*Lactobacillus plantarum* (B1, B2, B3, B4, B5) isolated from Australian broccoli, LAB+LP (*Lactobacillus plantarum* isolated from broccoli and *Lactobacillus* sp. ATCC 8014), BP (*Leuconostoc mesenteroides* isolated from broccoli), LAB+BP (a mixture of the two groups as described in the methods sections) and fermented at either 25° C., 30° C. or 34° C. to reach a target pH of 4.4. As shown in FIG. 4 the addition of lactic acid bacteria isolated from broccoli and/or broccoli puree significantly reduced the time taken for the fermentation with the combination of LAB+BP reaching a pH of 4.4 after fermenting for about 4 days. An example composition of fermented broccoli product is shown in Table 4.

TABLE 4

Composition of the fermented broccoli product.

| Quality attributes | Value |
|---|---|
| Total fibre | ~29.5 g/100 gdw |
| ORAC antioxidant capacity | 18695 μmol TE/100 gdw |
| Total polyphenol content | 2369 mg GAE/100 gdw |
| Total titratable acidity | 1.1% lactic acid equiv. |
| Lactic acid bacteria count | ~$10^8$ CFU/gm |
| Total protein | 30 g/100 gdw |
| Broccoli to water ratio in puree by mass | 3 to 2 |

Example 8—Effect of Storage on Sulforaphane Content of Fermented Broccoli

FIG. 2A shows the effects of storage at 4 and 25° C. on sulforaphane content of fermented broccoli puree. As can be seen in the FIG. 2A, the sulforaphane content of samples stored at 25° C. dramatically decreased to 770.7±34.9 μmol/kg (a 52% loss) after 20 days storage, followed by a slower decline during the rest of the storage period, reaching a total loss of 69.5%. Interestingly, no statistically significant change in sulforaphane content was observed during the first 2 weeks of storage of fermented broccoli samples at 4° C. A significant decrease of ~23.7% occurred during the subsequent two weeks followed by a slow degradation during the rest of the storage period. At the end of the storage (Day 84), the sulforaphane content was 1012.9±57.6 μmol/kg in samples stored at 4° C., making the total loss of sulforaphane ~37.4% compared to the Day 0 samples. The sulforaphane content during the first two weeks of storage was maintained perhaps due to simultaneous production and degradation of sulforaphane since some decrease in glucoraphanin content was observed in the 4° C. stored samples over the same period.

Example 9—Effect of Fermentation and Storage on Glucoraphanin Content

FIG. 7 shows the effect of maceration and fermentation on glucoraphanin content and its stability during storage at 4° C. and 25° C. The glucoraphanin content of raw broccoli was 3423.7±39.7 μmol/kg (FIG. 7), After fermentation, the glucoraphanin content sharply decreased to 712.4±64.2 μmol/kg (Day 0 sample). Glucoraphanin is relatively stable in intact tissue and the degradation in this case can be attributed to myrosinase catalyzed hydrolysis due to increased enzyme-substrate interaction in the macerated tissue during fermentation. The period of sharp decrease in glucoraphanin coincided with the fermentation period.

No significant change in glucoraphanin content was observed in fermented samples during storage at 25° C. and 4° C. However, slightly higher glucoraphanin content was observed in samples stored at 25° C. This could be related to the faster decline in pH of the samples stored at 25° C. (pH 3.87 at the second time point) compared to samples stored at 4° C. (pH 4.04 at the second time point). The optimal pH for myrosinase catalyzed hydrolysis of glucoraphanin ranges from 5 to 6 decreasing to the lowest value at pH 3.0 (Dosz & Jeffery, 2013). The relatively higher pH of the samples stored a 4° C. may have contributed to the slightly higher degradation of glucoraphanin during storage at 4° C. compared to 25° C.

Example 10—Assessment of Heat Treatment Conditions to Maximise Conversion of Glucoraphanin into Sulforaphane in Broccoli Matrix Broccoli florets packed in retort pouches were subjected to thermal processing at temperatures ranging from 60° C. to 80° C. and treatment times of 0 to 5 minutes. The treatment involved pre-heating to the experimental temperature in a water bath maintained at 5° C. higher than the experimental temperature followed by incubation in a second water bath maintained at the experimental temperature. Following thermal treatment, samples were cooled in ice-water and were macerated with water added at 2:3 water to broccoli ratio as described above. The macerated samples were incubated for 1 hr at 30° C. and kept frozen until sulforaphane analysis. Results are shown in FIG. 2B and Table 5. As shown in Table 5 pre-heating the sample at 60° C., 65° C. or 80° C. followed by maceration increased the sulforaphane yield relative to raw broccoli floret which was macerated without pre-heating.

used in the pre-heating experiments. Two types of pre-heating experiments were conducted; in-pack processing and direct water blanching. In the case of the in-pack experiments, broccoli florets were packed in retort pouches (Caspak Australia, Melbourne), sealed and pre-heated for various time points in a thermostated water batch maintained at 60° C., 65° C. and 80° C. The temperature of the broccoli samples at the slowest heating point was measured by using a thermometer. Time 0 was defined as the time for the core temperature to reach the designated experimental temperature. The treatment time were 0, 1, 3, and 5 min for 60° C. and 65° C. and 0, 1, 2, 3 min for 80° C. With the direct water-blanching experiments, the broccoli florets were immersed in Milli-Q water in a glass beaker that was heated in a thermosated water-bath. The direct water blanching experiments were conducted at 60° C. and 65° C. The temperature of the broccoli samples was continuously measured using a thermometer and timing started once the temperature at the slowest heating point attained the designated experimental temperature as described above. All thermal treatment experiments were carried out in triplicate. Unheated broccoli florets were used as controls Immediately following the heat treatment, the samples were cooled in ice water and were homogenized with Milli-Q water in ratio of 3 parts broccoli to 2 parts of water for 1 min using a kitchen scale magic bullet blender (Nutribullet pro 900 series, LLC,

TABLE 5

Effects of heat treatment on sulforaphane production in broccoli matrix.

| Temperature | Heat treatment time (minute) | Sulforaphane (μmol/kg, DW) | Sulforaphane (mg/kg, DW) | Sulforaphane (mg/g, DW) |
|---|---|---|---|---|
| Raw broccoli floret | — | 817.5 ± 9.29 | 145 ± 1.6 | 0.145 ± 0.002 |
| 60° C. | 0 | 2343.5 ± 124.1 | 415.5 ± 22.0 | 0.415 ± 0.022 |
| | 1 | 2661.5 ± 10.9 | 471.9 ± 1.9 | 0.472 ± 0.002 |
| | 3 | 2780.9 ± 270.7 | 493.0 ± 48.0 | 0.493 ± 0.048 |
| | 5 | 3147.6 ± 148 | 558.1 ± 26.2 | 0.558 ± 0.026 |
| 65° C. | 0 | 3585.9 ± 119.2 | 635.8 ± 21.1 | 0.636 ± 0.021 |
| | 1 | 3673 ± 144.8 | 651.2 ± 25.7 | 0.651 ± 0.026 |
| | 3 | 3983.4 ± 30.5 | 706.3 ± 5.4 | 0.706 ± 0.005 |
| | 5 | 3620.1 ± 240.7 | 641.8 ± 42.7 | 0.642 ± 0.043 |
| 80° C. | 0 | 1451.5 ± 43.5 | 257.3 ± 7.7 | 0.257 ± 0.008 |
| | 1 | 1446.8 ± 17.5 | 256.5 ± 3.1 | 0.257 ± 0.003 |
| | 2 | 1043.1 ± 94.2 | 184.9 ± 16.7 | 0.185 ± 0.017 |
| | 3 | 981.2 ± 35.1 | 174 ± 6.2 | 0.174 ± 0.006 |

Example 11—Assessment of Preheating Prior to Lactic Acid Bacterial Fermentation on the Sulforaphane Content of Broccoli This study evaluated the impact of mild preheating treatment of broccoli florets to inactivate the Epithiospecifier protein (ESP) combined with lactic acid bacteria on sulforaphane content of broccoli puree.
Materials
Broccoli (cv. 'Viper') was purchased from a local supermarket (Coles, Werribee South, VIC, Australia). DeMan-Rogosa-Sharp (MRS) broth (1823477, CM0359, Oxoid) was purchased from Thermo Fisher Scientific (Australia). DL-Sulforaphane was purchased from Sigma-Aldrich (St. Louis, Missouri, USA). All the other chemical and biochemical reagents were analytical grade or higher and were purchased from local chemical vendors.
Experiments to Optimize the Mild Pre-Heating Conditions to Maximize Sulforaphane Yield
Broccoli florets were cut at approximately 2 cm below the head, and each 30 g of randomly mixed broccoli florets were USA). The homogenized samples were incubated in the dark for 4 h at 25° C. to allow the enzymatic hydrolysis of glucoraphanin. After incubation, all the samples were frozen in −20° C. until sulforaphane analysis.
Preparation of Starter Cultures
Pooled cultures of *Leuconostoc mesenteroides* (BF1, BF2) and *Lactobacillus plantarum* (B1, B2, B3, B4, B5) isolated from broccoli as described in the methods in Example 1. were used in the fermentation experiments. The lactic acid bacteria stock cultures, which were stored at −80° C., were activated by inoculation into 10 mL MRS broth (Oxoid, Victoria, Australia) and incubation at 30° C. for 24 hours to get the primary inoculum. 2 mL of the primary cultures were inoculated into 200 mL of MRS broth to obtain the secondary cultures. After 24 h incubation, the 6 secondary cultures were centrifuged, washed twice with sterile phosphate buffer saline (PBS) and each of the culture was resuspended in Milli-Q water at a concentration of 10 log colony-forming units per millilitre (CFU/mL) to obtain an initial biomass of 8 log CFU/mL in 100 gm broccoli puree samples. The *L. plantarum* cultures were mixed with the *L.*

*mesenteroides* cultures at 1:1 proportion prior to inoculation into the broccoli puree samples.

Sample Preparation

Broccoli florets were cut at approximately 2 cm below the crown and were separated into two lots; heat treated and non-treated. After heat treatment at the optimal condition selected based on the results of the experiments as described above, the samples were cooled in ice-water, shredded and homogenized with Milli-Q water in ratio of 3:2 for 1 min using a kitchen scale magic bullet blender (Nutribullet pro 900 series, LLC, USA). The non-treated broccoli were also homogenized in a similar way. The broccoli puree, after mixing well, was aliquoted into sterile plastic containers (100 mL) with screw lids (Technoplast Australia) for further experiments.

Fermentation

Broccoli puree samples (pre-heated and untreated) were inoculated with the LAB culture prepared as described above in this example. Preheating of broccoli florets was conducted in-pack at 65° C. for 3 min based on the result of the experiment to optimise the pre-heating condition. In order to evaluate the impact of acidification without fermentation on conversion of glucoraphanin into sulforaphane, acidification experiments were conducted on pre-heated and untreated broccoli puree using glucono-delta-lactone (GDL) to attain the pH of the fermented broccoli puree. Preheated broccoli puree and untreated broccoli puree without further treatment were used as controls.

For the fermentation experiment, each broccoli puree sample was inoculated with the prepared starter culture at an initial level of 8 log CFU/g. The fermentation experiment was carried out at 30° C. until the pH reached ~4.0 after 15 hrs of incubation. Once the fermentation was completed, 3 samples (day 0 samples) of each fermented group were taken and stored at −20° C. until analysis. The rest of the ferments were randomly separated into two lots for the storage trials: one lot was stored under refrigerated condition (4° C.) and the second lot was stored at 25° C. for the assessment of the sulforaphane stability of the samples after 14 days storage. Similarly, the untreated broccoli puree, preheated broccoli puree and the preheated-GDL treated broccoli puree were also sampled at time zero and stored at 25 and 4° C. for the 14 days storage trials. After 14 days storage, all the samples were frozen and kept at −20° C. until sulforaphane analyses.

Sulforaphane Analysis and Statistical Analysis

Was performed as described in Example 1.

Optimization of Heat Treatment Conditions for Improving Sulforaphane Yield

The influence of heat treatment on the formation of sulforaphane of the heated-in-pack broccoli florets at three different temperatures (60, 65 and 80° C.) for various processing times (0, 1, 3 and 5 min for 60 or 65° C.; 0, 1, 2 and 3 min for 80° C.) are shown in FIG. 5A. The results showed that compared to the raw broccoli the sulforaphane yield increased in all of the heat treated samples. Time 0 designate samples that were heated until their core reached the experimental temperature.

As shown in FIG. 5A, an increase in sulforaphane yield occurred when the packed broccoli samples were heated at 60° C. for 0, 1, 3, and 5 min. The concentration of sulforaphane in these samples were 2343.5±124.1, 2661.5±10.9, 2780.9±270.8, and 3147.7±148.0 µmol/kg DW, respectively. On the other hand, when broccoli was processed at 65° C., the sulforaphane yield initially increased with processing time from 3585.9±119.2 (0 min) to the highest value of 3983.4±30.5 µmol/kg DW (3 min). Further increase in treatment time resulted in lower yield with the lowest value of 3620.1±240.7 µmol/kg observed after 5 min treatment time. In contrast to treatments at 60 and 65° C., for samples that were processed at 80° C., a steady decrease in sulforaphane yield was observed with longer treatment times; with sulforaphane content of 1451.5±43.5, 1446.8±17.5, 1043.1±94.2, and 981.2±35.1 µmol/kg DW after 0 min, 1 min, 2 min and 3 min treatment respectively. Overall, the highest yield of sulforaphane (3983.4±30.5 µmol/kg) for in-pack treatment of broccoli was obtained for samples pre-heated at 65° C. for 3 min, which is ~5 fold higher than raw broccoli (817.5±9.3 µmol/kg DW). In contrast, heating broccoli directly in water, generally resulted in a lower yield of sulforaphane compared to in-pack processing as shown in FIG. 5B. For direct water blanching at 60° C., the sulforaphane yield increased with treatment time from 1698.00±121.9 µmol/kg DW (0 min), to 2833.3±118.6 µmol/kg DW (1 min) and then steadily decreased to the lowest value of 2345.8±57.7 µmol/kg DW for 5 min treatment at 60° C. A sharp drop in sulforaphane yield compared to 60° C. was observed when samples were blanched at 65° C. The sulforaphane yield was 503.7±23.8 mol/kg DW of broccoli after 5 min thermal treatment at 65° C., which was even lower than the value obtained for raw broccoli. The reason could be the leaching of glucoraphanin into the blanching water resulting in low yield of sulforaphane. For direct water blanching, the optimum treatment temperature for maximizing sulforaphane yield was 60° C. compared to 65° C. for the in-pack processing.

In this study, the highest yield of sulforaphane was obtained for broccoli florets processed in-pack for 3 min at 65° C., indicating that the condition favors the inactivation of ESP to a larger extent while maintaining sufficient myrosinase activity resulting in optimal conversion into sulforaphane. Under this condition, it seems that most of the extractable glucoraphanin is converted to sulforaphane assuming 1 to 1 conversion, since the glucoraphanin content of the broccoli samples were determined to be 3423.7±39.7 µmol/kg DW.

The observation that the exposure of the heat-treated broccoli to fermentation resulted in higher levels of sulforaphane than would be predicted from the level of extractable glucoraphanin from raw broccoli suggests heat-treatment may have increased the accessibility of glucoraphanin to myrosinase, resulting in higher sulforaphane yield than would be expected based on the quantifiable amount of glucoraphanin present in the untreated broccoli.

Less sulforaphane yield was obtained for broccoli florets directly blanched in water, most probably due to leaching into the blanching water, since glucoraphanin is soluble in water. It is also interesting to note that when broccoli florets were heated directly in water, the maximum amount of sulforaphane was obtained by heating at 60° C. for 1 min compared to 65° C. for 3 min when heat treatment of broccoli florets was done in-pack. This may be due to the higher leaching rate into the blanching water at 65° C. which counteracted the effects of higher level of inactivation of ESP at 65° C.

The Effect of LAB Fermentation and Chemical Acidification on Sulforaphane Yield

Broccoli florets were pre-heated in-pack at the best treatment condition selected above (65° C., 3 min). Samples were then either fermentation by lactic acid bacteria or acidified using the acidulant (GDL). Consistent with the pre-treatment experiments, the sulforaphane value of broccoli significantly increased ($p<0.05$) after the heat treatment; with 806.2±7.0 µmol/kg DW and 3536.0±136.9 µmol/kg DW of sulforaphane yield for raw and pre-heated broccoli, respectively. The value of 3536 μmol/kg DW obtained with this separate batch of broccoli preheated prior to fermentation is of the same order obtained when a different batch of broccoli was used, where 3983 μmol/kg DW was obtained indicating slight batch to batch variation.

As shown in Table 6, after the fermentation, the sulforaphane content of broccoli samples varied depending on the treatment of the broccoli prior to fermentation. The sulforaphane content of raw broccoli puree after fermentation (1617.4±10.2 μmol/kg DW) was approximately twice the sulforaphane content of raw broccoli puree. Pre-heating of broccoli prior to pureeing resulted in much higher increase in sulforaphane content after fermentation. The sulforaphane content of preheated-fermented broccoli (13121.3±440.8 μmol/kg DW) was about 8 times of the raw-fermented broccoli puree. The observed sulforaphane yield after the combined preheating-fermentation treatment is much higher than what would be expected based on the quantifiable amount of glucoraphanin (3423.7±39.7 μmol/kg) in the raw broccoli sample. It seems that the combined preheating and fermentation process enhances the release and accessibility of glucoraphanin for conversion over and above the inactivation of ESP by the pre-heating process. The pre-heating process coupled with microbial cell wall degrading enzymes may have enhanced the disruption of the cell compartment and release of bound glucosinolates in the matrix, that were not extractable or accessible in the raw broccoli. Some lactic acid strains produce polysaccharide degrading enzymes such as cellulases and pectinases capable of degrading the cell wall structure and enhance the release of wall bound components.

In contrast, chemical acidification of preheated broccoli puree by GDL resulted in a significantly lower ($p<0.05$) content of sulforaphane compared to pre-heated and preheat-fermented samples (Table 6). The sulforaphane content of the GDL acidified samples were 2169.4±176.0 μmol/kg DW, which is 40% lower than the preheated broccoli sample (3536.0±136.9 μmol/kg DW) ($P<0.05$). It appears that the fast reduction to pH 4.04 during acidification may have reduced the conversion of glucoraphanin into sulforaphane in the GDL samples. It is well known that the conversion of glucosinolates is highly dependent on pH and acidic pH favours conversion into nitriles (Latte et al., 2011).

In the case of the pre-heated fermented samples, the acidification occurs gradually over a period of >15 hr enabling the conversion of glucoraphanin mainly to sulforaphane since the activity of ESP is expected to be significantly reduced after preheating at 65° C. for 3 min.

Changes of Sulforaphane Content During Storage

The concentration of sulforaphane of all the samples declined after 14 days storage at 25° C. (see Table 6 and FIG. 6). Interestingly, an increase in sulforaphane content was observed in all samples except the fermented samples during 14 days storage at 4° C. The sulforaphane content of the raw puree almost doubled during storage at 4° C. Similarly, the sulforaphane content of the pre-heated samples increased by ~2.6 times whereas the sulforaphane content of the pre-heated GDL samples increased by ~2.3 times, which suggests continuous release of glucoraphanin from the matrix during storage allowing further conversion to sulforaphane and increase in concentration counteracting the consequence of sulforaphane degradation during storage. With respect to the preheated-fermented samples, reduction in sulforaphane content was observed during storage at both temperatures. All the accessible glucoraphanin may have been converted to sulforaphane during fermentation so much so that no further conversion occurred during storage but rather degradation albeit to a different extend depending on the temperature. As such, only a slight decline (~6%) was observed during storage at 4° C. whereas the decline during storage at 25° C. was ~70%.

This study showed that pre-heating coupled with lactic acid bacteria fermentation substantially enhances the sulforaphane content of broccoli based products. In-pack pre-heating treatment of broccoli florets at 65° C. for 3 min followed by maceration and fermentation resulted in as much as ~16 times higher yield of sulforaphane compared to raw broccoli puree. Preheating under this condition increased the sulforaphane yield in broccoli puree from 806 μmol/KgDW (dry weight) in the untreated broccoli to 3536 μmol/KgDW, indicating that the treatment substantially inhibits ESP while maintaining sufficient myrosinase activity for the conversion of glucoraphanin into sulforaphane. The best preheating condition during direct water blanching was 1 min at 60° C. and resulted in sulforaphane yield of 2833 μmol/KgDW. The lower yield during direct blanching can be attributed to leaching of the water-soluble glucoraphanin into the blanching media. Preheating of broccoli florets in-pack (65° C./3 min) combined with lactic acid bacteria fermentation further enhanced the sulforaphane content to 13121 μmol/KgDW, which is ~16 times increase compared to raw broccoli. Chemical acidification of in-pack preheated (65° C., 3 min) combined with acidification of the broccoli puree by glucono-delta-lactone resulted in sulforaphane yield of 2169 μmol/KgDW, which is lower than pre-heating alone. The sulforaphane content of the pre-heated-fermented puree remained stable (~94% retention) during two weeks storage at 4° C.

TABLE 6

Sulforaphane yield (μmol/Kg DW) of broccoli before and after processing.

| | Sulforaphane (μmol/kg, DW) | | | | |
|---|---|---|---|---|---|
| | Raw | Raw-Fermented | Preheatnot GDL | Preheat GDL | Preheat-Fermented |
| Day 0 | 806.2 ± 7.0 | 1617.4 ± 10.2 | 3536.0 ± 136.9 | 2169.4 ± 176.0 | 13121.3 ± 440.8 |
| Days 14_4° C. | 1409.8 ± 82.7 | 1627.7 ± 17.5 | 9149.4 ± 63.6 | 4994.8 ± 291.2 | 12301.3 ± 443.5 |
| Days 14_25° C. | 1268.2 ± 0.1 | 1065.8 ± 49.8 | 3338.2 ± 93.9 | 2593.1 ± 97.7 | 3974.2 ± 71.2 |

DW: dry weight, GDL: acidified using glucono-delta-lactone. Preheating was conducted at 65° C. in pack for 3 minutes.

Example 12—Effect of Lactic Acid Bacteria Fermentation on Polyphenolic Profile of Broccoli In order to determine the effects of fermentation on the polyphenolic metabolites of broccoli samples, targeted liquid chromatography-mass spectrometry (LC-MS) based metabolomic analysis of the raw and fermented broccoli puree samples was conducted. The resulting multivariate data was analysed using Metaboanalyst software (Metaboanalyst 3.0, Xia and Wishart, 2016). Fermentation resulted in a significant change in the metabolite profile of the broccoli samples. The partial least square discriminant analysis (PLS-DA) of the data shows a clear distinction between the polyphenolic profile of the fermented and the non-fermented samples (FIG. 8).

The top 15 metabolites that were identified to be responsible for the differences between the two groups are shown in FIG. 9. They are phenolic acids and phenolic aglycones, with higher bioactivity and bioavailability compared to their phenolic acid ester and phenolic glycoside precursors. The concentrations of most of these metabolites showed substantial increase following fermentation indicating the beneficial effect of fermentation on the polyphenol profile of broccoli puree. The fold changes for some of the metabolites are shown in Table 7.

A substantial increase in sinapic acid and kaempferol, 24 fold and 16 fold respectively was observed following fermentation. Similarly, fermentation induced an 8 fold increase in chlorogenic acid and phenyllactic acid. The concentrations of hesperetin, quercetin, methyl syringate and syringic acid also increased substantially after fermentation. The increase in the concentration of aglycones such as kaempferol, hesperetin and quercetin can be attributed to conversion of their glycoside precursors by the activity of microbial glycosidases. The increase in the concentration of phenolic acids such as sinapic acid could be due to the conversion of phenolic acid esters in broccoli by the activity of microbial esterases. Some decrease in caffeic acid and gallic was observed following fermentation. The activity of microbial decarboxylases convert caffeic acid into the corresponding vinyl catechol and gallic acid into pyrgallol, which may be responsible for the decrease in their concentration (Filanino et al., 2015; Guzman-Lopez et al., 2009).

TABLE 7

Fold changes in the top 13 polyphenols responsible for differences between fermented and non-fermented broccoli puree.

| | Compounds | Fold change (FC) | Log$_2$(FC) |
|---|---|---|---|
| 1 | Sinapic acid | 24.1 | 4.6 |
| 2 | Kaempferol | 16.1 | 4.0 |
| 3 | Chlorogenic acid | 8.3 | 3.1 |
| 4 | Phenyllactic acid | 7.9 | 3 |
| 5 | Hespertin | 3.7 | 1.9 |
| 6 | Methyl syringate | 3.3 | 1.7 |
| 7 | Syringic acid | 3.3 | 1.7 |
| 8 | Caffeic acid | 0.32 | −1.6 |
| 9 | Ferullic acid | 2.7 | 1.4 |
| 10 | 4, hydroxybenzoic acid | 0.4 | −1.4 |
| 11 | Quercetin | 2.6 | 1.3 |
| 12 | Rutin | 2.5 | 1.3 |
| 13 | Gallic acid | 0.5 | −1.1 |

Example 13—Identification of Metabolites Produced by Lactic Acid Bacteria Fermentation of Broccoli by Targeted and Untargeted LC MS Analyses of Samples The fermented and non-fermented broccoli puree samples were frozen and freeze dried. The samples (100 mg freeze dried powder each) were extracted using 1 ml of ice-cold methanol and Milli-Q water (50:50, v:v), which comprised 100 mg/ml of caffeine as an internal standard. The samples were then vortexed for 2 minutes prior to being sonicated (40 Hz) for 30 minutes. Samples were then centrifuged at 20,000 rpm at 4° C. for 30 minutes, and the supernatant transferred to clean silanised LC-MS vials. Samples were analyzed by injecting 1.4 μl into an Agilent 6410 LC-QQQ HPLC (Agilent Technologies, Santa Clara, California, USA). The analyses were performed using a reversed-phase Agilent Zorbax Eclipse Plus C18, Rapid Resolution HD, 2.1×50 mm, 1.8 um (Agilent Technologies, Santa Clara, California, USA), with a column temperature of 30° C. and a flow rate of 0.3 ml/min. The mobile phase was operated isocratically for 1 min 95:5 (A:B) then switched to 1:99 (A:B) for a further 12 min before returning back to 95:5 (A:B) for an additional 2 min; providing a total run time of 15 min Mobile phase 'A' consisted of 100% H$_2$O and 0.1% formic acid, and mobile phase 'B' contained 75% acetonitrile, 25% isopropanol and 0.1% formic acid. The MS was collecting data in the mass range 50-1000 m/z. Qualitative identification of the compounds was performed according to the Metabolomics Standard Initiative (MSI) Chemical Analysis Workgroup using several online LC-MS metabolite databases, including Massbank and METLIN. Overall, the instrumental conditions were similar for both positive electrospray (±ESI) and negative electrospray (-ESI) modes. Scan time was 500, the source temperature was maintained at 350° C., the gas flow was 12 L/min and the nebuliser pressure was 35 psi.

For the identification of compounds in the untargeted analysis, the criteria was set at >90% match rate. Where the match rate dropped to between 70-89%, the compounds are identified with brackets (for example, if a compound was between 70-89% they are annotated as "<name>"). Any matches below 70% were removed. In total, there was ca. 1000-1500 fatures to identify; many were poorly matched (and removed) or were less than 10×S/N ratio from the baseline. As such, the compounds/peaks used were actual peaks and the IDs are fairly strong (i.e. >70%).

Untargeted LC-MS metabolomics study showed a 2 to 360 fold increase in certain polyphenolic glycosides including anthocyanin glycosides, phenolic acid glycosides, phenolic acids, a 5 to 60 fold increase in some glucosinolates with glucoraphanin increasing 27 fold and about a 3 to 4 fold increase in indol-3carbinol and ascorbigen. Results are summarised in Table 8 and are shown in FIG. 10 and in a volcano plot in FIG. 11. The top 50 metabolites that increased after fermentation include several polyphenol glycosides and glucosinolates indicating that the process enhances their extractability and bioaccessibility.

TABLE 8

Fold changes in different metabolites between fermented and non-fermented broccoli puree based on untargeted LC-MS analysis.

| Metabolite | FC | log2(FC) | raw. pval | (−LOG10(p)) |
|---|---|---|---|---|
| Benzoic acid | 4670.1 | 12.189 | 5.50E−08 | 7.2593 |
| Cyanidin 3-O-rutinoside | 361.03 | 8.496 | 0.011951 | 1.9226 |
| Cyanidin 3-O-6"-p-coumaroyl-glucoside | 271.87 | 8.0868 | 0.011465 | 1.9406 |

TABLE 8-continued

Fold changes in different metabolites between fermented and non-fermented broccoli puree based on untargeted LC-MS analysis.

| Metabolite | FC | log2(FC) | raw. pval | (−LOG10(p)) |
|---|---|---|---|---|
| molybdopterin | 149.51 | 7.2241 | 0.00915 | 2.0386 |
| 5-methylthiopentylglucosinolate | 59.335 | 5.8908 | 0.005835 | 2.234 |
| 5-methylthioribulose 1-phosphate | 46.001 | 5.5236 | 0.000334 | 3.4757 |
| Ellagic acid arabinoside | 42.956 | 5.4248 | 0.002845 | 2.546 |
| thiamine phosphate | 42.436 | 5.4072 | 0.005123 | 2.2905 |
| 2-carboxy-D-arabinitol 1-phosphate | 41.06 | 5.3597 | 0.013093 | 1.883 |
| N-acetyl-D-glucosamine 1,6-bisphosphate | 40.636 | 5.3447 | 0.001824 | 2.739 |
| S-norreticuline | 32.883 | 5.0393 | 0.000362 | 3.4412 |
| 5-formamido-1-5-phospho-D-ribosyl-imidazole-4-carboxamide | 30.585 | 4.9348 | 8.28E−06 | 5.0817 |
| 4-methylumbelliferone 6'-O-malonylglucoside | 30.436 | 4.9277 | 0.001329 | 2.8765 |
| Hydroxytyrosol 4-O-glucoside | 28.971 | 4.8565 | 0.001319 | 2.8798 |
| glucoraphanin | 27.475 | 4.7801 | 0.014685 | 1.8331 |
| glucobrassicin | 26.746 | 4.7413 | 0.00441 | 2.3556 |
| 5-hydroxy-CMP | 25.864 | 4.6929 | 0.004277 | 2.3689 |
| 4alpha-formyl,4beta,14alpha-dimethyl-9beta,19-cyclo-5alpha-ergost-24241-en-3beta-ol | 18.8 | 4.2326 | 0.003497 | 2.4563 |
| indole-3-acetyl-phenylalanine | 17.44 | 4.1243 | 2.37E−06 | 5.6245 |
| N-hydroxypentahomomethionine | 16.92 | 4.0807 | 0.000559 | 3.2529 |
| Cyanidin 3-O-arabinoside | 16.098 | 4.0088 | 0.000413 | 3.3837 |
| tetrahydrobiopterin | 15.412 | 3.946 | 0.015746 | 1.8028 |
| orotidine 5'-phosphate | 14.737 | 3.8813 | 0.001699 | 2.7699 |
| 2-2'-methylthiopentylmaleate | 14.621 | 3.87 | 0.005417 | 2.2662 |
| S-adenosyl 3-methylthiopropylamine | 14.564 | 3.8644 | 0.00177 | 2.752 |
| 4-methylthiobutyl glucosinolate | 14.183 | 3.8261 | 0.011178 | 1.9516 |
| salicylate | 13.59 | 3.7644 | 0.000221 | 3.6556 |
| N-hydroxyhomomethionine | 12.902 | 3.6896 | 0.004311 | 2.3654 |
| 4'-phosphopantetheine | 11.775 | 3.5576 | 0.003073 | 2.5124 |
| 5-phospho-beta-D-ribosylamine | 10.643 | 3.4119 | 0.003185 | 2.497 |
| D-erythro-imidazole-glycerol-phosphate | 10.288 | 3.3629 | 0.019147 | 1.7179 |
| a reduced flavodoxin | 10.108 | 3.3374 | 0.005373 | 2.2698 |
| Cyanidin 3-O-6''-dioxalyl-glucoside | 9.9207 | 3.3104 | 0.000299 | 3.5242 |
| 8-oxo-GMP | 9.8883 | 3.3057 | 0.008524 | 2.0694 |
| 3-dehydroteasterone | 8.985 | 3.1675 | 8.33E−09 | 8.0793 |
| indolylmethylisothiocyanate | 7.7651 | 2.957 | 0.018337 | 1.7367 |
| choline | 7.7212 | 2.9488 | 0.023412 | 1.6306 |
| carbamoyl phosphate | 7.7098 | 2.9467 | 0.009139 | 2.0391 |
| homogentisate | 7.6608 | 2.9375 | 0.00153 | 2.8153 |
| S-adenosyl-L-methionine | 7.3817 | 2.8839 | 2.85E−05 | 4.5445 |
| oxaloacetate | 7.3494 | 2.8776 | 0.000538 | 3.2694 |
| urate | 7.2329 | 2.8546 | 0.000803 | 3.0951 |
| coniferaldehyde glucoside | 7.1826 | 2.8445 | 0.016973 | 1.7702 |
| pyridoxal 5'-phosphate | 7.0734 | 2.8224 | 0.021829 | 1.661 |
| dTMP | 6.9501 | 2.797 | 0.018743 | 1.7272 |
| 2-oxoglutarate | 6.8749 | 2.7813 | 0.00019 | 3.7216 |
| coniferaldehyde | 6.6643 | 2.7365 | 1.46E−05 | 4.8345 |
| Petunidin 3-O-rhamnoside | 6.0484 | 2.5965 | 0.002487 | 2.6043 |
| 6-phospho D-glucono-1,5-lactone | 5.8171 | 2.5403 | 0.019384 | 1.7126 |
| dTDP | 5.6526 | 2.4989 | 0.000837 | 3.0774 |
| propane-1,3-diamine | 5.5793 | 2.4801 | 0.001873 | 2.7275 |
| benzoate | 5.4402 | 2.4437 | 0.005218 | 2.2825 |
| xi-progoitrin | 5.091 | 2.3479 | 0.000107 | 3.9715 |
| 2-phospho-D-glycerate | 5.0613 | 2.3395 | 0.001146 | 2.941 |
| R-4'-phosphopantothenoyl-L-cysteine | 4.8855 | 2.2885 | 0.01357 | 1.8674 |
| L-arogenate | 4.782 | 2.2576 | 0.018843 | 1.7248 |
| L-phenylalanine | 4.5585 | 2.1886 | 0.000213 | 3.671 |
| Phenol | 4.4651 | 2.1587 | 0.002537 | 2.5956 |
| Gardenin B | 4.3888 | 2.1338 | 0.012372 | 1.9076 |
| glucomalcommin | 4.1855 | 2.0654 | 0.014526 | 1.8378 |
| Sulfachloropyridazine | 4.1627 | 2.0575 | 0.013676 | 1.864 |
| 4-methyl-2-oxopentanoate | 3.906 | 1.9657 | 0.004372 | 2.3593 |
| ascorbigen | 3.7819 | 1.9191 | 0.017398 | 1.7595 |
| 2-naphthol | 3.6366 | 1.8626 | 0.01404 | 1.8526 |
| Medioresinol | 3.6131 | 1.8532 | 0.007717 | 2.1125 |
| E-2-pentenol | 3.5473 | 1.8267 | 0.012466 | 1.9043 |
| N-feruloyltyramine | 3.3648 | 1.7505 | 0.004573 | 2.3399 |
| 2-methyl-6-phytyl-1,4-benzoquinol | 3.3442 | 1.7417 | 0.000245 | 3.6101 |
| pyridoxal | 3.0278 | 1.5983 | 0.00016 | 3.7954 |
| 1D-myo-inositol 1-monophosphate | 2.784 | 1.4771 | 0.005472 | 2.2618 |
| N-monomethylethanolamine | 2.7546 | 1.4618 | 1.55E−05 | 4.8092 |
| 3,4-Dicaffeoylquinic acid | 2.7368 | 1.4525 | 0.012553 | 1.9013 |
| Cirsilineol | 2.6151 | 1.3868 | 0.001515 | 2.8197 |
| S-methylmalonate-semialdehyde | 2.5477 | 1.3492 | 0.012237 | 1.9123 |

TABLE 8-continued

Fold changes in different metabolites between fermented and non-fermented broccoli puree based on untargeted LC-MS analysis.

| Metabolite | FC | log2(FC) | raw. pval | (−LOG10(p)) |
|---|---|---|---|---|
| benzaldehyde | 2.5268 | 1.3373 | 0.01558 | 1.8074 |
| Unidentified metabolite No. 1 | 2.3799 | 1.2509 | 7.84E−05 | 4.1056 |
| Isorhamnetin | 2.2605 | 1.1766 | 0.001828 | 2.738 |
| AMP | 2.1939 | 1.1335 | 0.002464 | 2.6083 |
| 2-Hydroxybenzoic acid | 2.1338 | 1.0935 | 0.006072 | 2.2167 |
| butan-1-al | 2.0853 | 1.0602 | 3.16E−07 | 6.5005 |
| 7-Hydroxymatairesinol | 2.0626 | 1.0445 | 0.008034 | 2.095 |
| Dimethylmatairesinol | 0.43475 | −1.2018 | 0.000284 | 3.5464 |
| trans-zeatin | 0.39207 | −1.3508 | 0.008484 | 2.0714 |
| Unidentified metabolite No. 2 | 0.38059 | −1.3937 | 0.000721 | 3.1421 |
| coniferyl alcohol | 0.37824 | −1.4026 | 0.011806 | 1.9279 |
| papaverine | 0.36651 | −1.4481 | 0.012288 | 1.9105 |
| 2,5-diamino-6-5-phospho-D-ribosylaminopyrimidin-43H-one | 0.3594 | −1.4763 | 0.020453 | 1.6893 |
| S-4-hydroxymandelonitrile | 0.32867 | −1.6053 | 0.00375 | 2.426 |
| 22alpha-hydroxy-campest-4-en-3-one | 0.32674 | −1.6138 | 0.004969 | 2.3037 |
| 3-cyano-L-alanine | 0.32471 | −1.6228 | 0.013212 | 1.879 |
| Ellagic acid glucoside | 0.32466 | −1.623 | 0.022951 | 1.6392 |
| 2-naphthol 6'-O-malonylglucoside | 0.30641 | −1.7064 | 0.000709 | 3.1492 |
| pelargonidin | 0.30629 | −1.707 | 0.010379 | 1.9838 |
| 2S-naringenin | 0.30353 | −1.7201 | 0.019827 | 1.7027 |
| 8-methylthiooctyl-thiohydroximate | 0.28257 | −1.8233 | 0.002811 | 2.5512 |
| Stigmastanol ferulate | 0.28168 | −1.8279 | 0.017703 | 1.752 |
| Pinosylvin | 0.26912 | −1.8937 | 0.01535 | 1.8139 |
| germacra-110,4,1113-trien-12-ol | 0.23506 | −2.0889 | 0.022511 | 1.6476 |
| indole-3-acetyl-glutamine | 0.20278 | −2.302 | 0.006425 | 2.1921 |
| 2-7'-methylthioheptylmalate | 0.19682 | −2.3451 | 0.001077 | 2.968 |
| p-coumaroyltriacetic acid lactone | 0.18436 | −2.4394 | 0.0122 | 1.9136 |
| 6''-O-Acetyldaidzin | 0.15801 | −2.6619 | 0.008935 | 2.0489 |
| indole-3-acetyl-glutamate | 0.15472 | −2.6922 | 0.003623 | 2.441 |
| Isorhamnetin 3-O-glucoside 7-O-rhamnoside | 0.15357 | −2.703 | 0.002647 | 2.5773 |
| olivetol | 0.13094 | −2.933 | 0.005902 | 2.229 |
| N-hydroxy-L-phenylalanine | 0.1141 | −3.1316 | 0.000812 | 3.0905 |
| R-pantothenate | 0.10725 | −3.221 | 1.36E−05 | 4.8679 |
| glucoiberverin | 0.087316 | −3.5176 | 0.00014 | 3.8538 |
| 6-O-methylnorlaudanosoline | 0.055734 | −4.1653 | 6.96E−05 | 4.1575 |
| carlactone | 0.052932 | −4.2397 | 2.93E−05 | 4.5332 |
| E,E-geranyllinalool | 0.018254 | −5.7757 | 0.004044 | 2.3932 |
| UDP-alpha-D-xylose | 13.367 | 3.7407 | 0.0235 | 1.6289 |
| Z-1-glutathione-S-yl-2-phenyl-acetohydroximate | 19.906 | 4.3151 | 0.026163 | 1.5823 |
| Apigenin 7-O-6''-malonyl-apiosyl-glucoside | 0.38092 | −1.3925 | 0.02641 | 1.5782 |
| 4alpha-formyl-stigmasta-7,24241-dien-3beta-ol | 58.691 | 5.8751 | 0.026582 | 1.5754 |
| soyasapogenol B | 0.35836 | −1.4805 | 0.027448 | 1.5615 |
| dihydroconiferyl alcohol glucoside | 5.6248 | 2.4918 | 0.027644 | 1.5584 |
| 3-deoxy-alpha-D-manno-octulosonate | 6.6012 | 2.7227 | 0.027652 | 1.5583 |
| Anhydro-secoisolariciresinol | 2.3975 | 1.2616 | 0.027928 | 1.554 |
| 3-isopropyl-7-methylthio-2-oxoheptanoate | 0.30287 | −1.7232 | 0.028072 | 1.5517 |
| Kaempferide | 0.15749 | −2.6666 | 0.0281 | 1.5513 |
| 2-aminoprop-2-enoate | 2.0003 | 1.0002 | 0.029166 | 1.5351 |
| isoliquiritigenin | 2.8505 | 1.5112 | 0.029212 | 1.5344 |
| m-Coumaric acid | 2.187 | 1.129 | 0.029331 | 1.5327 |
| indole-5,6-quinone | 2.6937 | 1.4296 | 0.02956 | 1.5293 |
| 2-4'-methylthiobutylmalate | 0.43617 | −1.197 | 0.030711 | 1.5127 |
| 7-methylthioheptyl glucosinolate | 0.42422 | −1.2371 | 0.030739 | 1.5123 |
| camalexin | 0.27584 | −1.8581 | 0.030778 | 1.5118 |
| 3-Methoxynobiletin | 8.9717 | 3.1654 | 0.031528 | 1.5013 |
| 8-methylsulfinyloctyl glucosinolate | 0.1694 | −2.5615 | 0.031733 | 1.4985 |
| ent-cassa-12,15-diene | 0.33284 | −1.587 | 0.032806 | 1.484 |
| Catechol | 4.0005 | 2.0002 | 0.033382 | 1.4765 |
| L-aspartate-semialdehyde | 2.9298 | 1.5508 | 0.033499 | 1.475 |
| 10-methylthio-2-oxodecanoate | 4.5655 | 2.1908 | 0.033543 | 1.4744 |
| indole-3-carbinonium ion | 2.7807 | 1.4754 | 0.033654 | 1.473 |
| laurate | 0.33955 | −1.5583 | 0.034205 | 1.4659 |
| malonate | 9.0975 | 3.1855 | 0.035699 | 1.4473 |
| 1-aci-nitro-8-methylsulfanyloctane | 8.8356 | 3.1433 | 0.035865 | 1.4453 |
| 2-hydroxy-5-methylthio-3-oxopent-1-enyl 1-phosphate | 13.56 | 3.7612 | 0.036727 | 1.435 |
| glyoxylate | 16.835 | 4.0734 | 0.037951 | 1.4208 |
| Feruloyl tartaric acid | 5.5489 | 2.4722 | 0.038578 | 1.4137 |
| 3beta-hydroxyparthenolide | 8.1691 | 3.0302 | 0.038749 | 1.4117 |
| 22R,23R-22,23-dihydroxycampesterol | 2.0564 | 1.0401 | 0.039305 | 1.4056 |

TABLE 8-continued

Fold changes in different metabolites between fermented and non-fermented broccoli puree based on untargeted LC-MS analysis.

| Metabolite | FC | log2(FC) | raw. pval | (−LOG10(p)) |
|---|---|---|---|---|
| Gallic acid 4-O-glucoside | 2.515 | 1.3306 | 0.039605 | 1.4023 |
| E-phenylacetaldoxime | 2.1608 | 1.1116 | 0.040641 | 1.391 |
| 18-hydroxystearate | 0.14519 | −2.784 | 0.042027 | 1.3765 |
| 5'-phosphoribosyl-4-N-succinocarboxamide-5-aminoimidazole | 0.4281 | −1.224 | 0.042243 | 1.3742 |
| 3-Feruloylquinic acid | 3.3496 | 1.744 | 0.042655 | 1.37 |
| 2-carboxy-L-threo-pentonate | 2.0447 | 1.0319 | 0.043 | 1.3665 |
| trans-zeatin riboside | 0.40453 | −1.3057 | 0.044527 | 1.3514 |
| 4-fumaryl-acetoacetate | 5.0298 | 2.3305 | 0.044744 | 1.3493 |
| 2-cis-abscisate | 76.81 | 6.2632 | 0.044918 | 1.3476 |
| 4-Hydroxycoumarin | 0.48212 | −1.0525 | 0.045785 | 1.3393 |
| Biochanin A | 2.1017 | 1.0716 | 0.046533 | 1.3322 |
| S-2,3,4,5-tetrahydrodipicolinate | 4.1401 | 2.0497 | 0.046976 | 1.3281 |
| 26,27-dehydrozymosterol | 14.846 | 3.892 | 0.047042 | 1.3275 |
| N-methylethanolamine phosphate | 10.038 | 3.3273 | 0.047416 | 1.3241 |
| Kaempferol 3-O-2"-rhamnosyl-galactoside 7-O-rhamnoside | 2.7008 | 1.4334 | 0.048201 | 1.3169 |
| pheophorbide a | 6.3398 | 2.6644 | 0.049365 | 1.3066 |
| Chrysoeriol 7-O-6"-malonyl-glucoside | 4.8949 | 2.2913 | 0.049727 | 1.3034 |
| allantoate | 10.972 | 3.4557 | 0.050008 | 1.301 |
| Ligstroside-aglycone | 12.072 | 3.5936 | 0.052404 | 1.2806 |
| cycloeucalenone | 3.4926 | 1.8043 | 0.052645 | 1.2786 |
| Unidentified metabolite No. 3 | 3.5807 | 1.8403 | 0.053727 | 1.2698 |
| laricitrin | 0.42811 | −1.224 | 0.05399 | 1.2677 |
| Sulfadimethoxine | 11.488 | 3.5221 | 0.05455 | 1.2632 |
| 3,4-Diferuloylquinic acid | 5.2839 | 2.4016 | 0.054583 | 1.2629 |
| glucotropeolin | 0.47952 | −1.0603 | 0.054637 | 1.2625 |
| 5,6-dihydroxyindole-2-carboxylate | 5.2663 | 2.3968 | 0.055218 | 1.2579 |
| S-laudanine | 2.8697 | 1.5209 | 0.055638 | 1.2546 |
| L-nicotianamine | 0.39854 | −1.3272 | 0.057257 | 1.2422 |
| 5-methylthiopentyl-thiohydroximate | 0.30202 | −1.7273 | 0.057551 | 1.2399 |
| aldehydo-D-galacturonate | 2.6643 | 1.4138 | 0.05785 | 1.2377 |
| R-mevalonate 5-phosphate | 0.34888 | −1.5192 | 0.058188 | 1.2352 |
| 6-Hydroxyluteolin 7-O-rhamnoside | 2.142 | 1.099 | 0.05845 | 1.2332 |
| L-aspartate | 3.5705 | 1.8361 | 0.061441 | 1.2115 |
| --Epicatechin 3-O-gallate | 2.4481 | 1.2916 | 0.063269 | 1.1988 |
| glycine | 0.23586 | −2.084 | 0.065585 | 1.1832 |
| Episesaminol | 2.4077 | 1.2677 | 0.065876 | 1.1813 |
| 6alpha-hydroxy-castasterone | 3.7782 | 1.9177 | 0.068376 | 1.1651 |
| alpha-D-galacturonate 1-phosphate | 11.846 | 3.5664 | 0.070966 | 1.149 |
| R-2,3-dihydroxy-3-methylpentanoate | 2.995 | 1.5825 | 0.071057 | 1.1484 |
| cyanidin-3-O-beta-D-glucoside | 2.0686 | 1.0487 | 0.07128 | 1.147 |
| D-erythrose 4-phosphate | 3.7463 | 1.9054 | 0.07247 | 1.1398 |
| CDP-choline | 617.84 | 9.2711 | 0.073728 | 1.1324 |
| adenine | 2.0623 | 1.0442 | 0.074004 | 1.1307 |
| raphanusamate | 5.5593 | 2.4749 | 0.074387 | 1.1285 |
| 3-Methoxysinensetin | 2.4046 | 1.2658 | 0.075102 | 1.1243 |
| betaine aldehyde | 3.5234 | 1.817 | 0.075291 | 1.1233 |
| E-7-methylthioheptanaldoxime | 2.2972 | 1.1999 | 0.076906 | 1.114 |
| 6-methylthiohexyl-thiohydroximate | 5.5473 | 2.4718 | 0.077579 | 1.1103 |
| 6"-O-Malonylglycitin | 0.16741 | −2.5786 | 0.080677 | 1.0933 |
| monodehydroascorbate radical | 2.0677 | 1.048 | 0.081844 | 1.087 |
| anthranilate | 3.0289 | 1.5988 | 0.082088 | 1.0857 |
| Hydroxycaffeic acid | 0.43234 | −1.2098 | 0.082209 | 1.0851 |
| Myricetin 3-O-arabinoside | 2.3978 | 1.2617 | 0.086518 | 1.0629 |
| cis-aconitate | 0.18331 | −2.4477 | 0.088998 | 1.0506 |
| 5-phospho-alpha-D-ribose 1-diphosphate | 0.47829 | −1.064 | 0.089065 | 1.0503 |
| Malvidin 3-O-glucoside | 0.48171 | −1.0538 | 0.089472 | 1.0483 |
| N6-delta2-isopentenyl-adenosine 5'-monophosphate | 44.241 | 5.4673 | 0.092566 | 1.0335 |
| Quercetin 3-O-6"-acetyl-galactoside 7-O-rhamnoside | 2.9914 | 1.5808 | 0.093824 | 1.0277 |
| cholesterol | 2.816 | 1.4936 | 0.095163 | 1.0215 |
| 9-methylthiononyl-thiohydroximate | 15.416 | 3.9464 | 0.098598 | 1.0061 |

In order to determine the effects of fermentation on the polyphenolic metabolites of broccoli samples, targeted liquid chromatography-mass spectrometry (LC-MS) based metabolomic analysis of the raw and fermented broccoli puree samples was conducted. Statistical analysis was performed without preprocessing. Fermentation resulted in a significant change in the metabolite profile of the broccoli samples.

In the targeted LC-MS analysis, polyphenol standards were used for the identification and quantification of the metabolites. Increases in chlorogenic acid, ferullic acid, syringic acid, phenyllactic acid, rutin, sinapic acid, methyl syringate, hesperetin, quercetin and kaempferol were confirmed in fermented broccoli (FIG. 12). Decreases in protocatechuic acid, gallic acid, 4,hydroxybenzoic acid, vanillic acid, 2,3dihydroxybenzoic acid, p-cuomaric acid, cinnamic acid, catechin, rosmarinic acid, caffeic acid were confirmed in fermented broccoli (FIG. 12). Of note is that a 6.6 fold change in chlorogenic acid (2.4 to 15.8 μg/mg), a 23.8 fold increase is in sinapic acid (3.6 to 86.6 μg/mg), a 10.5 increase in kaempferol (12.7 to 134.6 μg/mg) and a 0.48 fold decrease in p-Coumaric acid occurred in fermented samples (FIG. 12).

Example 14—Assessment of the Broccoli Fermentation Culture to Inhibit the Growth of Intentionally Introduced Microorganisms A challenge study was conducted to assess the ability of the broccoli fermentation culture to inhibit the growth of intentionally introduced microorganisms which are often observed and of concern in food preparation.

Lab Culture/Starter Culture 10 ml of $10^{10}$ cfu/mL of an inoculum comprising B1, B2, B3, B4, B5, BF1 and BF2 to achieve $10^8$ CFU/gm of sample in the ferment.

Pathogen Cultures

*E. coli* isolates FSAW 1310, FSAW 1311, FSAW 1312, FSAW 1313 and FSAW 1314 were grown separately to $1-4\times10^8$ cfu/mL in NB (nutrient broth) overnight at 37° C., static. The cultures were combined (1 mL of each) and the combined culture diluted to $10^4$ with MRD (maximum recovery diluent) for first two dilutions and water for last two dilutions.

*Salmonella* strains *S. Infantis* 1023, *S. Singapore* 1234, *S. Typhimurium* 1657 (PT135), *S. Typhimurium* 1013 (PT9) and *S. Virchow* 1563 were grown separately to $1-4\times10^8$ cfu/mL in NB overnight at 37° C., static. The cultures were combined (1 mL of each) and combined culture diluted to $10^4$ with MRD for first two dilutions and water for last two dilutions.

*Listeria* isolates Lm2987 (7497), Lm2965 (7475), Lm2939 (7449), Lm2994 (7537) and Lm2619 (7514) were grown separately in 10 mL BHI (brain heart infusion broth) overnight at 37° C. under agitation. All cultures were then combined (1 mL of each) and this cocktail was diluted using MRD for first two (1/10) dilutions and sterile deionised water for last two dilutions.

*B. cerus* spore crops were prepared from isolates B3078, B2603, 2601, 7571 and 7626.

Method

Broccoli puree was prepared prior to preparing the inoculums, Broccoli: Sterile Tap Water 3:2 (900 g broccoli: 600 g water). Broccoli heads were rinsed in tap water, the stalks were cut off the broccoli with a sterile knife on a cutting board sanitised with 80% ethanol. Broccoli florets (900 g) were cut into small pieces. 450 g of broccoli pieces were placed into Thermomix bowl with all 600 g of the water. The translucent Thermomix cup/lid was sanitised with 80% ethanol and placed over the lid hole. The broccoli was chopped at speed 4 for 1 min. The second 450 g of broccoli pieces were added to the Thermomix bowl and chopped at speed 4 for 1 min. The contents were chopped for a further 5 min at speed 10 (max). After making sure the puree was indeed smooth enough, the Thermomix bowl was placed in the cool room to cool down the contents for 30 min Following this, the bowl was put in the incubator and equilibrated to 30° C. Meanwhile the starter culture and pathogen culture (*E. coli, B. cereus, Salmonella, Listeria monocytogenes*) were prepared. 10 mL of LAB culture and 7.5 mL of the 10-4-diluted challenge microorganism cocktail ($10^4$ cfu/mL culture in water) were added into the broccoli puree ($10^5$ of *B. cereus*). Foil was held down over the large hole in the Thermomix lid prior to mixing culture. The cultures were mixed into the puree for 1 min on maximum speed. The heat setting for the Thermomix was switched off and the Thermomix was placed inside the 30° C. incubator and the fermentation started at 10:45 am. pH and temperature measurements were taken every hour up until 7 h (end of work time) after mixing the puree for 1 min speed 4.5. The pH meter was calibrated and sanitised using 80% ethanol. The temperature probe was also sanitised prior to measurements with 80% ethanol.

The growth of the challenge microorganisms was assessed by counts on growth on the selective media MRS, DRBX and NA+S of raw broccoli, before fermentation (T0) and after fermentation commenced at 4 hours (T4) and 22 hours (T22).

Results

The yeast and mould were significantly reduced by 4 hours, and were not detected at the end of fermentation (T22). *E. coli* and *Salmonella* were never detected at the end of fermentation (T22). *Listeria* was detected in low numbers at the end of fermentation, with a starting inoculum just over $10^3$ cfu/mL. *B. cereus* spores were generally not affected by the fermentation, but did not germinate. The result of the challenge study indicates that the lactic acid bacteria strains that we isolated from broccoli are able to completely inactivate *Salmonella* and *E. coli* and inhibit the growth of the most acid resistant strains of *Listeria*. They are also able to inhibit the sporulation of *B. cerus* spores.

TABLE 9

Example of microbial challenge study with *E. coli*. *E. coli* (mix of 5 *E. coli* strains EC1605, EC1606, EC1607, EC1608 inoculated (2.2 × 102 CFU/gm) into the macerated broccoli (3:2 broccoli-water ratio) ferment to evaluate if the fermentation starter (a consortia of B1, B2, B3, B4, B5, BF1, BF2) inhibits the growth of *E.coli*. Experiments were repeated three times. Fermentation was conducted at 30° C. for 22 hrs to pH below 4.0.

| Time (hrs) | Lactic acid bacteria (CFU/gm) | Yeast and mould (CFU/gm) | *E. coli* (CFU/gm) |
|---|---|---|---|
| 0 | $1.6 \times 10^8$ | $2.4 \times 10^3$ | $1.6 \times 10^2$ |
| 4 | $1.5 \times 10^8$ | $3 \times 10$ | $1.2 \times 10^2$ |
| 22 | $3.6 \times 10^9$ | <10 | <1 |

TABLE 10

Example of microbial challenge study with *Salmonella*. *Salmonella* (A mix of 5 strains *S. Infantis* 1023, S. Singapore 1234, *S. Typhimurium* 1657 (PT135), *S. Typhimurium* 1013 (PT9), S. Virchow 1623) inoculated (1.1 × 103) into macerated broccoli (3:2 broccoli-water ratio) ferment to evaluate if the fermentation starter (a consortia of B1, B2, B3, B4, B5, BF1, BF2) inhibits the growth of *Salmonella*. Experiments were repeated three times. Fermentation was conducted at 30° C. for 22 hrs to pH below 4.0.

| Time (hrs) | Lactic acid bacteria (CFU/gm) | Yeast and mould (CFU/gm) | *Salmonella* (CFU/gm) |
|---|---|---|---|
| 0 | $3.5 \times 10^8$ | $1.4 \times 10^3$ | $6.4 \times 10^2$ |
| 4 | $4.2 \times 10^8$ | $2 \times 10$ | $3.3 \times 10^2$ |
| 22 | $1.4 \times 10^9$ | <10 | <10 |

TABLE 11

Example of microbial challenge study with *Listeria monocytogenes*.
*Listeria monocytogenes* (A mix of 5 strains Lm2987 (7497),
Lm2965 (7475), Lm2939 (7449), Lm2994 (7537), Lm2919 (7514))
inoculated (1.9 × 103) into macerated broccoli (3:2 broccoli-
water ratio) ferment to evaluate if the fermentation starter (a consortia
of B1, B2, B3, B4, B5, BF1, BF2) inhibits the growth of acid resistant
*Listeria*. Experiments were repeated three times and the final
*Listeria* count at the end of fermentation ranged from <10
(undetected) to $1.1 \times 10^2$ CFU/gm. Fermentation was conducted
at 30° C. for 22 hrs to pH below 4.0.

| Time (hrs) | Lactic acid bacteria (CFU/gm) | Yeast and mould (CFU/gm) | *Listeria* (CFU/gm) |
|---|---|---|---|
| 0 | $5.6 \times 10^8$ | $5.2 \times 10^4$ | $2.1 \times 10^3$ |
| 4 | $4.1 \times 10^8$ | $3.6 \times 10^3$ | $2.8 \times 10^3$ |
| 22 | $5.1 \times 10^9$ | <10 | $2 \times 10$ |

TABLE 12

Example of microbial challenge study with *Bacillus cereus*.
*Bacillus cereus* (A mix of 5 strains B3078, B2603, B2601, B7571,
B7626) inoculated (1.9 × 103) into macerated broccoli (3:2
broccoli-water ratio) ferment to evaluate if the fermentation starter
(a consortia of B1, B2, B3, B4, B5, BF1, BF2) inhibits the growth of
acid resistant *Listeria*. Experiments were repeated three times.
Fermentation was conducted at 30° C. for 22 hrs to pH below 4.0.

| Time (hrs) | Lactic acid bacteria (CFU/gm) | Yeast and mould (CFU/gm) | *Listeria* (CFU/gm) |
|---|---|---|---|
| 0 | $2.4 \times 10^8$ | $1.2 \times 10^3$ | $3.1 \times 10^3$ |
| 4 | $3.3 \times 10^8$ | $9.5 \times 10$ | $2.3 \times 10^3$ |
| 22 | $1.9 \times 10^9$ | <10 | $1.7 \times 10^3$ |

Example 15—Pulse Filed Gel Electrophoreses of *Leuconostoc mesenteroides* Isolates

*Leuconostoc mesenteroides* from vegetables was assessed with SmaI and NotI restriction enzyme digestion with pulse filed gel electrophoreses as described in Chat and Dalmasso (2015) with modification.

Methods:

Day 1

Assessed isolates were inoculated into 10 mL MRS broth and incubated overnight at 30° C. in incubator (16 h).

Day 2

Isolates were centrifuge at 3500 g for 10 min and the supernatant discarded. The pellet was mixed and washed with 5 mL deionised water and centrifuged at 3500 g for 10 min and the supernatant discarded. The pellet was mixed with 5 mL TES (1 mM EDTA, 10 mM Tris-HCl, 0.5 M saccharose) and vortexed. Next the samples were centrifuged at 3500 g for 15 min and the supernatant discarded. 700 µL of Lysis solution (TE buffer (1 mM EDTA, 10 mM Tris-HCl, pH 8.0, sterilise as normal) with lysozyme at 10 mg/mL) was added to the pellet and mixed and incubated at 56° C. for 2 h to lyse bacteria. Next, 700 µL of agarose (1% SeaChem Gold agarose with 50 µL EDTA/100 mL) was added to the cell mixture, mix and dispensed into plug moulds and 2 mL of deproteinisation (660 µL of proteinase K buffer, 11 µL proteinase K) solution added all plugs for one sample placed in the tube and incubated at 55° C. overnight.

Day 3

Next the plugs were heated in 100 mL of sterile deionised water at 55° C., the deproteinisation solution was removed and the plugs transferred to 15 mL centrifuge tubes, washed with 4 mL of sterile deionised water and heated to 55° C. for 10 min at room temperature followed by washing four times with 4 mL TE buffer for 10 min at room temperature.

Restriction Digests 2 mm slice off plug was placed in an eppendorf tube with 100 µL 1× restriction buffer, incubated for 20 min at room temperature, restriction buffer was removed and replaced with 40-100 µL of SmaI (20 U) or NotI in restriction buffer and incubated for 4 h at the optimum temperature (25° C.).

Day 4

Separation of Restriction Fragments 1 mL 0.5×TBE buffer to each tube and allowed to sit for at least 15 min to stop reaction and the bacteriophage 2 DNA ladder (New England Biolab) was incubated in TBE buffer. The buffer was removed and the slices loaded onto comb, with the ladder in every five lanes. 1.0% ultra-pure DNA grade agarose (pulsed field certified agarose) was prepared in 0.5×TBE running buffer.

Electrophoresis Conditions

Buffer maintained at 14° C. (model 1000 Mini-chiller, BioRad).BioRad "Chef Mapper™", select Two State Program (not Auto Algorithm). Pulse time ramped linearly (press enter when "a" appears) from 2 to 25 s. Gradient 6 V/cm (voltage), Included angle 120°, Running time of 24 h.

Day 5

Gels stained ~30 min in GelRed, destained, visualised

Results

The restriction fingerprint for BF1 was district but similar to *Leuconostoc mesenteroides* isolated from carrot (FIG. 13). The restriction fingerprint for BF2 was district from all *Leuconostoc mesenteroides* strains assessed (FIG. 13).

Example 16—Variant Analysis of *Leuconostoc mesenteroides* and *Lactobacillus plantarum* Isolates For the SNP analysis of the *Lactobacillus plantarum* isolates (B1 to B5), B1 Prokka gbk was used as reference for Snippy SNP analysis—standard method. Single comparisons were performed using read data for each strain. B1 reads were ran as a control.

Example command was:

snippy --cpus 24 --outdir B5 --ref B1_Slmod.gbk --pe1 B5_S17_L001_R1_001.fastq.gz --pe2 B5_S17_L001_R2_001.fastq.gz Calculated individual comparisons and core using B1 gbk as reference snippy-core --prefix core B1 B2 B3 B4 B5

Comparisons were also performed between B1 and the reference strain read data downloaded from the SRA for *Lactobacillus plantarum* ATCC 8014 (SRR1552613). Downloading was performed using standard method with prefetch and conversion to fastq using—sratoolkit.2.9.2-win64. Similar approaches were used for comparison of the *Leuconostoc mesenteroides* isolates BF1 and BF2 with *Leuconostoc mesenteroides* ATCC 8293 as reference.

Results

Variants (41) were observed between 131 and ATCC 8014 (Table 13). Variants (1 to 4) were observed between B1 and the other B isolates B2, B3, B4 and B5 (Table 14 to 17). BF1 and BF2 are very different from one another. Variants (19) were observed between BF1 and ATCC 8293 (Table 18). Variants (7000) were observed between BF2 and ATCC 8293. 459 complex variants were identified between BF2 and ATCC8293 which are summarized in Table 19.

TABLE 13

Polymorphisms identified by variant analysis B1 compared to ATCC8014.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 292863 | complex | GTCG | ATCT | ATCT: 96<br>GTCG: 0 | CDS | + | 292/477 | 98/158 | missense_variant c.292_295delGTCGins ATCT p.ValAla98Ile Ser | JBMIHLAL_00290 | ohrR_1 |
| 21413 | snp | C | T | T: 20<br>4C: 1 | | | | | | | |
| 49138 | snp | T | G | G: 226<br>T: 2 | CDS | + | 771/1011 | 257/336 | missense_variant c.771T>G p.Asn257 Lys | JBMIHLAL_00337 | lacR_1 |
| 68529 | del | TATTAATGGCTCGCGTCATTAA | TA | TA: 97<br>TATTAATGGCTCGCGTCATTAA: 0 | | | | | | | |
| 70435 | snp | G | A | A: 199<br>G: 1 | CDS | - | 95/1959 | 32/652 | missense_variant c.95C>T p.Thr32Ile | JBMIHLAL_00352 | lacS_2 |
| 70584 | snp | T | C | C: 154<br>T: 1 | | | | | | | |
| 71677 | snp | T | C | C: 201<br>T: 0 | CDS | - | 209/1029 | 70/342 | missense_variant c.209A>G p.Tyr70 Cys | JBMIHLAL_00353 | |
| 72030 | del | CGCTCAACCAGATTAGTACCCAG | CG | CG: 91<br>CGCTCAACCAGATTAGTACCCAG: 0 | CDS | - | 978/996 | 320/331 | inframe_deletion c.958_978delCTGGGTACTAATCTGGTTGAG p.Leu320_Glu326 del | JBMIHLAL_00354 | lacR_3 |
| 136221 | snp | C | A | A: 178<br>C: 1 | CDS | - | 559/1272 | 187/423 | missense_variant c.559G>T p.Ala187 Ser | JBMIHLAL_00407 | gatC_1 |
| 15092 | snp | C | A | A: 102<br>C: 1 | | | | | | | |
| 153210 | snp | G | T | T: 117<br>G: 1 | CDS | - | 385/1365 | 129/454 | missense_variant c.385C>A p.Gln129 Lys | JBMIHLAL_00681 | gabR |
| 38124 | snp | C | T | T: 264<br>C: 1 | | | | | | | |
| 128067 | snp | G | A | A: 261<br>G: 1 | CDS | - | 208/1344 | 70/447 | missense_variant c.208C>T p.Arg70 Cys | JBMIHLAL_01118 | yjjP_1 |
| 188850 | snp | A | C | C: 241<br>A: 0 | CDS | - | 491/1617 | 164/538 | missense_variant c.491T>G p.Ile164 Ser | JBMIHLAL_01179 | oppA_2 |
| 2322 | snp | A | G | G: 107<br>A: 1 | CDS | - | 397/474 | 133/157 | missense_variant c.397T>C p.Phe133 Leu | JBMIHLAL_01186 | adcR |
| 111662 | ins | CAA | CAAA | CAAA: 133<br>CAA: 11 | CDS | + | 10/876 | 4/291 | frameshift_variant c.9dupA p.Ser4fs | JBMIHLAL_01302 | mntB |
| 11376 | snp | G | A | A: 115<br>G: 0 | | | 1831/1947 | 611/648 | synonymous_variant c.1831C>T p.Leu611Leu | JBMIHLAL_01356 | |
| 115510 | snp | G | A | A: 199<br>G: 1 | CDS | - | 95/411 | 32/136 | missense_variant c.95C>T p.Thr32Ile | JBMIHLAL_01453 | |
| 143457 | snp | G | C | C: 264<br>G: 0 | CDS | + | 1122/1416 | 374/471 | synonymous_variant c.1122G>C p.Val374Val | JBMIHLAL_01479 | pepD |

TABLE 13-continued

Polymorphisms identified by variant analysis B1 compared to ATCC8014.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 111973 | snp | G | A | A: 118<br>G: 1 | CDS | - | 731/<br>1317 | 244/<br>438 | missense_variant<br>c.731C>T p.Ala244<br>Val | JBMIHLAL_<br>01603 | murA1 |
| 27553 | snp | C | T | T: 104<br>C: 1 | CDS | - | 472/<br>1092 | 158/<br>363 | missense_variant<br>c.472G>A p.Gly158<br>Ser | JBMIHLAL_<br>01677 | wbnH |
| 80888 | snp | T | C | C: 84<br>T: 0 | CDS | + | 256/<br>258 | 86/<br>85 | stop_lost&splice_<br>re-gion_variant<br>c.256T>C p.Ter<br>86Glnext*? | JBMIHLAL_<br>01727 | ytlR_<br>1 |
| 133147 | snp | A | C | C: 76<br>A: 0 | CDS | - | 443/<br>663 | 148/<br>220 | missense_variant<br>c.443T>G p.Phe148<br>Cys | JBMIHLAL_<br>01777 | yjbM |
| 74711 | snp | C | T | T: 212<br>C: 1 | CDS | + | 874/<br>1389 | 292/<br>462 | missense_variant<br>c.874C>T p.Leu292<br>Phe | JBM1HLAL_<br>01855 | murF_<br>2 |
| 19793 | snp | T | C | C: 114<br>T: 1 | CDS | - | 925/<br>1107 | 309/<br>368 | missense_variant<br>c.925A>G<br>p.Asn309Asp | JBMIHLAL_<br>01907 | sigA |
| 60643 | snp | C | T | T: 89<br>C: 1 | CDS | - | 242/<br>1869 | 81/<br>622 | missense_variant<br>c.242G>A p.Ser81<br>Asn | JBMIHLAL_<br>01945 | dnaK |
| 10806 | ins | GTTT<br>TTTT<br>TG | GTTT<br>TTTT<br>TTG | GTTTTTTT<br>TTG: 49<br>GTTTTTTT<br>TG: 1 | | | | | | | |
| 50276 | com-<br>plex | CG | CACC<br>ACCA<br>GGCC<br>GATT<br>GTGG<br>CGA | CACCACCA<br>GGCCGATT<br>GTGGCGA:<br>39<br>CG: 0 | CDS | - | 341/<br>555 | 114/<br>184 | missense_variant&<br>inframe_insertion<br>c.341delCinsTCGCCA<br>CAATCGGCCTGGTGGT<br>p.Ala114delinsVal<br>AlaThrIleGlyLeu<br>ValVal | JBMIHLAL_<br>02031 | ribU |
| 50325 | snp | A | C | C: 99<br>A: 1 | CDS | - | 293/<br>555 | 98/<br>184 | stop_gained c.293<br>T>G p.Leu98* | JBMIHLAL_<br>02031 | ribU |
| 64233 | snp | A | G | G: 77<br>A: 1 | CDS | - | 2516/<br>2604 | 839/<br>867 | missense_variant<br>c.2516T>C<br>p.Val839Ala | JBMIHLAL_<br>02043 | clpB |
| 79046 | snp | G | C | C: 140<br>G: 1 | CDS | + | 394/<br>765 | 132/<br>254 | missense_variant<br>c.394G>C p.Ala132<br>Pro | JBMIHLAL_<br>02139 | ygaZ_<br>2 |
| 14904 | snp | G | A | A: 82<br>G: 0 | CDS | - | 113/<br>876 | 38/<br>291 | missense_variant<br>c.113C>T p.Pro38<br>Leu | JBMIHLAL_<br>02340 | |
| 45542 | snp | T | G | G: 158<br>T: 0 | CDS | - | 1312/<br>1718 | 438/<br>575 | missense_variant<br>c.1312A>C<br>p.Lys438Gln | JBMIHLAL_<br>02365 | pgcA |
| 21706 | ins | TAT | TAAT | TAAT: 122<br>TAT: 1 | CDS | + | 872/<br>2604 | 291/<br>867 | frameshift_variant<br>c.871dupA p.Ile<br>291fs | JBMIHLAL_<br>02489 | mprF |
| 29454 | del | TGA | TA | TA: 73<br>TGA: 0 | CDS | + | 94/<br>132 | 32/<br>43 | frameshift_variant<br>c.94delG p.Asp32fs | JBMIHLAL_<br>02559 | |
| 27619 | snp | A | G | G: 134<br>A: 1 | CDS | - | 78/<br>588 | 26/<br>195 | synonymous_variant<br>c.78T>C p.Gly26Gly | JBMIHLAL_<br>02812 | |
| 4360 | snp | C | T | T: 96<br>C: 1 | | | | | | | |

TABLE 13-continued

Polymorphisms identified by variant analysis B1 compared to ATCC8014.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 8851 | del | CGG | CG | CG: 117<br>CGG: 0 | CDS | − | 82/513 | 28/170 | frameshift_variant<br>c.82delC p.Pro28fs | JBMIHLAL_02963 | tcaR |
| 19068 | del | CTTG<br>CCGA<br>AATT<br>CGAC<br>AAAC<br>AACC<br>CTCG<br>GATT<br>GT | CT | CT: 51<br>CTTGCCGA<br>AATTCGAC<br>AAACAACC<br>CTCGGATT<br>GT: 0 | CDS | + | 154/564 | 52/187 | frameshift_variant<br>c.154_185delGAAATT<br>CGACAAACAACCCTCG<br>GATTGTTGCC<br>p.Glu52fs | JBMIHLAL_02974 | |
| 17533 | ins | ATTT<br>TTTG | ATTT<br>TTTT<br>G | ATTTTTTT<br>G: 220<br>ATTTTTTG:<br>2 | | | | | | | |

TABLE 14

Polymorphism identified by variant analysis B2 compared to B1.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 8417 | snp | C | T | T:105 C:0 | CDS | + | 105/264 | 35/87 | synonymous_variant<br>c.105C > T p.Asp35Asp | JBMIHLAL_02984 | |

TABLE 15

Polymorphisms identified by variant analysis B3 compared to B1

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 4326 | del | TATAAAAAAGCG ACCCCGTTCATTA ACGTGCCGCTCA CAGATCATTATTAG TGAAAATCACCCG GCA | TA | TA:31 TATAAAAAAGCGACC TATAAAAAAGCGACC CCCGTTCATTAACGGT GCCGCTCACAGATCAT TATTAGTGAAAATCAC CCGGCA:0 | | | | | | | |
| 8417 | snp | C | T | T:135 C:0 | CDS | + | 105/264 | 35/87 | synonymous_variant c.105C > T p.Asp35Asp | JBMIHLAL_02984 | |

TABLE 16

Polymorphism identified by variant analysis B4 compared to B1.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 8417 | snp | C | T | T:93 C:0 | CDS | + | 105/264 | 35/87 | synonymous_variant c.105C > T p.Asp35Asp | JBMIHLAL_02984 | |

TABLE 17

Polymorphisms identified by variant analysis B5 compared to B1.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 199035 | snp | T | C | C:124 T:0 | CDS | + | 368/1206 | 123/401 | missense_variant c.368T > C p.Val123Ala | JBMIHLAL_00946 | |
| 143457 | snp | G | C | C:158 G:0 | CDS | + | 1122/1416 | 374/471 | synonymous_variant c.1122G > C p.Val374Val | JBMIHLAL_01479 | pepD |
| 23797 | snp | A | C | C:146 A:0 | CDS | + | 71/666 | 24/221 | missense_variant c.71A > C p.Gln24Pro | JBMIHLAL_02490 | immR_1 |
| 8417 | snp | C | T | T:131 C:0 | CDS | + | 105/264 | 35/87 | synonymous_variant c.105C > T p.Asp35Asp | JBMIHLAL_02984 | |

TABLE 18

Polymorphisms identified by variant analysis BF1 compared to ATCC8293.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 197592 | del | TGT | TT | TT:178 TGT:0 | | | | | | | |
| 269841 | del | TGG | TG | TG:305 TGG:0 | CDS | + | 33/306 | 11/101 | frameshift_variant c.33delG p.Asn12fs | LEUM_0316 | |
| 338699 | snp | G | T | T:239 G:0 | CDS | + | 764/1719 | 255/572 | missense_variant c.764G > T p.Trp255Leu | LEUM_0385 | |
| 410044 | snp | C | A | A:210 C:0 | CDS | + | 2229/2457 | 743/818 | synonymous_variant c.2229C > A p.Thr743Thr | LEUM_0448 | pheT |
| 558511 | ins | CAT | CAAT | CAAT:140 CAT:0 | CDS | + | 204/261 | 68/86 | frameshift_variant c.203dupA p.His68fs | LEUM_0587 | |
| 559188 | snp | A | G | G:169 A:0 | CDS | + | 601/981 | 201/326 | missense_variant c.601A > G p.Ile201Val | LEUM_0588 | |
| 615572 | del | TCC | TC | TC:245 TCC:5 | | | | | | | |
| 755527 | snp | A | T | T:196 A:0 | CDS | + | 351/993 | 117/330 | missense_variant c.351A > T p.Leu117Phe | LEUM_0777 | |
| 796683 | del | GCC | GC | GC:207 GCC:0 | CDS | + | 2986/3009 | 996/1002 | frameshift_variant c.2986delC p.Glu997fs | LEUM_0814 | |
| 953160 | snp | G | T | T:178 G:0 | CDS | + | 805/843 | 269/280 | missense_variant c.805G > T p.Ala269Ser | LEUM_0952 | |
| 1009293 | snp | C | A | A:1652 C:171 | CDS | + | | | no annotation | LEUM_1009 | |
| 1094250 | snp | T | A | A:188 T:0 | CDS | + | | | no annotation | LEUM_1090 | |
| 1236979 | snp | G | T | T:194 G:1 | | | | | | | |
| 1237016 | del | CAA | CA | CA:183 CAA:6 | | | | | | | |

TABLE 18-continued

Polymorphisms identified by variant analysis BF1 compared to ATCC8293.

| POS | TYPE | REF | ALT | EVIDENCE | FTYPE | STRAND | NT_POS | AA_POS | EFFECT | LOCUS_TAG | GENE |
|---|---|---|---|---|---|---|---|---|---|---|---|
| 1291050 | del | CGT | CT | CT:177 CGT:0 | | | | | | | |
| 1600218 | del | AGG | AG | AG:168 AGG:2 | | | | | | | |
| 1624087 | ins | GA | GTA | GTA:205 GA:0 | | | | | | | |
| 1693283 | snp | T | A | A:247 T:0 | CDS | – | | | no annotation | LEUM_1724 | |
| 1993032 | snp | G | A | A:209 G:0 | CDS | – | | | no annotation | LEUM_2026 | |

TABLE 19

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1737 | TTCA | ATCC | ATCC: 151 TTCA: 0 | CDS | + | 63/1137 | 21/378 | synonymous_variant c.63_66delTTCAinsATCC p.IleSer21IleSer | LEUM_0002 | |
| 11810 | CATG | TATA | TATA: 216 CATG: 0 | CDS | | 144/1626 | 48/541 | missense_variant c.144_147delCATGinsTATA p.AsnMet48AsnIle | LEUM_0010 | |
| 12635 | ACGT | GCGC | GCGC: 255 ACGT: 0 | CDS | + | 969/1626 | 323/541 | synonymous_variant c.969_972delACGTinsGCGC p.GlnArg323GlnArg | LEUM_0010 | |
| 20351 | TCT | GCG | GCG: 230 TCT: 0 | CDS | + | 172/795 | 58/264 | missense_variant c.172_174delTCTinsGCG p.Ser58Ala | LEUM_0017 | |
| 22033 | AGCTA | GGCTG | GGCTG: 214 AGCTA: 0 | CDS | + | 1047/1185 | 349/394 | missense_variant c.1047_1051delAGCTAinsGGCTG p.GluAlaAsn349GluAlaAsp | LEUM_0018 | |
| 36499 | TATT | CATC | CATC: 289 TATT: 0 | CDS | + | 564/1062 | 188/353 | synonymous_variant c.564_567delTATTinsCATC p.ArgIle188ArgIle | LEUM_0044 | |
| 45902 | GTAAT GTGA | CCACA TTAC | CCACATTAC: 251 GTAATGTGA: 0 | | | | | | | |
| 47145 | TAT | TTCAG | TTCAG: 241 TAT: 0 | | | | | | | |
| 64340 | CTGT | TTGC | TTGC: 335 CTGT: 0 | CDS | – | 205/915 | 68/304 | missense_variant c.202_205delACAGinsGCAA p.ThrAsp68AlaAsn | LEUM_0076 | |
| 70144 | GGTAT GGGAT GGGA | CGTAT GGGA | CGTATGGGA: 233 GGTATGGGATGGGA: 0 | | | | | | | |
| 75797 | AGAG | GGAT | GGAT: 179 AGAG: 0 | CDS | + | 51/171 | 17/56 | missense_variant c.51_54delAGAGinsGGAT p.LeuGlu17LeuAsp | LEUM_0091 | |
| 97951 | TAAT | CAAG | CAAG: 197 TAAT: 0 | misc binding | + | | | no annotation | | |
| 138065 | GGCG | TGCA | TGCA: 279 GGCG: 0 | CDS | – | 1002/1431 | 333/476 | synonymous_variant c.999_1002delCGCCinsTGCA p.ValAla333ValAla | LEUM_0153 | |
| 138074 | AUG | GTTC | GTTC: 276 ATTG: 0 | CDS | – | 993/1431 | 330/476 | synonymous_variant c.990_993delCAATinsGAAC p.ValAsn330ValAsn | LEUM_0153 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 138092 | AACT | GACC | GACC: 278<br>AACT: 0 | CDS | − | 975/<br>1431 | 324/<br>476 | synonymous_variant<br>c.972_975delAGTTinsGGTC<br>p.ProVal324ProVal | LEUM_<br>0153 | |
| 140746 | GGGT | AGGC | AGGC: 196<br>GGGT: 0 | CDS | + | 366/<br>540 | 122/<br>179 | synonymous_variant<br>c.366_369delGGGTinsAGGC<br>p.GluGly122GluGly | LEUM_<br>0156 | |
| 140797 | CGCC | TGCT | TGCT: 208<br>CGCC: 0 | CDS | + | 417/<br>540 | 139/<br>179 | synonymous_variant<br>c.417_420delCGCCinsTGCT<br>p.AspAla139AspAla | LEUM_<br>0156 | |
| 142611 | GTT | CTG | CTG: 135<br>GTT: 0 | CDS | + | 271/<br>375 | 91/<br>124 | missense_variant<br>c.271_273delGTTinsCTG<br>p.Val91Leu | LEUM_<br>0156 | |
| 142687 | CAAAAAG | CAAAAAA | CAAAAAAA: 178<br>CAAAAAG: 0 | CDS | + | 353/<br>375 | 118/<br>124 | frameshift_variant&<br>missense_variant<br>c.353delGinsAA p.Ser118fs | LEUM_<br>0153 | |
| 145324 | CAG | AAA | AAA: 292<br>CAG: 0 | CDS | + | 505/<br>1497 | 169/<br>498 | missense_variant<br>c.505_507delCAGinsAAA<br>p.Gln169Lys | LEUM_<br>0161 | gltX |
| 162834 | TGAT | GGAC | GGAC: 260<br>TGAT: 0 | CDS | + | 2400/<br>2481 | 800/<br>826 | missense_variant<br>c.2400_2403delTGATinsGGAC<br>p.AspAsp800GluAsp | LEUM_<br>0185 | |
| 192260 | ATAAA | GTAAC | GTAAC: 301<br>ATAAA:0 | CDS | + | 433/<br>768 | 145/<br>255 | missense_variant<br>c.433_437delATAAAinsGTAAC<br>p.IleAsn145ValThr | LEUM_<br>0228 | truA |
| 196751 | CTAT | ATAC | ATAC: 138<br>CTAT: 0 | CDS | − | 55/<br>204 | 18/67 | missense_variant<br>c.52_55delATAGinsGTAT<br>p.IleAla18ValSer | LEUM_<br>0234 | |
| 196918 | AATA | GATG | GATG: 246<br>AATA: 0 | | | | | | | |
| 216494 | CACG | TACC | TACC: 230<br>CACG: 0 | CDS | + | 108/<br>978 | 36/<br>325 | synonymous_variant<br>c.108_111delCACGinsTACC<br>p.AspThr36AspThr | LEUM_<br>0256 | nrdF |
| 231792 | ATCTC | GTCTT | GTCTT: 235<br>ATCTC: 0 | CDS | + | 553/<br>1728 | 185/<br>575 | missense_variant<br>c.553_557delATCTCinsGTCTT<br>p.IleSer185ValLeu | LEUM_<br>0276 | |
| 231812 | GCTC | ACTT | ACTT: 229<br>GCTC: 0 | CDS | + | 573/<br>1728 | 191/<br>575 | synonymous_variant<br>c.573_576delGCTCinsACTT<br>p.AlaLeu191AlaLeu | LEUM_<br>0276 | |
| 234250 | ACTT | CCTG | CCTG: 217<br>ACTT: 0 | CDS | + | 336/<br>642 | 112/<br>213 | synonymous_variant<br>c.336_339delACTTinsCCTG<br>p.GlyLeu112GlyLeu | LEUM_<br>0279 | tmk |
| 242029 | CTAT | TTAC | TTAC: 265<br>CTAT: 0 | CDS | − | 664/<br>966 | 221/<br>321 | missense_variant<br>c.661_664delATAGinsGTAA<br>p.IleAla221ValThr | LEUM_<br>0287 | |
| 244287 | GACT | AACC | AACC: 251<br>GACT: 0 | CDS | + | 1436/<br>1962 | 479/<br>653 | missense_variant<br>c.1436_1439delGACTinsAACC<br>p.ArgLeu479LysPro | LEUM_<br>0288 | |
| 250392 | GGCG | AGCT | AGCT: 182<br>GGCG: 0 | CDS | + | 345/<br>1242 | 115/<br>413 | synonymous_variant<br>c.345_348delGGCGinsAGCT<br>p.ValAla115ValAla | LEUM_<br>0295 | proA |
| 271910 | TTA | CTG | CTG: 297<br>TTA: 0 | CDS | + | 358/<br>843 | 120/<br>280 | synonymous_variant<br>c.358_360delTTAinsCTG<br>p.Leu120Leu | LEUM_<br>0318 | |
| 288308 | ATA | AC | AC: 232<br>ATA: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 318676 | GATTAG | AATCAA | AATCAA: 121<br>GATTAG: 0 | CDS | + | 14/306 | 5/101 | missense_variant<br>c.14—19delGATTAGinsAATCAA<br>p.GlyLeuVal5GluSerIle | LEUM_0366 | |
| 341498 | GTTTTTTTTTA | GTTTTTTTTC | GTTTTTTTTC: 114<br>GTTTTTTTTTA: 0 | | | | | | | |
| 359500 | GCAAG | ACAAC | ACAAC: 238<br>GCAAG: 0 | CDS | + | 3034/3540 | 1012/1179 | missense_variant<br>c.3034_3038delGCAAGinsACAAC<br>p.AlaSer1012ThrThr | LEUM_0399 | |
| 366821 | ACATC | GCATT | GCATT: 250<br>ACATC: 0 | CDS | + | 957/1488 | 319/495 | synonymous_variant<br>c.957_961delACATCinsGCATT<br>plysHisLeu319LysHisLeu | LEUM_0406 | lysS |
| 366884 | AGAAGCA | GGATGCG | GGATGCG: 217<br>AGAAGCA: 0 | CDS | + | 1020/1488 | 340/495 | missense_variant<br>c.1020_1026delAGAAGCAins<br>GGATGCG<br>p.GluGluAla340GluAspAla | LEUM_0406 | lysS |
| 366896 | GTTGGCC | ATTAGCA | ATTAGCA: 225<br>GTTGGCC: 0 | CDS | + | 1032/1488 | 344/495 | synonymous_variant<br>c.1032_1038delGTTGGCCins<br>ATTAGCA<br>p.LysLeuAla344LysLeuAla | LEUM_0406 | lysS |
| 366971 | ATTTGTA | GTTCGTT | GTTCGTT: 225<br>ATTTGTA: 0 | CDS | + | 1107/1488 | 369/495 | synonymous_variant<br>c.1107_1113delATTTGTAins<br>GTTCGTT<br>p.GluPheVal369GluPheVal | LEUM_0406 | lysS |
| 371223 | CTTC | ATTT | ATTT: 226<br>CTTC: 0 | CDS | + | 273/1449 | 91/482 | synonymous_variant<br>c.273_276delCTTCinsATTT<br>p.GlyPhe91GlyPhe | LEUM_0414 | |
| 395520 | CTCT | ATCC | ATCC: 206<br>CTCT: 0 | CDS | – | 525/942 | 174/313 | missense_variant<br>c.522_525delAGAGinsGGAT<br>p.IleGlu174MetAsp | LEUM_0436 | |
| 395821 | ACCA | GCCG | GCCG: 177<br>ACCA: 0 | CDS | – | 224/942 | 74/313 | missense_variant<br>c.221_224delTGGTinsCGGC<br>p.MetVal74ThrAla | LEUM_0436 | |
| 410847 | CGGT | TGGC | TGGC: 232<br>CGGT: 0 | CDS | + | 495/1287 | 165/428 | synonymous_variant<br>c.495_498delCGGTinsTGGC<br>p.ValGly165ValGly | LEUM_0449 | |
| 420486 | CGCAC | AGCAT | AGCAT: 187<br>CGCAC: 0 | CDS | + | 200/609 | 67/202 | missense_variant<br>c.200_204delCGCAinsAGCAT<br>p.AlaHis67GluHis | LEUM_0457 | |
| 455735 | GTG | CTT | CTT: 112<br>GTG: 0 | CDS | – | 1922/2088 | 640/695 | missense_variant<br>c.1920_1922delCACinsAAG<br>p.AsnThr640LysSer | LEUM_0497 | |
| 457087 | GCCAT | ACCAC | ACCAC: 262<br>GCCAT: 0 | CDS | – | 570/2088 | 189/695 | missense_variant<br>c.566_570delATGGCinsGTGGT<br>p.AspGly189GlyGly | LEUM_0497 | |
| 490235 | GCG | ACA | ACA: 136<br>GCG: 0 | CDS | + | 142/738 | 48/245 | missense_variant<br>c.142_144delGCGinsACA<br>p.Ala48Thr | LEUM_0524 | |
| 493487 | TGGT | CGGC | CGGC: 189<br>TGGT: 0 | CDS | + | 168/834 | 56/277 | synonymous_variant<br>c.168_171delTGGTinsCGGC<br>p.ArgGly56ArgGly | LEUM_0527 | |
| 500830 | GCT | ACC | ACC: 176<br>GCT: 0 | CDS | + | 352/2031 | 118/676 | missense_variant<br>c.352_354delGCTinsACC<br>p.Ala118Thr | LEUM_0536 | |
| 502254 | CGAA | TGAG | TGAG: 214<br>CGAA: 0 | CDS | + | 1776/2031 | 592/676 | synonymous_variant<br>c.1776_1779delCGAAinsTGAG<br>p.ValGlu592ValGlu | LEUM_0536 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 502272 | CATTC | TCTCT | TCTCT: 187<br>CATTC: 0 | CDS | + | 1794/<br>2031 | 598/<br>676 | missense_variant<br>c.1794_1798delCATTCinsTCTCT<br>p.PheIleLeu598PheLeuLeu | LEUM_<br>0536 | |
| 502291 | TTG | CTA | CTA: 215<br>TTG: 0 | CDS | + | 1813/<br>2031 | 605/<br>676 | synonymous_variant<br>c.1813_1815delTTGinsCTA<br>p.Leu605Leu | LEUM_<br>0536 | |
| 505441 | AGG | GGA | GGA: 156<br>AGG: 4 | CDS | + | 826/<br>834 | 276/<br>277 | missense_variant<br>c.826_828delAGGinsGGA<br>p.Arg276Gly | LEUM_<br>0540 | |
| 507015 | ACCAC | GCCAA | GCCAA: 199<br>ACCAC: 0 | CDS | − | 507/<br>1098 | 168/<br>365 | missense_variant<br>c.503_507delGTGGTinsTTGGC<br>p.SerGly168IleGly | LEUM_<br>0543 | |
| 508582 | TGCT | CGCG | CGCG: 163<br>TGCT: 0 | CDS | + | 861/<br>1008 | 287/<br>335 | synonymous_variant<br>c.861_864delTGCTinsCGCG<br>p.ProAla287ProAla | LEUM_<br>0544 | |
| 509588 | TTG | CTA | CTA: 171<br>TTG: 0 | CDS | + | 751/<br>1866 | 251/<br>621 | synonymous_variant<br>c.751_753delTTGinsCTA<br>p.Leu251Leu | LEUM_<br>0545 | |
| 510386 | GTCATA | ATCTTG | ATCTTG: 158<br>GTCATA: 0 | CDS | + | 1549/<br>1866 | 517/<br>621 | missense_variant<br>c.1549_1554delGTCATAins<br>ATCTTG<br>p.ValIle517IleLeu | LEUM_<br>0545 | |
| 511743 | CAGC | AAGT | AAGT: 187<br>CAGC: 0 | CDS | + | 927/<br>1347 | 309/<br>448 | synonymous_variant<br>c.927_930delCAGCinsAAGT<br>p.LeuSer309LeuSer | LEUM_<br>0546 | |
| 519040 | TCGT | CCGC | CCGC: 165<br>TCGT: 0 | CDS | + | 210/<br>1371 | 70/<br>456 | synonymous_variant<br>c.210_213delTCGTinsCCGC<br>p.GlyArg70GlyArg | LEUM_<br>0553 | |
| 530354 | TTGG | GTGA | GTGA: 118<br>TTGG: 0 | CDS | + | 193/<br>1728 | 65/<br>575 | missense_variant<br>c.193_196delTTGGinsGTGA<br>p.LeuVal65ValMet | LEUM_<br>0562 | |
| 536863 | AAGA | GAGG | GAGG: 178<br>AAGA: 0 | CDS | + | 1959/<br>2301 | 653/<br>766 | synonymous_variant<br>c.1959_1962delAAGAinsGAGG<br>p.SerArg653SerArg | LEUM_<br>0566 | |
| 560132 | AAC | TAT | TAT: 202<br>AAC: 0 | CDS | + | 423/<br>882 | 141/<br>293 | missense_variant<br>c.423_425delAACinsTAT<br>p.ValThr141ValMet | LEUM_<br>0589 | |
| 603339 | AAT | GAC | GAC: 238<br>AAT: 0 | CDS | + | 673/<br>1944 | 225/<br>647 | missense_variant<br>c.673_675delAATinsGAC<br>p.Asn225Asp | LEUM_<br>0636 | |
| 607531 | GAGC | AAGT | AAGT: 217<br>GAGC: 0 | CDS | + | 438/<br>894 | 146/<br>297 | missense_variant<br>c.438_441delGAGCinsAAGT<br>p.MetSer146IleSer | LEUM_<br>0640 | |
| 610263 | TAACA | CAACG | CAACG: 174<br>TAACA: 0 | CDS | + | 773/<br>1464 | 258/<br>487 | missense_variant<br>c.773_777delTAACAinsCAACG<br>p.LeuThr258SerThr | LEUM_<br>0643 | |
| 610344 | TAGCT<br>GCAAG<br>TGCTG<br>CAAGT<br>G | CAGCT<br>GCAAG<br>TG | CAGCTGCAAGT<br>G: 127<br>TAGCTGCAAGT<br>GCTGCAAGTG:<br>0 | CDS | + | 854/<br>1464 | 285/<br>487 | missense_variant&<br>inframe_deletion<br>c.854_864delTAGCTGCAAGTinsCA<br>p.Ile285_Ser288delinsThr | LEUM_<br>0643 | |
| 613023 | CGGC | AGGT | AGGT: 209<br>CGGC: 0 | CDS | + | 801/<br>1143 | 267/<br>380 | synonymous_variant<br>c.801_804delCGGCinsAGGT<br>p.ProGly267ProGly | LEUM_<br>5064 | |
| 613326 | GACG | AACA | AACA: 160<br>GACG: 0 | CDS | + | 1104/<br>1143 | 368/<br>380 | synonymous_variant<br>c.1104_1107delGACGinsAACA<br>p.AlaThr368AlaThr | LEUM_<br>0645 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 615534 | GTTG | ATTA | ATTA: 217<br>GTTG: 0 | | | | | | | |
| 615580 | GCCC | CCCT | CCCT: 199<br>GCCC: 0 | | | | | | | |
| 641900 | TCCG | CCCA | CCCA: 199<br>TCCG: 0 | CDS | + | 417/570 | 139/189 | synonymous_variant<br>c.417_420delTCCGinsCCCA<br>p.TyrPro139TyrPro | LEUM_0673 | |
| 642442 | CAGTA | TAGCG | TAGCG: 148<br>CAGTA: 0 | CDS | + | 282/684 | 94/227 | missense_variant<br>c.282_286delCAGTAinsTAGCG<br>p.GlySerThr94GlySerAla | LEUM_0674 | |
| 654478 | CTTC | TTTT | TTTT: 217<br>CTTC: 0 | CDS | + | 597/795 | 199/264 | synonymous_variant<br>c.597_600delCTTCinsTTTT<br>p.AsnPhe199AsnPhe | LEUM_0686 | |
| 658429 | TCG | GCA | GCA: 147<br>TCG: 0 | CDS | + | 622/4314 | 208/1437 | missense_variant<br>c.622_624delTCGinsGCA<br>p.Ser208Ala | LEUM_0689 | |
| 671357 | CAGTTAT | AAGCTAC | AAGCTAC: 180<br>CAGTTAT: 0 | CDS | + | 432/891 | 144/296 | synonymous_variant<br>c.432_438delCAGTTATinsAAGCTAC<br>p.LeuSerTyr144LeuSerTyr | LEUM_0698 | |
| 697054 | AAT | CAG | CAG: 204<br>AAT: 0 | CDS | + | 2160/2217 | 720/738 | missense_variant<br>c.2160_2162delAATinsCAG<br>p.LeuIle720PheSer | LEUM_0723 | |
| 700692 | ACCC | CCCT | CCCT: 206<br>ACCC: 0 | CDS | + | 378/1527 | 126/508 | synonymous_variant<br>c.378_381delACCCinsCCCT<br>p.GlyPro126GlyPro | LEUM_0727 | purH |
| 700713 | AGCT | TGCC | TGCC: 209<br>AGCT: 0 | CDS | + | 399/1527 | 133/508 | synonymous_variant<br>c.399_402delAGCTinsTGCC<br>p.AlaAla133AlaAla | LEUM_0727 | purH |
| 701025 | CGGCAAA | TGGTAAG | TGGTAAG: 121<br>CGGCAAA: 0 | CDS | + | 711/1527 | 237/508 | synonymous_variant<br>c.711_717delCGGCAAAinsTGGTAAG<br>p.HisGlyLys237HisGlyLys | LEUM_0727 | purH |
| 723536 | CACTG | TACTC | TACTC: 162<br>CACTG: 0 | CDS | + | 326/534 | 109/177 | missense_variant<br>c.326_330delCACTGinsTACTC<br>p.ThrLeu109IleLeu | LEUM_0746 | |
| 726007 | ATAAA | TTTAT | TTTAT: 130<br>ATAAA: 0 | | | | | | | |
| 745561 | ATAAT | GTAAC | GTAAC: 87<br>ATAAT: 0 | | | | | | | |
| 751089 | ACTG | GCTA | GCTA: 157<br>ACTG: 0 | CDS | + | 2232/3339 | 744/1112 | synonymous_variant<br>c.2232_2235delACTGinsGCTA<br>p.GluLeu744GluLeu | LEUM_0774 | |
| 769650 | GCCA | ACCG | ACCG: 139<br>GCCA: 0 | CDS | – | 27/834 | 8/277 | synonymous_variant<br>c.24_27delTGGCinsCGGT<br>p.AspGly8AspGly | LEUM_0791 | |
| 784937 | CCCG | TCCA | TCCA: 96<br>CCCG: 0 | CDS | – | 1608/1674 | 535/557 | synonymous_variant<br>c.1605_1608delCGGGinsTGGA<br>p.IleGly535IleGly | LEUM_0807 | |
| 787928 | AAACG | GAACC | GAACC: 132<br>AAACG: 0 | CDS | + | 1190/1701 | 397/566 | missense_variant<br>c.1190_1194delAAACGinsGAACC<br>p.GlnThr397ArgThr | LEUM_0808 | |
| 788232 | TATCATC | CATCTTG | CATCTTG: 120<br>TATCATC: 0 | CDS | + | 1494/1701 | 498/566 | missense_variant<br>c.1494_1500delTATCATCinsCATCTTG<br>p.ThrIleIle498ThrIleLeu | LEUM_0808 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 796989 | ATTAGGC | GCTGGGT | GCTGGGT: 149<br>ATTAGGC: 0 | | | | | | | |
| 797082 | GGGA | TGGG | TGGG: 154<br>GGGA: 0 | | | | | | | |
| 797274 | TAAAA | GAAAC | GAAAC: 136<br>TAAAA: 0 | | | | | | | |
| 800184 | ACAAT | GCAAG | GCAAG: 171<br>ACAAT: 0 | CDS | + | 900/4521 | 300/1506 | missense_variant<br>c.900_904delACAATinsGCAAG<br>p.ProGlnSer300ProGlnAla | LEUM_0818 | |
| 829273 | CATTAT | AAGTAC | AAGTAC: 116<br>CATTAT: 0 | CDS | + | 211/909 | 71/302 | missense_variant<br>c.211_216delCATTATinsAAGTAC<br>p.HisTyr71LysTyr | LEUM_0842 | |
| 831087 | TAGC | CAAT | CAAT: 103<br>TAGC: 0 | CDS | − | 408/897 | 135/298 | synonymous_variant<br>c.405_408delGCTAinsATTG<br>p.ValLeu135ValLeu | LEUM_0844 | |
| 831917 | GAACAGGT | AAACCGGC | AAACCGGC: 130<br>GAACAGGT: 0 | CDS | + | 300/2025 | 100/674 | synonymous_variant<br>c.300_307delGAACAGGTins<br>AAACCGGC<br>p.GlyAsnArgLeu100GlyAsnArg<br>Leu | LEUM_0845 | |
| 832789 | GAGC | CAGT | CAGT:158<br>GAGC:0 | CDS | + | 1172/2025 | 391/674 | missense_variant<br>c.1172_1175delGAGCinsCAGT<br>p.GlyAla391AlaVal | LEUM_0845 | |
| 833573 | TATGG | CATGA | CATGA: 172<br>TATGG: 0 | CDS | + | 1956/2025 | 652/674 | missense_variant<br>c.1956_1960delTATGGinsCATGA<br>p.HisMetAla652HisMetThr | LEUM_0845 | |
| 835366 | GCAT | ACAA | ACAA: 139<br>GCAT: 0 | CDS | + | 459/1149 | 153/382 | missense_variant<br>c.459_462delGCATinsACAA<br>p.GlyHis153GlyGln | LEUM_0847 | |
| 838604 | AAGT | GAGC | GAGC: 132<br>AAGT: 0 | CDS | + | 687/729 | 229/242 | synonymous_variant<br>c.687_690delAAGTinsGAGC<br>p.GlySer229GlySer | LEUM_0849 | |
| 838832 | GGTAC | AGCAT | AGCAT: 131<br>GGTAC: 0 | CDS | + | 185/330 | 62/109 | missense_variant<br>c.185_189delGGTACinsAGCAT<br>p.GlyTyr62GluHis | LEUM_0850 | |
| 843675 | CAGATTAACG | AAAATCAAAA | AAAATCAAAA: 133<br>CAGATTAACG: 0 | CDS | + | 256/1620 | 86/539 | missense_variant<br>c.256_265delCAGATTAACGins<br>AAAATCAAAA<br>p.GlnIleAsnAla86LysIleLys<br>Thr | LEUM_0854 | |
| 843731 | GAAT | AAAC | AAAC: 158<br>GAAT: 0 | CDS | + | 312/1620 | 104/539 | synonymous_variant<br>c.312_315delGAATinsAAAC<br>p.LysAsn104LysAsn | LEUM_0854 | |
| 847585 | AACA | GACG | GACG: 149<br>AACA: 0 | CDS | + | 660/8466 | 220/2821 | synonymous_variant<br>c.660_663delAACAinsGACG<br>p.ThrThr220ThrThr | LEUM_0857 | |
| 853659 | ATA | GTG | GTG: 201<br>ATA: 0 | CDS | + | 6734/8466 | 2245/2821 | missense_variant<br>c.6734_6736delATAinsGTG<br>p.AsnAsn2245SerAsp | LEUM_0857 | |
| 863407 | GTAA | TTGC | TTGC: 77<br>GTAA: 0 | | | | | | | |
| 870920 | TC | TAT | TAT: 106<br>TC: 0 | | | | | | | |
| 876892 | ATAGCTCA | CTAGATCG | CTAGATCG: 171<br>ATAGCTCA: 0 | CDS | + | 367/2223 | 123/740 | missense_variant<br>c.367_374delATAGCTCAins<br>CTAGATCG<br>p.IleAlaHis123LeuAspArg | LEUM_0882 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 877704 | CGCC | TGCT | TGCT: 185<br>CGCC: 0 | CDS | + | 1179/<br>2223 | 393/<br>740 | synonymous_variant<br>c.1179_1182delCGCCinsTGCT<br>p.TyrAla393TyrAla | LEUM_<br>0882 | |
| 880042 | ACTAT | TCTAC | TCTAC: 151<br>ACTAT: 0 | CDS | | 77/<br>1506 | 26/<br>501 | missense_variant<br>c.77_81delACTATinsTCTAC<br>p.AsnTyr26IleTyr | LEUM_<br>0884 | |
| 883034 | ACCAC<br>TT | GCCGC<br>TC | GCCGCTC: 136<br>ACCACTT: 0 | CDS | + | 1422/<br>2253 | 474/<br>750 | missense_variant<br>c.1422_1428delACCACTTins<br>GCCGCTC<br>p.IleProLeu474MetProLeu | LEUM_<br>0885 | |
| 883123 | GAGA | AAGG | AAGG: 126<br>GAGA: 0 | CDS | + | 1511/<br>2253 | 504/<br>750 | missense_variant<br>c.1511_1514delGAGAinsAAGG<br>p.ArgGlu504LysGly | LEUM_<br>0885 | |
| 893725 | TAA | CAG | CAG: 132<br>TAA: 0 | CDS | + | 1167/<br>2259 | 389/<br>752 | missense_variant<br>c.1167_1169delTAAinsCAG<br>p.AlaLys389AlaArg | LEUM_<br>0894 | |
| 894794 | AAA | GAG | GAG: 173<br>AAA: 0 | CDS | + | 2236/<br>2259 | 746/<br>752 | missense_variant<br>c.2236_2238delAAAinsGAG<br>p.Lys746Glu | LEUM_<br>0894 | |
| 895508 | CAAG | TAAA | TAAA: 112<br>CAAG: 0 | CDS | + | 675/<br>687 | 225/<br>228 | synonymous_variant<br>c.675_678delCAAGinsTAAA<br>p.IleLys225IleLys | LEUM_<br>0895 | |
| 895583 | ATTAA<br>GCG | GTCAA<br>GTT | GTCAAGTT: 92<br>ATTAAGCG: 0 | CDS | − | 996/<br>1008 | 330/<br>335 | missense_variant<br>c.989_996delCGCTTAATins<br>AACTTGAC<br>p.ThrLeuAsn330LysLeuAsp | LEUM_<br>0896 | |
| 895607 | CGGT | TGGG | TGGG: 101<br>CGGT: 0 | CDS | − | 972/<br>1008 | 323/<br>335 | synonymous_variant<br>c.969_972delACCGinsCCCA<br>p.ValPro323ValPro | LEUM_<br>0896 | |
| 903892 | CTTTG<br>CCTT | TTTTA<br>CCTC | TTTTACCT<br>C: 158<br>CMGCCTT: 0 | CDS | + | 1215/<br>1839 | 405/<br>612 | missense_variant<br>c.1215_1223delCTTTGCCTTins<br>TTTTACCTC<br>p.AlaPheAlaLeu405AlaPheThr<br>Ser | LEUM_<br>0901 | |
| 907285 | GCTAC | ACTAT | ACTAT: 127<br>GCTAC: 0 | | | | | | | |
| 911930 | CAGC | TAGT | TAGT: 94<br>CAGC: 0 | CDS | + | 39/<br>822 | 13/<br>273 | synonymous_variant<br>c.39_42delCAGCinsTAGT<br>p.SerSer13SerSer | LEUM_<br>0909 | |
| 933210 | CAGGG<br>C | GAGCG<br>T | GAGCGT: 156<br>CAGGGC:0 | CDS | + | 1909/<br>1992 | 637/<br>663 | missense_variant<br>c.1909_1914delCAGGGCins<br>GAGCGT<br>p.GlnGly637GluArg | LEUM_<br>0929 | |
| 945839 | TAG | TAAA | TAAA: 60<br>TAG: 0 | | | | | | | |
| 945853 | GAT | AAC | AAC: 61<br>GAT: 0 | | | | | | | |
| 972869 | CATT | TATC | TATC: 142<br>CATT: 0 | CDS | + | 168/<br>480 | 56/<br>159 | synonymous_variant<br>c.168_171delCATTinsTATC<br>p.HisIle56HisIle | LEUM_<br>0972 | |
| 980203 | TTAGT<br>A | CTGGT<br>G | CTGGTG: 85<br>TTAGTA: 0 | CDS | + | 220/<br>513 | 74/<br>170 | synonymous_variant<br>c.220_225delTTAGTAinsCTGGTG<br>p.LeuVal74LeuVal | LEUM_<br>0980 | |
| 980531 | TCATT<br>A | CAATT<br>G | CAATTG: 125<br>TCATTA: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 982914 | AGCT | GGCA | GGCA: 58<br>AGCT: 0 | CDS | + | | | no annotation | LEUM_0984 | |
| 986252 | GGTCC | TGTCT | TGTCT: 31<br>GGTCC: 0 | CDS | + | | | no annotation | LEUM_0987 | |
| 986279 | CGAAACGCTCATTC | TGAGACACTAATTA | TGAGACACTAATTA: 30<br>CGAAACGCTCATTC: 0 | CDS | + | | | no annotation | LEUM_0987 | |
| 986308 | GGTC | AGAT | AGAT: 30<br>GGTC: 0 | | | | | | | |
| 986319 | ATT | GTC | GTC: 31<br>ATT: 0 | CDS | + | | | no annotation | LEUM_0988 | |
| 986356 | CGTT | TGTG | TGTG: 30<br>CGTT: 0 | CDS | + | | | no annotation | LEUM_0988 | |
| 986375 | GTTTCAGAAAAA | ATGTCGGAAGAG | ATGTCGGAAGAG: 25<br>GTTTCAGAAAAA: 0 | CDS | + | | | no annotation | LEUM_0988 | |
| 1008480 | CAAG | TAAA | TAAA: 14<br>CAAG: 0 | CDS | + | | | no annotation | LEUM_1008 | |
| 1008786 | CCTG | TCTA | TCTA: 1619<br>CCTG: 0 | CDS | + | | | no annotation | LEUM_1009 | |
| 1008954 | ACCC | GCCA | GCCA: 1877<br>ACCC: 0 | CDS | + | | | no annotation | LEUM_1009 | |
| 1022214 | TUG | ATTA | ATTA: 76<br>TTTG: 0 | | | | | | | |
| 1135118 | TGG | CGA | CGA: 83<br>TGG: 0 | | | | | | | |
| 1135159 | TCGT | CCGC | CCGC: 83<br>TCGT: 0 | | | | | | | |
| 1135269 | TTAC | CTAT | CTAT: 123<br>TTAC: 0 | CDS | + | | | no annotation | LEUM_1138 | |
| 1138281 | GTTT | ATTC | ATTC: 201<br>GTTT: 0 | CDS | − | | | no annotation | LEUM_1142 | |
| 1139585 | CAACC | TAACT | TAACT: 197<br>CAACC: 0 | CDS | − | | | no annotation | LEUM_1143 | |
| 1155368 | AGCG | GGCA | GGCA: 141<br>AGCG: 0 | CDS | − | | | no annotation | LEUM_1157 | |
| 1157871 | ATTT | GTTG | GTTG: 155<br>ATTT: 0 | CDS | − | | | no annotation | LEUM_1161 | |
| 1169465 | GTCG | TTCT | TTCT: 178<br>GTCG: 0 | CDS | − | | | no annotation | LEUM_1172 | |
| 1170652 | GCG | TCA | TCA: 135<br>GCG: 0 | CDS | − | | | no annotation | LEUM_1173 | |
| 1170669 | TATC | CATT | CATT: 124<br>TATC: 0 | CDS | − | | | no annotation | LEUM_1173 | |
| 1170980 | TTTA | CTCG | CTCG: 123<br>TTTA: 0 | CDS | − | | | no annotation | LEUM_1174 | |
| 1174201 | GAC | AAT | AAT: 87<br>GAC: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1174261 | CGTG | AGTA | AGTA: 130 CGTG: 0 | CDS | − | | | no annotation | LEUM_1177 | |
| 1183816 | GGTA | AGTG | AGTG: 139 GGTA: 0 | CDS | − | | | no annotation | LEUM_1187 | |
| 1194019 | GCAAT | ACAAC | ACAAC: 139 GCAAT: 0 | CDS | − | | | no annotation | LEUM_1195 | |
| 1238393 | GGCAGG | AGTAGA | AGTAGA: 81 GGCAGG: 0 | | | | | | | |
| 1238441 | TAAT | GATA | GATA: 47 TAAT: 0 | | | | | | | |
| 1258437 | CTT | TTG | TTG: 43 CTT: 0 | | | | | | | |
| 1263043 | TGGG | CGGA | CGGA: 194 TGGG: 0 | CDS | + | | | no annotation | LEUM_1275 | |
| 1267583 | TGGGCAG | GGGTCAA | GGGTCAA: 131 TGGGCAG: 0 | CDS | + | | | no annotation | LEUM_1279 | |
| 1289296 | TCTC | CCU | CCTT: 197 TCTC: 0 | CDS | − | | | no annotation | LEUM_1302 | |
| 1294486 | ACAA | GCA | GCA: 189 ACAA: 0 | | | | | | | |
| 1296449 | CAGCTGTA | TATCCGTG | TATCCGTG: 188 CAGCTGTA: 0 | CDS | − | | | no annotation | LEUM_1309 | aspS |
| 1302442 | TCCG | ACCA | ACCA: 161 TCCG: 0 | CDS | − | | | no annotation | LEUM_1314 | |
| 1303222 | AGTA | GGTG | GGTG: 220 AGTA: 0 | CDS | − | | | no annotation | LEUM_1314 | |
| 1306063 | TACC | GACA | GACA: 193 TACC: 0 | CDS | − | | | no annotation | LEUM_1316 | lacZ |
| 1319219 | TACAGCAA | CACATCAC | CACATCAC: 135 TACAGCAA: 0 | | | | | | | |
| 1319558 | ATTTAAGTTCAGTCACA | CTACAATATCACTTCCC | CTACAATATCACTTCCC: 109 ATTTAAGTTCAGTCACA: 0 | | | | | | | |
| 1319611 | ACGTCT | CCGTTC | CCGTTC: 146 ACGTCT: 0 | | | | | | | |
| 1319951 | ACGC | GCGT | GCGT: 150 ACGC: 0 | CDS | + | | | no annotation | LEUM_1334 | |
| 1345228 | ACTTG | GCTTA | GCTTA: 204 ACTTG: 0 | CDS | − | | | no annotation | LEUM_1363 | |
| 1346846 | TGGG | CGGA | CGGA: 191 TGGG: 0 | CDS | − | | | no annotation | LEUM_1363 | |
| 1392214 | TAAA | AAGC | AAGC: 157 TAAA: 0 | CDS | − | | | no annotation | LEUM_1404 | |
| 1396399 | CGC | TGT | TGT: 177 CGC: 0 | CDS | − | | | no annotation | LEUM_1408 | |
| 1407216 | TGA | AGC | AGC: 120 TGA: 0 | CDS | − | | | no annotation | LEUM_1412 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1407234 | TGTTAGT | AGCTAAC | AGCTAAC: 94<br>TGTTAGT: 0 | CDS | − | | | no annotation | LEUM_1412 | |
| 1407252 | AATG | GATA | GATA: 112<br>AATG: 0 | CDS | − | | | no annotation | LEUM_1412 | |
| 1410440 | GCTT | ACTC | ACTC: 158<br>GCTT: 0 | CDS | − | | | no annotation | LEUM_1415 | |
| 1410471 | CTT | ATC | ATC: 162<br>CTT: 0 | CDS | − | | | no annotation | LEUM_1415 | |
| 1415069 | TTTC | CTTA | CTTA: 140<br>TTTC: 0 | CDS | − | | | no annotation | LEUM_1420 | |
| 1415084 | CACT | AACA | AACA: 142<br>CACT: 0 | CDS | − | | | no annotation | LEUM_1420 | |
| 1415294 | AAGT | TAGC | TAGC: 163<br>AAGT: 0 | CDS | − | | | no annotation | LEUM_1420 | |
| 1415654 | GTAC | ATAA | ATAA: 203<br>GTAC: 0 | CDS | − | | | no annotation | LEUM_1420 | |
| 1415711 | AGCT | CGCC | CGCC: 184<br>AGCT: 0 | CDS | − | | | no annotation | LEUM_1420 | |
| 1415881 | AAC | GAA | GAA: 192<br>AAC: 0 | | | | | | | |
| 1416065 | GCCT | TCCA | TCCA: 207<br>GCCT: 0 | CDS | − | | | no annotation | LEUM_1421 | |
| 1416263 | GTTT | ATTA | ATTA: 191<br>GTTT: 0 | CDS | − | | | no annotation | LEUM_1421 | |
| 1416317 | GATG | AATA | AATA: 199<br>GATG: 0 | CDS | − | | | no annotation | LEUM_1421 | |
| 1416380 | CAAA | TAAG | TAAG: 211<br>CAAA: 0 | CDS | − | | | no annotation | LEUM_1421 | |
| 1416695 | TGTT | GGTC | GGTC: 168<br>TGTT: 0 | CDS | − | | | no annotation | LEUM_1421 | |
| 1417341 | AUG | GTTA | GTTA: 195<br>ATTG: 0 | CDS | − | | | no annotation | LEUM_1422 | |
| 1417434 | ATTA | GTTG | GTTG: 217<br>ATTA: 0 | CDS | − | | | no annotation | LEUM_1422 | |
| 1417596 | CAG | TAA | TAA: 222<br>CAG: 0 | CDS | − | | | no annotation | LEUM_1423 | |
| 1417722 | AAGGAGA | GAGAAGT | GAGAAGT: 134<br>AAGGAGA: 0 | CDS | − | | | no annotation | LEUM_1423 | |
| 1417734 | CAACGTT | GTGTGTC | GTGTGTC: 128<br>CAACGTT: 0 | CDS | − | | | no annotation | LEUM_1423 | |
| 1417782 | GTCT | ATCC | ATCC: 185<br>GTCT: 0 | CDS | − | | | no annotation | LEUM_1423 | |
| 1417965 | CTTGTCA | TTTATCG | TTTATCG: 206<br>CTTGTCA: 0 | CDS | − | | | no annotation | LEUM_1423 | |
| 1418013 | GCCA | ACCG | ACCG: 208<br>GCCA: 0 | CDS | − | | | no annotation | LEUM_1423 | |
| 1418025 | GGCG | AGCA | AGCA: 180<br>GGCG: 0 | CDS | − | | | no annotation | LEUM_1423 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1418040 | TAAAGCCTCTTG | CAGAGCAGCTTC | CAGAGCAGCTTC: 88<br>TAAAGCCTCTTG: 0 | CDS | - | | | no annotation | LEUM_1423 | |
| 1418061 | TTG | CTC | CTC: 91<br>TTG: 0 | CDS | - | | | no annotation | LEUM_1423 | |
| 1418069 | GACCGGCA | ACCCTGCG | ACCCTGCG: 89<br>GACCGGCA: 0 | CDS | - | | | no annotation | LEUM_1423 | |
| 1418094 | TCCC | ACCT | ACCT: 100<br>TCCC: 0 | CDS | - | | | no annotation | LEUM_1423 | |
| 1418103 | TAAG | CAGA | CAGA: 87<br>TAAG: 0 | CDS | - | | | no annotation | LEUM_1423 | |
| 1418148 | CGCG | TGCA | TGCA: 197<br>CGCG: 0 | CDS | - | | | no annotation | LEUM_1423 | |
| 1418160 | GCCA | ACCG | ACCG: 194<br>GCCA: 0 | CDS | - | | | no annotation | LEUM_1423 | |
| 1418193 | GTGCAA | ATTTAG | ATTTAG: 162<br>GTGCAA: 0 | CDS | - | | | no annotation | LEUM_1423 | |
| 1418208 | ATGG | CTGA | CTGA: 175<br>ATGG: 0 | CDS | - | | | no annotation | LEUM_1423 | |
| 1418271 | TTTT | ATCC | ATCC: 170<br>TTTT: 0 | CDS | - | | | no annotation | LEUM_1423 | |
| 1418322 | TTTA | CTTG | CTTG: 167<br>TTTA: 0 | CDS | - | | | no annotation | LEUM_1423 | |
| 1418385 | AGAG | GGAA | GGAA: 118<br>AGAG: 0 | CDS | - | | | no annotation | LEUM_1423 | |
| 1418582 | ACC | GCT | GCT: 210<br>ACC: 0 | CDS | - | | | no annotation | LEUM_1424 | |
| 1418878 | TGCCTCG | AGTCTCA | AGTCTCA: 149<br>TGCCTCG: 0 | CDS | - | | | no annotation | LEUM_1424 | |
| 1418950 | ACTC | GCTT | GCTT: 163<br>ACTC: 0 | CDS | - | | | no annotation | LEUM_1424 | |
| 1419097 | CCTA | TCTG | TCTG: 175<br>CCTA: 0 | CDS | - | | | no annotation | LEUM_1424 | |
| 1419197 | GTGCT | TTGCC | TTGCC: 208<br>GTGCT: 0 | CDS | - | | | no annotation | LEUM_1424 | |
| 1419226 | GTTA | AUG | ATTG: 221<br>GTTA: 0 | CDS | - | | | no annotation | LEUM_1424 | |
| 1419311 | TCG | GCC | GCC: 230<br>TCG: 0 | CDS | - | | | no annotation | LEUM_1424 | |
| 1419388 | GCTT | ACTG | ACTG: 223<br>GCTT: 0 | CDS | - | | | no annotation | LEUM_1424 | |
| 1419438 | TTTTAG | GTTG | GTTG: 162<br>TTTTAG: 0 | CDS | - | | | no annotation | LEUM_1424 | |
| 1429917 | TGGCTCCTCTATTTGTCTTT | AGGCACCTTTAGTCGTTTTA | AGGCACCTTTAGTCGTTTTA: 173<br>TGGCTCCTCTATTTGTCTTT: 0 | CDS | - | | | no annotation | LEUM_1434 | |
| 1429993 | TGTG | CGTA | CGTA: 204<br>TGTG: 0 | CDS | - | | | no annotation | LEUM_1434 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1430085 | AGAGT | GGAGC | GGAGC: 169 AGAGT: 0 | CDS | - | | | no annotation | LEUM_1434 | |
| 1430128 | GTTG | ATTA | ATTA: 172 GTTG: 0 | CDS | - | | | no annotation | LEUM_1434 | |
| 1430143 | AGACGTG | GGCTGTA | GGCTGTA: 153 AGACGTG: 0 | CDS | - | | | no annotation | LEUM_1434 | |
| 1430176 | CTCT | TTCA | TTCA: 177 CTCT: 0 | CDS | - | | | no annotation | LEUM_1434 | |
| 1430203 | CCCG | TCCA | TCCA: 186 CCCG: 0 | CDS | - | | | no annotation | LEUM_1434 | |
| 1430314 | AGCTGTGACC | GGCAGTCACT | GGCAGTCACT: 192 AGCTGTGACC: 0 | CDS | - | | | no annotation | LEUM_1434 | |
| 1430344 | CAAC | TAAG | TAAG: 206 CAAC: 0 | CDS | - | | | no annotation | LEUM_1434 | |
| 1430374 | TTCG | CTCA | CTCA: 216 TTCG: 0 | CDS | - | | | no annotation | LEUM_1434 | |
| 1430413 | TAAA | CAAG | CAAG: 214 TAAA: 0 | CDS | - | | | no annotation | LEUM_1434 | |
| 1430623 | CTCT | TTCA | TTCA: 192 CTCT: 0 | CDS | - | | | no annotation | LEUM_1435 | |
| 1430785 | AACCAATCCT | TACAAAACCA | TACAAAACCA: 159 AACCAATCCT: 0 | CDS | - | | | no annotation | LEUM_1435 | |
| 1430806 | CAA | TAG | TAG: 183 CAA: 0 | CDS | - | | | no annotation | LEUM_1435 | |
| 1430942 | TTAGAATC | GTAGGATT | GTAGGATT: 180 TTAGAATC: 0 | CDS | - | | | no annotation | LEUM_1435 | |
| 1431011 | CTTTTT | TCTTTC | TCTTTC: 161 CTTTTT: 0 | CDS | - | | | no annotation | LEUM_1435 | |
| 1431073 | CTTA | TTTT | TTTT: 160 CTTA: 0 | CDS | - | | | no annotation | LEUM_1435 | |
| 1431088 | CAGA | TAGG | TAGG: 142 CAGA: 0 | CDS | - | | | no annotation | LEUM_1435 | |
| 1431356 | AAC | TAT | TAT: 129 AAC: 0 | CDS | - | | | no annotation | LEUM_1435 | |
| 1431525 | TTT | CTC | CTC: 143 TTT: 0 | CDS | - | | | no annotation | LEUM_1436 | |
| 1431755 | CACC | TACT | TACT: 154 CACC: 0 | CDS | - | | | no annotation | LEUM_1436 | |
| 1431803 | CGTA | TGTG | TGTG: 139 CGTA: 0 | CDS | - | | | no annotation | LEUM_1436 | |
| 1432287 | GCAAA | ACAAT | ACAAT: 162 GCAAA: 0 | | | | | | | |
| 1432326 | AAAC | TACT | TACT: 140 AAAC: 0 | | | | | | | |
| 1432336 | TAAAA | GAAAG | GAAAG: 143 TAAAA: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1432349 | TATG | CATA | CATA: 141 TATG: 0 | CDS | − | | | no annotation | LEUM_1437 | |
| 1432378 | CTGA | TTGG | TTGG: 207 CTGA: 0 | CDS | − | | | no annotation | LEUM_1437 | |
| 1432717 | AAT | CAC | CAC: 213 AAT: 0 | CDS | − | | | no annotation | LEUM_1437 | |
| 1433379 | CCA | GCG | GCG: 209 CCA: 0 | CDS | − | | | no annotation | LEUM_1438 | |
| 1433417 | GGACTTA | AGATTTG | AGATTTG: 205 GGACTTA: 0 | CDS | − | | | no annotation | LEUM_1438 | |
| 1433441 | CACA | TACG | TACG: 222 CACA: 0 | CDS | − | | | no annotation | LEUM_1438 | |
| 1433984 | CGTG | TGTA | TGTA: 206 CGTG: 0 | CDS | − | | | no annotation | LEUM_1438 | |
| 1436006 | AAAG | GAAA | GAAA: 254 AAAG: 0 | CDS | − | | | no annotation | LEUM_1440 | |
| 1436796 | CAA | TAC | TAC: 92 CAA: 0 | | | | | | | |
| 1437736 | CAAA | TAAG | TAAG: 245 CAAA: 0 | CDS | − | | | no annotation | LEUM_1443 | |
| 1437751 | CTTA | TTTG | TTTG: 249 CTTA: 0 | CDS | − | | | no annotation | LEUM_1443 | |
| 1441725 | CGCTT | TGCTTT | TGC1TT: 165 CGCTT: 0 | | | | | | | |
| 1444575 | CAAAAAAAAAAAAC | CAAAAAAAAAAC | CAAAAAAACAAAC: 127 CAAAAAAAAAAAAC: 0 | | | | | | | |
| 1447932 | AAAC | GAAT | GAAT: 203 AAAC: 0 | CDS | − | | | no annotation | LEUM_1454 | |
| 1474016 | TTAAC | CTAAT | CTAAT: 171 TTAAC: 0 | CDS | − | | | no annotation | LEUM_1480 | |
| 1475011 | TAGT | CAGC | CAGC: 175 TAGT: 0 | CDS | − | | | no annotation | LEUM_1481 | |
| 1475048 | TGTG | CGTT | CGTT: 194 TGTG: 0 | CDS | − | | | no annotation | LEUM_1481 | |
| 1475219 | TTGT | CTGC | CTGC: 188 TTGT: 0 | CDS | − | | | no annotation | LEUM_1481 | |
| 1477474 | TTAAC | CTAAA | CTAAA: 148 TTAAC: 0 | CDS | − | | | no annotation | LEUM_1481 | |
| 1501570 | AGATC | GCATG | GCATG: 145 AGATC: 0 | CDS | − | | | no annotation | LEUM_1502 | |
| 1501590 | ACA | GCG | GCG: 140 ACA: 0 | CDS | − | | | no annotation | LEUM_1502 | |
| 1510576 | TAAT | CAAA | CAAA: 199 TAAT: 0 | CDS | − | | | no annotation | LEUM_1513 | |
| 1518189 | AGGC | GGGT | GGGT: 152 AGGC: 0 | CDS | − | | | no annotation | LEUM_1520 | engB |
| 1519140 | AGCA | GGCT | GGCT: 222 AGCA: 0 | CDS | − | | | no annotation | LEUM_1521 | clpX |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1519209 | GGAG | AGAT | AGAT: 236<br>GGAG: 0 | CDS | − | | | no annotation | LEUM_1521 | clpX |
| 1527336 | GTCC | ATCT | ATCT: 171<br>GTCC: 0 | CDS | − | | | no annotation | LEUM_1529 | |
| 1539200 | GAAA | AAAG | AAAG: 234<br>GAAA: 0 | CDS | − | | | no annotation | LEUM_1539 | |
| 1548015 | CAAACT | AGAACA | AGAACA: 112<br>CAAACT: 0 | CDS | + | | | no annotation | LEUM_1546 | |
| 1553910 | AATT | GATA | GATA: 154<br>AATT: 0 | CDS | − | | | no annotation | LEUM_1554 | |
| 1563023 | ATAG | TTAA | TTAA: 147<br>ATAG: 0 | | | | | | | |
| 1563156 | CCCC | TCCT | TCCT: 161<br>CCCC: 0 | CDS | − | | | no annotation | LEUM_1564 | |
| 1563399 | ACCG | GCCC | GCCC: 202<br>ACCG: 0 | CDS | − | | | no annotation | LEUM_1564 | |
| 1570912 | GGGA | AGGG | AGGG: 201<br>GGGA: 0 | CDS | − | | | no annotation | LEUM_1569 | |
| 1575438 | GCAAA | ACAAG | ACAAG: 118<br>GCAAA: 0 | | | | | | | |
| 1576436 | TTCT | CTCC | CTCC: 188<br>TTCT: 0 | CDS | − | | | no annotation | LEUM_1575 | |
| 1576450 | GTATA | ATATC | ATATC: 188<br>GTATA: 0 | CDS | − | | | no annotation | LEUM_1575 | |
| 1576582 | CCTC | ACTT | ACTT: 201<br>CCTC: 0 | CDS | − | | | no annotation | LEUM_1575 | |
| 1582261 | CACA | GACG | GACG: 210<br>CACA: 0 | CDS | − | | | no annotation | LEUM_1578 | |
| 1582441 | TACTGCA | CACCGCG | CACCGCG: 178<br>TACTGCA: 0 | CDS | − | | | no annotation | LEUM_1578 | |
| 1589522 | ACTGC | GCCGT | GCCGT: 119<br>ACTGC: 0 | CDS | − | | | no annotation | LEUM_1586 | |
| 1622472 | TTATAT | ACGTAC | ACGTAC: 247<br>TTATAT: 0 | CDS | − | | | no annotation | LEUM_1624 | |
| 1624045 | AGCCTAC | GCCCGAT | GCCCGAT: 111<br>AGCCTAC: 0 | CDS | − | | | no annotation | LEUM_1627 | |
| 1624058 | CAAG | GAGA | GAGA: 110<br>CAAG: 0 | CDS | − | | | no annotation | LEUM_1627 | |
| 1624079 | TATT | AATCA | AATCA: 164<br>TATT: 0 | | | | | | | |
| 1624096 | ATTA | GTTG | GTTG: 184<br>ATTA: 0 | | | | | | | |
| 1624117 | TAG | CAA | CAA: 203<br>TAG: 0 | | | | | | | |
| 1624234 | GCCGCCA | ACCACCG | ACCACCG: 231<br>GCCGCCA: 0 | CDS | − | | | no annotation | LEUM_1628 | |
| 1624336 | TTGA | CTGG | CTGG: 149<br>TTGA: 0 | CDS | − | | | no annotation | LEUM_1628 | |
| 1624351 | ATTACCA | GTTCCCG | GTTCCCG: 149<br>ATTACCA: 0 | CDS | − | | | no annotation | LEUM_1628 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1624431 | TGTTG | AGTTA | AGTTA: 98<br>TGTTG: 0 | CDS | - | | | no annotation | LEUM_1628 | |
| 1624459 | CTTA | TTGT | TTGT: 84<br>CTTA: 0 | CDS | - | | | no annotation | LEUM_1628 | |
| 1624574 | TTG | GTA | GTA: 149<br>TTG: 0 | CDS | - | | | no annotation | LEUM_1628 | |
| 1624609 | GCCG | TCCA | TCCA: 180<br>GCCG: 0 | CDS | - | | | no annotation | LEUM_1628 | |
| 1624618 | TCCG | GCCA | GCCA: 193<br>TCCG: 0 | CDS | - | | | no annotation | LEUM_1628 | |
| 1624654 | GTTGGAA | ATTTGAG | ATTTGAG: 220<br>GTTGGAA: 0 | CDS | - | | | no annotation | LEUM_1628 | |
| 1624720 | TAA | CAT | CAT: 230<br>TAA: 0 | CDS | - | | | no annotation | LEUM_1628 | |
| 1624729 | AGCG | GGCA | GGCA: 229<br>AGCG: 0 | CDS | - | | | no annotation | LEUM_1628 | |
| 1624843 | TAG | CAA | CAA: 250<br>TAG: 0 | CDS | - | | | no annotation | LEUM_1628 | |
| 1624858 | ATTA | GTTG | GTTG: 243<br>ATTA: 0 | CDS | - | | | no annotation | LEUM_1628 | |
| 1624900 | TGCG | AGCA | AGCA: 250<br>TGCG: 0 | CDS | - | | | no annotation | LEUM_1628 | |
| 1624918 | GGCTAGC | AGCCAGT | AGCCAGT: 239<br>GGCTAGC: 0 | CDS | - | | | no annotation | LEUM_1628 | |
| 1624978 | CACCGAG | GACTGAA | GACTGAA: 222<br>CACCGAG: 0 | CDS | - | | | no annotation | LEUM_1628 | |
| 1625140 | AAACGAA | GAATGAG | GAATGAG: 202<br>AAACGAA: 0 | CDS | - | | | no annotation | LEUM_1628 | |
| 1625152 | ATAATTTGC | GTAGCTTGT | GTAGCTTGT: 206<br>ATAATTTGC: 0 | CDS | - | | | no annotation | LEUM_1628 | |
| 1625209 | CACG | TACA | TACA: 233<br>CACG: 0 | CDS | - | | | no annotation | LEUM_1628 | |
| 1629235 | GATG | TATA | TATA: 176<br>GATG: 0 | CDS | - | | | no annotation | LEUM_1635 | |
| 1629250 | ATTA | GTTG | GTTG: 180<br>ATTA: 0 | CDS | - | | | no annotation | LEUM_1635 | |
| 1629328 | TGTGTTCAAAGAT | CATATTTAGAGAC | CATATTTAGAGAC: 159<br>TGTGTTCAAAGAT: 0 | CDS | - | | | no annotation | LEUM_1635 | |
| 1629619 | TAATGCG | CAGTGCA | CAGTGCA: 203<br>TAATGCG: 0 | CDS | - | | | no annotation | LEUM_1635 | |
| 1629658 | TATC | GATT | GATT: 223<br>TATC: 0 | CDS | - | | | no annotation | LEUM_1635 | |
| 1629722 | ACACCTG | TCTGCTAA | TCTGCTAA: 130<br>ACACCTG: 0 | CDS | - | | | no annotation | LEUM_1635 | |
| 1629759 | ATGA | GTGC | GTGC: 191<br>ATGA: 0 | CDS | - | | | no annotation | LEUM_1635 | |
| 1650708 | TAAC | AAAT | AAAT: 59<br>TAAC: 0 | CDS | - | | | no annotation | LEUM_1656 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1650750 | AGGAATCGTTCA | ATAGATTGGCTCG | ATAGATTGGCTCG: 35 AGGAATCGTTCA: 0 | | | | | | | |
| 1650948 | ACGCATT | GCGCCTC | GCGCCTC: 199 ACGCATT: 0 | CDS | − | | | no annotation | LEUM_1657 | |
| 1651008 | AUG | GTTA | GTTA: 221 ATTG: 0 | CDS | − | | | no annotation | LEUM_1657 | |
| 1651041 | TAT | CAC | CAC: 223 TAT: 0 | CDS | − | | | no annotation | LEUM_1657 | |
| 1651098 | ATA | GTC | GTC: 188 ATA: 0 | | | | | | | |
| 1651117 | GTGCA | GATA | GATA: 133 GTGCA: 0 | | | | | | | |
| 1651140 | GCCA | ACCG | ACCG: 210 GCCA: 0 | | | | | | | |
| 1651201 | TTCC | CTCT | CTCT: 224 TTCC: 0 | CDS | − | | | no annotation | LEUM_1658 | |
| 1656232 | GCCT | ACCC | ACCC: 197 GCCT: 0 | CDS | − | | | no annotation | LEUM_1671 | |
| 1661069 | CACT | AACC | AACC: 262 CACT: 0 | CDS | − | | | no annotation | LEUM_1680 | |
| 1665094 | TTTTAAACCGTCA | CTTCAAATCATCG | CTTCAAATCATCG: 164 TTTTAAACCGTCA: 0 | CDS | + | | | no annotation | LEUM_1690 | |
| 1665117 | CTTCC | ATTCA | ATTCA: 176 CTTCC: 0 | CDS | + | | | no annotation | LEUM_1690 | |
| 1665274 | GTACGGC | ATATGGG | ATATGGG: 200 GTACGGC: 0 | CDS | + | | | no annotation | LEUM_1690 | |
| 1665286 | CCAC | TCAT | TCAT: 208 CCAC: 0 | CDS | + | | | no annotation | LEUM_1690 | |
| 1665328 | CGGA | TGGC | TGGC: 200 CGGA: 0 | CDS | + | | | no annotation | LEUM_1690 | |
| 1665337 | GAAAGACGCT | AAAGGATGCC | AAAGGATGCC: 196 GAAAGACGCT: 0 | CDS | + | | | no annotation | LEUM_1690 | |
| 1665424 | GAAA | AAAG | AAAG: 171 GAAA: 0 | CDS | + | | | no annotation | LEUM_1690 | |
| 1665436 | GTATG | ATACA | ATACA: 144 GTATG: 0 | CDS | + | | | no annotation | LEUM_1690 | |
| 1665448 | CAAGCGC | TAAACGT | TAAACGT: 139 CAAGCGC: 0 | CDS | + | | | no annotation | LEUM_1690 | |
| 1665484 | ACCTACC | GCCAACT | GCCAACT: 153 ACCTACC: 0 | CDS | + | | | no annotation | LEUM_1690 | |
| 1665529 | TTTA | AUG | ATTG: 168 TTTA: 0 | CDS | + | | | no annotation | LEUM_1690 | |
| 1665572 | AGAAC | GGAAT | GGAAT: 198 AGAAC: 0 | CDS | + | | | no annotation | LEUM_1690 | |
| 1665664 | GGG | AGA | AGA: 206 GGG: 0 | CDS | + | | | no annotation | LEUM_1690 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1665752 | TTACAA | CTGCAG | CTGCAG: 201<br>TTACAA: 0 | CDS | + | | | no annotation | LEUM_1690 | |
| 1665790 | GATTACT | AATAACA | AATAACA: 195<br>GATTACT: 0 | CDS | + | | | no annotation | LEUM_1690 | |
| 1665814 | TAGT | CAGC | CAGC: 202<br>TAGT: 0 | CDS | + | | | no annotation | LEUM_1690 | |
| 1666025 | TTAT | ATAC | ATAC: 134<br>TTAT: 0 | | | | | | | |
| 1667151 | TAAAAAAT | TAAAAAAG | TAAAAAAG: 78<br>TAAAAAAT: 0 | | | | | | | |
| 1669413 | AAACA | GAACG | GAACG: 158<br>AAACA: 0 | CDS | + | | | no annotation | LEUM_1695 | |
| 1670484 | ACCT | TCCC | TCCC: 177<br>ACCT: 0 | CDS | + | | | no annotation | LEUM_1696 | |
| 1672983 | ACTGG | GCTGT | GCTGT: 189<br>ACTGG: 0 | CDS | + | | | no annotation | LEUM_1698 | |
| 1684163 | GTCTC | ATCTT | ATCTT: 153<br>GTCTC: 0 | | | | | | | |
| 1695377 | ACCG | GCCA | GCCA: 273<br>ACCG: 0 | CDS | − | | | no annotation | LEUM_1726 | |
| 1696196 | GGCCGCTAGCATG | TGCAGCCAACATA | TGCAGCCAACATA: 189<br>GGCCGCTAGCATG: 0 | CDS | − | | | no annotation | LEUM_1726 | |
| 1696244 | TCGCAA | CCGTAG | CCGTAG: 215<br>TCGCAA: 0 | CDS | − | | | no annotation | LEUM_1726 | |
| 1716146 | TAATT | CAATC | CAATC: 45<br>TAATT: 0 | | | | | | | |
| 1717930 | ATCA | GTCT | GTCT: 47<br>ATCA: 0 | CDS | − | | | no annotation | LEUM_1748 | |
| 1717975 | ATCGATG | GTCTATA | GTCTATA: 22<br>ATCGATG: 0 | CDS | − | | | no annotation | LEUM_1748 | |
| 1718317 | ATCG | GTCT | GTCT: 10<br>ATCG: 0 | CDS | − | | | no annotation | LEUM_1748 | |
| 1718353 | ATTT | GTTC | GTTC: 22<br>ATTT: 0 | CDS | − | | | no annotation | LEUM_1748 | |
| 1719685 | GGA | AGG | AGG: 289<br>GGA: 2 | CDS | − | | | no annotation | LEUM_1748 | |
| 1725927 | TAGCC | CAGCT | CAGCT: 186<br>TAGCC: 1 | CDS | − | | | no annotation | LEUM_1752 | |
| 1726130 | GCTA | TCTG | TCTG: 43<br>GCTA: 0 | CDS | − | | | no annotation | LEUM_1752 | |
| 1726179 | TATCC | CAGCT | CAGCT: 65<br>TATCC: 0 | CDS | − | | | no annotation | LEUM_1752 | |
| 1726202 | GCTA | TCTG | TCTG: 90<br>GCTA: 0 | CDS | − | | | no annotation | LEUM_1752 | |
| 1726215 | TAGCC | CAGCT | CAGCT: 95<br>TAGCC: 0 | CDS | − | | | no annotation | LEUM_1752 | |
| 1726251 | CAGCT | TAGCC | TAGCC: 143<br>CAGCT: 2 | CDS | − | | | no annotation | LEUM_1752 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1756654 | TCTAC | GCTAT | GCTAT: 128<br>TCTAC: 0 | | | | | | | |
| 1756824 | ATC | GTA | GTA: 145<br>ATC: 0 | CDS | − | | | no annotation | LEUM_1786 | |
| 1757247 | GAAA | AAAG | AAAG: 196<br>GAAA: 0 | CDS | − | | | no annotation | LEUM_1786 | |
| 1759552 | TACT | CACC | CACC: 256<br>TACT: 0 | CDS | + | | | no annotation | LEUM_1788 | |
| 1759606 | GGCG | AGCA | AGCA: 266<br>GGCG: 0 | CDS | + | | | no annotation | LEUM_1788 | |
| 1760925 | ACCCGATGGGTTGTATT | GCCACTAGGCTGCATTGCAT | GCCACTAGGCTGCAT: 37<br>ACCCGATGGGTGTATT: 0 | | | | | | | |
| 1760955 | CAAATGA | TAAGTGG | TAAGTGG: 35<br>CAAATGA: 0 | CDS | − | | | no annotation | LEUM_1791 | |
| 1760994 | GGCTGCAAACGCTGCACGCAGGCGCAGC | AGCAGCGAAACGAAAGCAGCGCGTAAAGCGTAAACGAAGT | AGCAGCGAAAGCAGCGCGTAAACGAAGT: 37<br>GGCTGCAAACGCTGCACGCAGGCGCAGC: 0 | CDS | − | | | no annotation | LEUM_1791 | |
| 1761057 | CTTGGGG | TTTTGGT | TTTTGGT: 167<br>CTTGGGG: 0 | CDS | − | | | no annotation | LEUM_1791 | |
| 1761069 | CTGGGGTATCAAAACGGTTACA | TTGTGGAATTAAATACTGTCACT | TTGTGGAATTAACTGTCACTCTGGGGTATCAAAACGGTTACA: 168<br>CTGGGGTATCAAAACGGTTACA: 0 | CDS | − | | | no annotation | LEUM_1791 | |
| 1761096 | GTTA | ATTG | ATTG: 166<br>GTTA: 0 | CDS | − | | | no annotation | LEUM_1791 | |
| 1761107 | CTGCCTGC | TTGCTTGT | TTGCTTGT: 173<br>CTGCCTGC: 0 | CDS | − | | | no annotation | LEUM_1791 | |
| 1764663 | TTC | CTG | CTG: 125<br>TTC: 0 | CDS | + | | | no annotation | LEUM_1793 | |
| 1766295 | TAA | CAG | CAG: 302<br>TAA: 0 | CDS | − | | | no annotation | LEUM_1794 | |
| 1776537 | CGA | AGC | AGC: 191<br>CGA: 0 | CDS | − | | | no annotation | LEUM_1803 | |
| 1790033 | CTGT | TTGC | TTGC: 198<br>CTGT: 0 | CDS | − | | | no annotation | LEUM_1817 | |
| 1824412 | CAA | AAG | AAG: 178<br>CAA: 0 | CDS | − | | | no annotation | LEUM_1850 | |
| 1830003 | GAGA | AAGG | AAGG: 208<br>GAGA: 0 | | | | | | | |
| 1842065 | ACCA | GCCC | GCCC: 231<br>ACCA: 0 | CDS | − | | | no annotation | LEUM_1868 | atpC |
| 1857246 | ATTACCTTTGATAAC | GTTATCAAAGGTAAT | GTTATCAAAGGTAAT: 71<br>ATTACCTTTGATAAC: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1860337 | AGA | GGG | GGG: 145 AGA: 0 | CDS | − | | | no annotation | LEUM_1886 | |
| 1861225 | CTTTGCA | TTTTACG | TTTTACG: 221 CTTTGCA: 0 | cos | − | | | no annotation | LEUM_1888 | |
| 1875169 | ATT | GTC | GTC: 252 ATT: 0 | CDS | − | | | no annotation | LEUM_1900 | |
| 1878574 | ACG | AA | AA: 157 ACG: 1 | | | | | | | |
| 1878900 | GCAAGT | ATAAGC | ATAAGC: 121 GCAAGT: 0 | CDS | + | | | no annotation | LEUM_1905 | |
| 1878918 | GTG | TTT | TTT: 121 GTG: 0 | CDS | + | | | no annotation | LEUM_1905 | |
| 1878926 | CTTT | TTTC | TTTC: 114 CTTT: 0 | CDS | + | | | no annotation | LEUM_1905 | |
| 1878938 | ATAGA | GTAA | GTAA: 113 ATAGA: 0 | CDS | + | | | no annotation | LEUM_1905 | |
| 1878945 | TCCC | GACG | GACG: 112 TCCC: 0 | | | | | | | |
| 1878959 | GTAT | TTAA | TTAA: 139 GTAT: 0 | | | | | | | |
| 1879309 | CCTAGCCA | TCTGGCCT | TCTGGCCT: 176 CCTAGCCA: 0 | | | | | | | |
| 1882947 | AGTAGT | GGTTGC | GGTTGC: 244 AGTAGT: 0 | | | | | | | |
| 1882969 | TACAT | GACAC | GACAC: 243 TACAT: 0 | | | | | | | |
| 1886783 | CCAATCA | TCGATCG | TCGATCG: 207 CCAATCA: 0 | CDS | + | | | no annotation | LEUM_1917 | |
| 1887546 | TAGG | CAAA | CAAA: 137 TAGG: 0 | CDS | − | | | no annotation | LEUM_1919 | |
| 1887555 | ACGTGTT | TCGCGTA | TCGCGTA: 147 ACGTGTT: 0 | CDS | − | | | no annotation | LEUM_1919 | |
| 1887567 | CAATGAACCG | TAGAGAGCCA | TAGAGAGCCA: 147 CAATGAACCG: 0 | CDS | − | | | no annotation | LEUM_1919 | |
| 1887582 | TTCA | CTCG | CTCG: 153 TTCA: 0 | CDS | − | | | no annotation | LEUM_1919 | |
| 1887645 | GGCT | AGCC | AGCC: 249 GGCT: 0 | CDS | − | | | no annotation | LEUM_1919 | |
| 1887654 | CTTG | TTTA | TTTA: 252 CTTG: 0 | CDS | − | | | no annotation | LEUM_1919 | |
| 1887666 | ACGAAGC | GCGCAAT | GCGCAAT: 172 ACGAAGC: 0 | CDS | − | | | no annotation | LEUM_1919 | |
| 1887684 | CTGG | TTGT | TTGT: 196 CTGG: 0 | CDS | − | | | no annotation | LEUM_1919 | |
| 1887711 | TGTCACTTGA | AGTTACCTGG | AGTTACCTGG: 239 TGTCACTTGA: 0 | CDS | − | | | no annotation | LEUM_1919 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1887732 | GCCG | ACCA | ACCA: 275 GCCG: 0 | CDS | − | | | no annotation | LEUM_1919 | |
| 1887771 | CTTC | TTTT | TTTT: 299 CTTC: 0 | CDS | − | | | no annotation | LEUM_1919 | |
| 1887795 | CGCTCCA | TGCACCG | TGCACCG: 316 CGCTCCA: 0 | CDS | − | | | no annotation | LEUM_1919 | |
| 1887821 | ATTTA | GCTTG | GCTTG: 277 ATTTA: 0 | CDS | − | | | no annotation | LEUM_1919 | |
| 1887831 | GTTTCCA | ATTACCG | ATTACCG: 281 GTTTCCA: 0 | CDS | − | | | no annotation | LEUM_1919 | |
| 1887852 | GTGA | ATGT | ATGT: 312 GTGA: 0 | CDS | − | | | no annotation | LEUM_1919 | |
| 1887867 | ACTG | GCTA | GCTA: 324 ACTG: 0 | CDS | − | | | no annotation | LEUM_1919 | |
| 1887897 | TAG | CAA | CAA: 307 TAG: 0 | CDS | − | | | no annotation | LEUM_1919 | |
| 1887906 | AGCA | GGCG | GGCG: 305 AGCA: 0 | CDS | − | | | no annotation | LEUM_1919 | |
| 1896684 | TCAGC | CCAGA | CCAGA: 220 TCAGC: 0 | CDS | − | | | no annotation | LEUM_1927 | |
| 1897538 | GCGC | ACGT | ACGT: 286 GCGC: 0 | CDS | − | | | no annotation | LEUM_1928 | |
| 1915818 | AGTT | GGTC | GGTC: 305 AGTT: 0 | CDS | − | | | no annotation | LEUM_1944 | |
| 1917475 | TTA | CTC | CTC: 134 TTA: 0 | CDS | − | | | no annotation | LEUM_1945 | |
| 1933246 | TCA | CCG | CCG: 225 TCA: 0 | CDS | + | | | no annotation | LEUM_1960 | |
| 1933618 | CATT | TATA | TATA: 200 CATT: 0 | CDS | + | | | no annotation | LEUM_1960 | |
| 1933723 | GCCCA | TCCCG | TCCCG: 175 GCCCA: 0 | CDS | + | | | no annotation | LEUM_1960 | |
| 1933941 | GTCT | ATT | ATT: 134 GTCT: 0 | | | | | | | |
| 1934018 | ATATTAC | TTGTTAT | TTGTTAT: 133 ATATTAC: 0 | | | | | | | |
| 1934029 | ACAA | GTAT | GTAT: 135 ACAA: 0 | | | | | | | |
| 1934072 | GTAA | ATA | ATA: 142 GTAA: 0 | | | | | | | |
| 1934080 | ATGTGGC | GTGTT GT | GTGTTGT: 142 ATGTGGC: 0 | | | | | | | |
| 1952692 | GAATA | TAATG | TAATG: 97 GAATA: 0 | | | | | | | |
| 1952721 | GAAG | AAAT | AAAT: 82 GAAG: 0 | | | | | | | |
| 1952732 | GTGTT | TCGTC | TCGTC: 78 GTGTT: 0 | | | | | | | |
| 1953810 | CGGTG | TTGTA | TTGTA: 462 CGGTG: 0 | | | | | | | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 1960043 | CAATT | TAATC | TAATC: 36<br>CAATT: 0 | | | | | | | |
| 1960073 | TTTGGG | AAGGGA | AAGGGA: 39<br>TTTGGG: 0 | | | | | | | |
| 1960134 | TGTGTTAAATAC | AGTGCTATATTT | AGTGCTATATTT: 34<br>TGTGTTAAATAC: 0 | CDS | − | | | no annotation | LEUM_1991 | |
| 1960163 | GTCA | ATCT | ATCT: 36<br>GTCA: 0 | CDS | − | | | no annotation | LEUM_1991 | |
| 1960179 | ATTGC | CTTAA | CTTAA: 39<br>ATTGC: 0 | CDS | − | | | no annotation | LEUM_1991 | |
| 1960376 | TGCT | AGCA | AGCA: 107<br>TGCT: 0 | CDS | − | | | no annotation | LEUM_1991 | |
| 1960390 | GTCTT | ACCTC | ACCTC: 106<br>GTCTT: 0 | CDS | − | | | no annotation | LEUM_1991 | |
| 1960567 | AAA | CAC | CAC: 136<br>AAA: 0 | | | | | | | |
| 1960585 | CTGCA | TTGCG | TTGCG: 122<br>CTGCA: 0 | | | | | | | |
| 1960664 | TGTC | CGTT | CGTT: 161<br>TGTC: 0 | | | | | | | |
| 1969902 | GTC | ATT | ATT: 182<br>GTC: 0 | CDS | + | | | no annotation | LEUM_2001 | |
| 1969941 | GTTTA | ATTTT | ATTTT: 173<br>GTTTA: 0 | CDS | + | | | no annotation | LEUM_2001 | |
| 1970013 | TTAT | CTGC | CTGC: 152<br>TTAT: 0 | CDS | + | | | no annotation | LEUM_2001 | |
| 1978224 | AGTAT | GGTAC | GGTAC: 277<br>AGTAT: 0 | CDS | − | | | no annotation | LEUM_2010 | |
| 1980589 | CTTGT | TTTGC | TTTGC: 192<br>CTTGT: 0 | | | | | | | |
| 1994040 | TAATT | GAATC | GAATC: 291<br>TAATT: 0 | CDS | − | | | no annotation | LEUM_2027 | |
| 1996966 | GTGG | ATGA | ATGA: 363<br>GTGG: 0 | CDS | − | | | no annotation | LEUM_2030 | |
| 1996984 | GATT | AATC | AATC: 258<br>GATT: 0 | CDS | − | | | no annotation | LEUM_2030 | |
| 1996993 | GGCAGGC | AGCTGGT | AGCTGGT: 241<br>GGCAGGC: 0 | CDS | − | | | no annotation | LEUM_2030 | |
| 1997007 | GACCCCGTTCAGGC | ATCCTCGCTCCGCGGT | ATCCTCGCTCCGCGGT: 235<br>GACCCCGTTCAGGC: 0 | CDS | − | | | no annotation | LEUM_2030 | |
| 1997032 | CACA | AACG | AACG: 318<br>CACA: 0 | CDS | − | | | no annotation | LEUM_2030 | |
| 2025691 | GCTA | ACTG | ACTG: 240<br>GCTA: 0 | CDS | − | | | no annotation | LEUM_2060 | |
| 2025829 | AACA | GACG | GACG: 213<br>AACA: 0 | CDS | − | | | no annotation | LEUM_2060 | |

TABLE 19-continued

Polymorphisms identified by variant analysis BF2 compared to ATCC8293.

| POS | REF | ALT | EVIDENCE | FTYPE | STRAND | NT_POS | AA_POS | EFFECT | LOCUS_TAG | GENE |
|---|---|---|---|---|---|---|---|---|---|---|
| 2026633 | GCAG | ACAA | ACAA: 327 GCAG: 0 | CDS | − | | | no annotation | LEUM_2061 | |
| 2036598 | GCCT | ACCC | ACCC: 291 GCCT: 0 | CDS | − | | | no annotation | LEUM_2072 | |
| 2037136 | TCGA | CCGT | CCGT: 198 TCGA: 0 | | | | | | | |
| 2037152 | TAACA | GAACG | GAACG: 210 TAACA: 0 | | | | | | | |
| 2037383 | TCCA | CCCT | CCCT: 285 TCCA: 0 | CDS | − | | | no annotation | LEUM_2073 | |
| 2037417 | CGT | TGC | TGC: 259 CGT: 0 | CDS | − | | | no annotation | LEUM_2073 | |
| 2037438 | GTATC | TTATT | TTATT: 286 GTATC: 0 | CDS | − | | | no annotation | LEUM_2073 | |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from Australian Provisional Application No. 2017903944 entitled "Isothiocyanate containing Brassicaceae products and method of preparation thereof" filed on 28 Sep. 2017, the entire contents of which are hereby incorporated by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Agerbirk et al. (2012) Phytochemisty 77:16-45.
Alvarez-Sieiro et al. (2016) Applied Microbiology and Biotechnology 7:2939-2951.
Axelsson et al. (2017) Sci Transl Med 9(394).
Cai and Wang (2016) Food Chem 1; 210:451-6.
Capuano et al. (2017) Curr Pharm Des 19:2697-2721.
Chuat and Dalmasso (2015) p. 241-251. In Jordan and Dalmasso (ed.), Pulse Field Gel Electrophoresis: Methods and Protocols, vol. 1301. Springer, New York, NY
Dosz and Jeffery (2013) Journal of Functional Foods 5:987-990.
Filannino et al. (2015). Food microbiology 46:272-279.
Guzman-Lopez et al. (2009). J hid Microbiol Biotechnol 36:11-20.
Halkier et al. (2006) Annual Reviews in Plant Biology 57:303-33.
Huang et al. (2002) Journal of agricultural and food chemistry 50(16), 4437-4444.
Jeffery and Araya (2009) Phytochemistry Reviews 8:283-298.
Kim and Park (2016) Excli J 15:571-577.
Latte et al. (2011) Food & Chemical Toxicology, 49(12), 3287-3309.
Li et al. (2012) Journal of Medicinal Plants Research 6:4796-4803.
Moktari et al. (2017) J Cell Commun Signal July 23.
Singleton and Rossi (1965) American Journal of Enology and Viticulture 16:144-158.
Verkerk et al. (2009) Molecular Nutrition and Food Research 53:S219-S265.
Xia and Wishart (2016) Current Protocols in Bioinformatics 55:14.10.1-14.10.91.

The invention claimed is:

1. A method of preparing an isothiocyanate containing product from Brassicaceae material comprising a glucosinolate comprising:
   i) pre-treating the Brassicaceae material to improve the access of myrosinase to the glucosinolate; and
   ii) fermenting the material obtained by step i) with lactic acid bacteria to form the isothiocyanate containing product,
   wherein the lactic acid bacteria is selected from one or more of:
   a) *Leuconostoc mesenteroides* BF1 deposited under V17/021729 on 25 Sep. 2017 at the National Measurement Institute Australia;
   b) *Leuconostoc mesenteroides* BF2 deposited under V17/021730 on 25 Sep. 2017 at the National Measurement Institute Australia;
   c) *Lactobacillus plantarum* B1 deposited under V17/021731 on 25 Sep. 2017 at the National Measurement Institute Australia;
   d) *Lactobacillus plantarum* B2 deposited under V17/021732 on 25 Sep. 2017 at the National Measurement Institute Australia;
   e) *Lactobacillus plantarum* B3 deposited under V17/021733 on 25 Sep. 2017 at the National Measurement Institute Australia;
   f) *Lactobacillus plantarum* B4 deposited under V17/021734 on 25 Sep. 2017 at the National Measurement Institute Australia; and
   e) *Lactobacillus plantarum* B5 deposited under V17/021735 on 25 Sep. 2017 at the National Measurement Institute Australia.

2. The method of claim 1, wherein for option (b) the pre-treating comprises one or more of the following:
   i) heating;
   ii) macerating;
   iii) microwaving;
   iv) exposure to high frequency sound waves (ultrasound), or
   v) pulse electric field processing.

3. The method of claim 1, wherein pre-treating comprises one or both of:
   i) heating the Brassicaceae material before macerating or heating and macerating the Brassicaceae material at the same time; or
   ii) heating the Brassicaceae material to a temperature of about 50° C. to about 70° C. followed by maceration.

4. The method of claim 1, wherein at least one of the following applies:
   i) the isothiocyanate containing product comprises at least about 10 times more isothiocyanate than macerated Brassicaceae material; and
   ii) the isothiocyanate containing product comprises at least about 2 times the expected maximum yield of isothiocyanate based on the extractable glucosinolate content of the Brassicaceae material.

5. The method of claim 1, which additionally comprises acidification of the isothiocyanate containing product from step ii) of claim 1 to a pH of about 4.4 or less.

6. The method claim 1, wherein fermentation is at about 22° C. to about 34° C., or is at about 30° C.

7. The method of claim 1, wherein the isothiocyanate containing product has one or more or all of the following features:
   i) the isothiocyanate in the product is stable for at least 4 weeks, or at least 8 weeks, or at least 12 weeks when stored at about 4° C. to about 25° C.;
   ii) the product is resistant to yeast, mould and/or coliform growth for at least 4 weeks, or at least 8 weeks, or at least 12 weeks when stored at about 4° C. to about 25° C.;
   iii) the product comprises lactic acid bacteria at a concentration of at least $10^8$ CFU/g; and
   iv) the product comprises an isothiocyanate bioactive derivative.

8. The method of claim 1, wherein the glucosinolate is selected from one of: glucoraphanin (4-methylsulphinylbutyl), sinigrin (2-propenyl), gluconapin (3-butenyl), glucobrassicanapin (4-pentenyl), progoitrin (2 (R)-2-hydroxy-3-butenyl), epiprogoitrin (2 (S)-2-hydroxy-3-butenyl), gluconapoleiferin (2-hydroxy-4-pentenyl), glucoibervirin (3-methylthiopropyl), glucoerucin (4-methylthiobutyl), dehydroerucin (4-methylthio-3-butenyl), glucoiberin (3-methylsulphinylpropyl), glucoraphenin (4-methylsulphinyl-3-butenyl), glucoalyssin (5-methylsulphinylpentenyl), glucoerysolin (3-methylsulphonylbutyl), 4-mercaptobutyl, glucobrassicin (3-indolylmethyl), 4-hydroxyglucobrassicin (4-hydroxy-3-indolylmethyl), 4-methoxyglucobrassicin (4-methoxy-3-indolylmethyl), neoglucobrassicin (1-methoxy-3-indolylmethyl), glucotropaeolin (benzyl), and gluconasturtiin (2-phenylethyl).

9. The method of claim 1, wherein the isothiocyanate is sulforaphane.

10. The method of claim 1, wherein the Brassicaceae is selected from *Brassica oleracea, Brassica balearica, Brassica carinata, Brassica elongate, Brassica fruticulosa, Brassica hilarionis, Brassica juncea, Brassica napus, Brassica narinosa, Brassica nigra, Brassica perviridis, Brassica rapa, Brassica rupestris, Brassica septiceps* and *Brassica tournefortii*.

11. The method of claim 1, wherein after fermentation the isothiocyanate containing product is post-treated to inactivate microbes.

12. The method of claim 1, wherein the Brassicaceae is a *Brassica*.

13. The method of claim 1, wherein the Brassicaceae material is macerated so that at least about 80% of the Brassicaceae material is of a size of about 2 mm or less.

14. The method of claim 1, wherein pre-treating comprises maceration, and the isothiocyanate containing product comprises 10 times more isothiocyanate than macerated Brassicaceae material.

15. The method of claim 5, wherein after acidification, the isothiocyanate containing product is post-treated to inactivate microbes.

* * * * *